US007829671B2

(12) United States Patent
Bellacosa

(10) Patent No.: US 7,829,671 B2
(45) Date of Patent: Nov. 9, 2010

(54) GENE ENCODING A DNA REPAIR ENZYME AND METHODS OF USE THEREOF

(75) Inventor: Alfonso Bellacosa, Philadelphia, PA (US)

(73) Assignee: Fox Chase Cancer Center, Philadelphia, PA (US)

( * ) Notice: Subject to any disclaimer, the term of this patent is extended or adjusted under 35 U.S.C. 154(b) by 43 days.

(21) Appl. No.: 12/354,864

(22) Filed: Jan. 16, 2009

(65) Prior Publication Data

US 2009/0274681 A1 Nov. 5, 2009

Related U.S. Application Data

(63) Continuation of application No. 11/739,558, filed on Apr. 24, 2007, now Pat. No. 7,491,807, which is a continuation of application No. 10/629,951, filed on Jul. 29, 2003, now Pat. No. 7,208,583, which is a continuation of application No. 09/629,222, filed on Jul. 31, 2000, now Pat. No. 6,599,700, which is a continuation-in-part of application No. 09/463,891, filed as application No. PCT/US98/15828 on Jul. 28, 1999, now abandoned.

(60) Provisional application No. 60/053,936, filed on Jul. 28, 1997.

(51) Int. Cl.

| | |
|---|---|
| ***C07K 1/00*** | (2006.01) |
| ***C07K 14/00*** | (2006.01) |
| ***C07K 17/00*** | (2006.01) |
| ***G01N 33/00*** | (2006.01) |
| ***G01N 33/53*** | (2006.01) |
| ***G01N 33/573*** | (2006.01) |
| ***A01N 37/18*** | (2006.01) |
| ***A01N 61/00*** | (2006.01) |
| ***A61K 31/00*** | (2006.01) |
| ***A61K 38/00*** | (2006.01) |
| ***A61K 38/16*** | (2006.01) |
| ***C12Q 1/00*** | (2006.01) |

(52) U.S. Cl. ............................ 530/350; 436/86; 514/1; 514/2; 514/8; 514/12; 435/4; 435/7.1; 435/7.4; 435/7.92; 435/7.93

(58) Field of Classification Search ....................... None
See application file for complete search history.

(56) References Cited

U.S. PATENT DOCUMENTS

| | | | |
|---|---|---|---|
| 6,599,700 | B1 | 7/2003 | Bellacosa |
| 7,208,583 | B2 | 4/2007 | Bellacosa |
| 7,491,807 | B2 | 2/2009 | Bellacosa |

OTHER PUBLICATIONS

Rudikoff et al (Proc. Natl. Acad. Sci. USA 1982 vol. 79 p. 1979).

Modrich, P., "Mechanisms and Biological Effects of Mismatch Repair"; Annu. Rev. Genet. (1991), 25: 229-53.

Liu, B. et al., "Analysis of mismatch repair genes in hereditary non-polyposis colorectal cancer patients"; Nature Medicine (1996), vol. 2, No. 2, 169-174.

Plummer, S.J. et al., "Are we any closer to genetic testing for common malignancies?"; Nature Medicine (1996), vol. 2, No. 2, 156-158.

Bird, A., "The Essentials of DNA Methylation"; Cell (1992), vol. 70, 5-8.

Barras, F. et al., "The Great GATC: DNA methylation in *E. coli*"; TIG (1989), vol. 5, No. 5, 139-143.

Hare, J.T. et al., "One role for DNA methylation in vertebrate cells is strand discrimination in mismatch repair"; Proc. Natl. Acad. Sci. USA (1985), vol. 82, 7350-7354.

Kolodner, R.D.,"Mismatch repair: mechanisms and relationship to cancer susceptibility"; TIBS—Oct. 1995, 397-401.

Au, K.G. et al., "Initiation of Methyl-directed Mismatch Repair"; The Journal of Biological Chemistry (1992), vol. 267, No. 17, 12142-12148.

Nan, X. et al., "Dissection of the methyl-CpG binding domain from the chromosomal protein MeCP2"; Nucleic Acids Research (1993), vol. 21, No. 21, 4886-4892.

Kolodner, R., "Biochemistry and genetics of eukaryotic mismatch repair"; Genes & Development (1996), 10: 1433-1442.

Modrich, P. et al., "Mismatch Repair in Replication Fidelity, Genetic Recombination, and Cancer Biology"; Annu. Rev. Biochem. (1996), 65: 101-33.

Mashal, R.D. et al., "Detection of mutations by cleavage of DNA heteroduplexes with bacteriophage resolvases"; Nature Genetic (1995), vol. 9, 177-183.

Dean, M., "Resolving DNA mutations"; Nature Genetics (1995), vol. 9, 103-104.

Liu, B. et al., "Mismatch repair gene defects in sporadic colorectal cancers with microsatellite instability"; Nature Genetics (1995), vol. 9, 48-55.

Lynch, H.T. et al., "Hereditary Nonpolyposis Colorectal Cancer (Lynch Syndrome)"; Cancer (1996), vol. 78, No. 6, 1149-1167.

Bellacosa, A. et al.; "Hereditary Nonpolyposis Colorectal Cancer: Review of Clinical, Molecular Genetics, and Counseling Aspects"; American Journal of Medical Genetics (1996), 62: 353-364.

Lewis, J.D. et al., "Purification, Sequence, and Cellular Localization of a Novel Chromosomal Protein That Binds to Methylated DNA"; Cell (1992), vol. 69, 905-914.

Smith, J. et al., "Mutation detection with MutH, MutL, and MutS mismatch repair proteins"; Proc. Natl. Acad. Sci. USA (1996), vol. 93, 4374-4379.

Umar, A. et al., "Requirement for PCNA in DNA Mismatch Repair at a Step Preceding DNA Resynthesis"; Cell (1996), vol. 87, 65-73.

(Continued)

*Primary Examiner*—Alana M Harris
(74) *Attorney, Agent, or Firm*—Patrick J. Hagan; Dann, Dorfman, Herrell and Skillman, P.C.

(57) ABSTRACT

An isolated nucleic acid molecule encoding a human DNA repair enzyme, MED1, is disclosed. Like other mismatch repair genes which are mutated in certain cancers, MED1, encoding nucleic acids, proteins and antibodies thereto may be used to advantage in genetic or cancer screening assays. MED1, which recognizes and cleaves DNA, may also be used for the diagnostic detection of mutations and genetic variants.

4 Claims, 44 Drawing Sheets

OTHER PUBLICATIONS

Wohrle, D. et al., "DNA Methylation and Triplet Repeat Stability: New Proposals Addressing Actual Questions on the CGG Repeat of Fragile X Syndrome"; American Journal of Medical Genectics (1996), 64: 266-267.

Viel, A. et al., "Characterization of MSH2 and MLHI Mutations in Itailian Families With Hereditary Nonpolyposis Colorectal Cancer"; Genes, Chromosomes & Cancer (1997), 18: 8-18.

Cross, S.H. et al., "A component of the transcriptional repressor MeCP1 shares a motif with DNA methyltransferase and HRX proteins"; Nature Genetics (1997), vol. 16, 256-259.

Datta, K. et al., "Akt Is a Direct Target of the Phosphatidylinositol 3-Kinase"; The Journal of Biological Chemistry (1996), vol. 271, No. 48, 30835-30839.

Blank, A. et al., "Activity Staining of Nucleolytic Enzymes after Sodium Dodecyl Sulfate-Polyacrylamide Gel Electrophoresis: Use of Aqueous Isopropanol to Remove Detergent from Gels"; Analytical Biochemistry (1982), 120:267-275.

1 GGCGGCGTCTGGGGCGCTTTCGCAACATTCAGACCTCGGTTGCAGCCCGGTGCCGTGAGCTGAAGAGGTTTCACATCTTACTCCGCCCCA 90
91 CACCCTGGGCGTTGCGGCGCTGGGCTCGTTGCTGCAGCCGGACCCTGCTCGATGGGCACGACTGGGCTGGAGAGTCTGAGTCTGGGGGAC 180
M G T T G L E S L S L G D

181 CGCGGAGCTGCCCCCACCGTCACCTCTAGTGAGCGCCTAGTCCCAGACCCGCCGAATGACCTCCGCAAAGAAGATGTTGCTATGGAATTG 270
R G A A P T V T S S E R L V P D P P N D L R K E D V A M E L

271 GAAAGAGTGGGAGAAGATGAGGAACAAATGATGATAAAAAGAAGCAGTGAATGTAATCCCTTGCTACAAGAACCCATCGCTTCTGCTCAG 360
E R V G E D E E Q M M I K R S S E C N P L L Q E P I A S A Q

361 TTTGGTGCTACTGCAGGAACAGAATGCCGTAAGTCTGTCCCATGTGGATGGGAAAGAGTTGTGAAGCAAAGGTTATTTGGGAAGACAGCA 450
F G A T A G T E C R K S V P C G W E R V V K Q R L F G K T A

451 GGAAGATTTGATGTGTACTTTATCAGCCCACAAGGACTGAAGTTCAGATCCAAAAGTTCACTTGCTAATTATCTTCACAAAAATGGAGAG 540
G R F D V Y F I S P Q G L K F R S K S S L A N Y L H K N G E

541 ACTTCTCTTAAGCCAGAAGATTTTGATTTTACTGTACTTTCTAAAAGGGGTATCAAGTCAAGATATAAAGACTGCAGCATGGCAGCCCTG 630
T S L K P E D F D F T V L S K R G I K S R Y K D C S M A A L

631 ACATCCCATCTACAAAACCAAAGTAACAATTCAAACTGGAACCTCAGGACCCGAAGCAAGTGCAAAAAGGATGTGTTTATGCCGCCAAGT 720
T S H L Q N Q S N N S N W N L R T R S K C K K D V F M P P S

721 AGTAGTTCAGAGTTGCAGGAGAGCAGAGGACTCTCTAACTTTACTTCCACTCATTTGCTTTTGAAAGAAGATGAGGGTGTTGATGATGTT 810
S S S E L Q E S R G L S N F T S T H L L L K E D E G V D D V

811 AACTTCAGAAAGGTTAGAAAGCCCAAAGGAAAGGTGACTATTTTGAAAGGAATCCCAATTAAGAAAACTAAAAAAGGATGTAGGAAGAGC 900
N F R K V R K P K G K V T I L K G I P I K K T K K G C R K S

901 TGTTCAGGTTTTGTTCAAAGTGATAGCAAAAGAGAATCTGTGTGTAATAAAGCAGATGCTGAAAGTGAACCTGTTGCACAAAAAAGTCAG 990
C S G F V Q S D S K R E S V C N K A D A E S E P V A Q K S Q

991 CTTGATAGAACTGTCTGCATTTCTGATGCTGGAGCATGTGGTGAGACCCTCAGTGTGACCAGTGAAGAAAACAGCCTTGTAAAAAAAAAA 1080
L D R T V C I S D A G A C G E T L S V T S E E N S L V K K K

1081 GAAAGATCATTGAGTTCAGGATCAAATTTTTGTTCTGAACAAAAAACTTCTGGCATCATAAACAAATTTTGTTCAGCCAAAGACTCAGAA 1170
E R S L S S G S N F C S E Q K T S G I I N K F C S A K D S E

1171 CACAACGAGAAGTATGAGGATACCTTTTTAGAATCTGAAGAAATCGGAACAAAAGTAGAAGTTGTGGAAAGGAAAGAACATTTGCATACT 1260
H N E K Y E D T F L E S E E I G T K V E V V E R K E H L H T

1261 GACATTTTAAAACGTGGCTCTGAAATGGACAACAACTGCTCACCAACCAGGAAAGACTTCACTGGTGAGAAAATATTTCAAGAAGATACC 1350
D I L K R G S E M D N N C S P T R K D F T G E K I F Q E D T

1351 ATCCCACGAACACAGATAGAAAGAAGGAAAAACAAGCCTGTATTTTTCCAGCAAATATAACAAAGAAGCTCTTAGCCCCCCACGACGTAAA 1440
I P R T Q I E R R K T S L Y F S S K Y N K E A L S P P R R K

1441 GCCTTTAAGAAATGGACACCTCCTCGGTCACCTTTTAATCTCGTTCAAGAAACACTTTTTCATGATCCATGGAAGCTTCTCATCGCTACT 1530
A F K K W T P P R S P F N L V Q E T L F H D P W K L L I A T

1531 ATATTTCTCAATCGGACCTCAGGCAAAATGGCAATACCTGTGCTTTGGAAGTTTCTGGAGAAGTATCCTTCAGCTGAGGTAGCAAGAACC 1620
I F L N R T S G K M A I P V L W K F L E K Y P S A E V A R T

1621 GCAGACTGGAGAGATGTGTCAGAACTTCTTAAACCTCTTGGTCTCTACGATCTTCGGGCAAAAACCATTGTCAAGTTCTCAGATGAATAC 1710
A D W R D V S E L L K P L G L Y D L R A K T I V K F S D E Y

1711 CTGACAAAGCAGTGGAAGTATCCAATTGAGCTTCATGGGATTGGTAAATATGGCAACGACTCTTACCGAATTTTTTGTGTCAATGAGTGG 1800
L T K Q W K Y P I E L H G I G K Y G N D S Y R I F C V N E W

1801 AAGCAGGTGCACCCTGAAGACCACAAATTAAATAAATATCATGACTGGCTTTGGGAAAATCATGAAAAATTAAGTTTATCTTAAACTCTG 1890
K Q V H P E D H K L N K Y H D W L W E N H E K L S L S *

1891 CAGCTTTCAAGCTCATCTGTTATGCATAGCTTTGCACTTCAAAAAAGCTTAATTAAGTACAACCAACCACCTTTCCAGCCATAGAGATTT 1980
1981 TAATTAGCCCAACTAGAAGCCTAGTGTGTGTGCTTTCTTAATGTGTGTGCCAATGGTGGATCTTTGCTACTGAATGTGTTTGAACATGTT 2070
2071 TTGAGATTTTTTTAAAATAAATTATTATTTGACAACAAAAAAAAAAAAAAAAAAAAAAAAAAAAAAAAAAAAAAAAAAAAAAAAA 2152

Fig. 3

```
hmed1   KEDVAMELER V......... GEDEEQMMIK RSSECNPLLQ EPIAS
rmecp2  KEDKEGKHEP LQPSAHHSAE PAEAGKAETS ESSGSAPAVP EASAS

hmed1   AQ.....FGA TAGTECRKSV PCGWERVVKQ RLFGKTAGRF DVYFI
rmecp2  PKQRRSIIRD RGPMYDDPTL PEGWTRKLKQ RKSGRSAGKY DVYLI

hmed1   SPQGLKFRSK SSLANVLHKN GETSLKPEDF DFTVLSKRGI KSR K
rmecp2  NPQGKAFRSK VELIAYFEKV GDTSLDPNDF DFTVTG.RGS PSR .

hmed1   EDKEGKHEP
rmecp2  .........
```

Fig. 4A

```
MED1 IASAQFGATA GTECRKSVPC GWERVVKQRL FGKTAGRFDV YFISPQGLKF RSKSSLANYL 60
PCM1 MAEDWLDCPA .......LGP GWKRREVFRK SGATCGRSDT YYQSPTGDRI RSKVELTRYL 53

MED1 HKNGETSLKP EDFDFTVLSK RGIKS85
PCM1 GPACDLT..L FDFKQGILCY PAPKA76
```

Fig. 4C

1 CAAGGAAGAT ATTGCTGTTG GACTGGGAGG AGTGGGAGAA GATGGAAAGG
51 ACCTGGTGAT AAGCAGTGAG CGCAGCTCCC TTCTCCAAGA GCCCACTGCT
101 TCTACTCTGT CTAGTACTAC AGCGACAGAA GGCCACAAGC CTGTCCCGTG
151 TGGATGGGAA AGAGTTGTGA AGCAAAGGTT ATCTGGGAAA ACTGCAGGAA
201 AATTTGATGT ATACTTTATC AGCCCACAAG GATTGAAGTT CAGATCAAAA
251 CGTTCACTTG CTAATTATCT TCTCAAAAAT GGGGAGACTT TTCTTAAGCC
301 TGAAGATTTT AATTTTACTG TACTGCCGAA AGGGAGCATC AATCCCGGTT
351 ATAAACACCA AAGTTTGGCA GCTCTGACTT CCCTGCAGCC AAATGAAACT
401 GACGTTTCAA AGCAGAACCT CAAGACACGA AGCAAGTGGA AAACAGATGT
451 GTTGCCTCTG CCCAGTGGTA CTTCAGAGTC GCCAGAAAGC AGCGGACTGT
501 CTAACTCTAA CTCGGCTTGC TTGCTATTGA GAGAACATAG GGACATTCAG
551 GATGTTGACT CTGAGAAGAG GAGAAAGTCC AAAAGAAAGG TGACTGTTTT
601 GAAAGGAACT GCAAGTCAGA AAACCAAACA AAAGTGCAGG AAGAGTCTCT
651 TAGAGTCTAC TCAAAGAAAC AGAAAAAGAG CATCTGTGGT TCAGAAGGTG
701 GGTGCTGATC GCGAGCTGGT GCCACAGGAA AGTCAACTCA ACAGAACCCT
751 CTGCCCTGCA GATGCCTGTG CAAGGGAGAC TGTTGGCCTG GCTGGGGAAG
801 AAAAATCACC AAGCCCAGGA CTGGATCTTT GTTTCATACA AGTAACTTCT
851 GGCACCACAA ACAAATTCCA TTCAACTGAA GCAGCAGGTG AAGCAAATCG
901 TGAGCAGACT TTTTTAGAAT CAGAGGAAAT CAGATCGAAG GGAGACAGAA
951 AGGGGGAGGC ACATTTGCAT ACTGGTGTTT TACAGGATGG CTCTGAAATG
1001 CCCAGCTGCT CACAAGCCAA GAAACACTTT ACTTCTGAGA CATTTCAAGA
1051 AGACAGCATC CCACGGACAC AAGTAGAAAA AAGGAAAACA AGCCTGTATT
1101 TTTCCAGCAA GTACAACAAA GAAGCTCTTA GCCCCCCAAG ACGCAAATCC
1151 TTCAAGAAAT GGACCCCTCC TCGGTCACCT TTTAATCTTG TTCAAGAAAT
1201 ACTTTTCCAT GACCCATGGA AGCTCCTCAT CGCGACTATA TTTCTCAATC
1251 GGACCTCAGG CAAGATGGCC ATCCCTGTGC TGTGGGAGTT TCTAGAGAAG
1301 TACCCTTCAG CTGAAGTGGC CCGAGCTGCC GACTGGAGGG ACGTGTCGGA

Fig. 16A

1351 GCTTCTCAAG CCTCTTGGTC TCTACGATCT CCGTGCAAAA ACCATTATCA

1401 AGTTCTCAGA TGAATATCTG ACAAAGCAGT GGAGGTATCC GATTGAGCTT

1451 CATGGGATTT GGTTAAAATA TGGCAACGAC TCTACCGGAT CTTTTGTGTC

1501 AATGAATGGA ACAG

Fig. 16B mouse MED1 protein (upper sequence) x human MED1 protein (lower sequence)

```
  1 KEDIAVGLGGVGEDGKDLVI..SSERSSLLQEPTAST.LSSTTATEGHKP  47
    |||:|. |  ||||  .:.|  ||| . ||||| ||   .|  ||  |
 36 KEDVAMELERVGEDEEQMMIKRSSECNPLLQEPIASAQFGATAGTECRKS  85

 48 VPCGWERVVKQRLSGKTAGKFDVYFISPQGLKFRSKRSLANYLLKNGETF  97
    ||||||||||||| ||||| :|||||||||||||||||:|||||| ||||
 86 VPCGWERVVKQRLFGKTAGRFDVYFISPQGLKFRSKSSLANYLHKNGETS 135

 98 LKPEDFNFTVLPKGSINPGYKHQSLAALTSLQPNETDVSKQNLKTRSKWK 147
    ||||||.|||| |   ||  |:|||||  |:..| ||:||||  |
136 LKPEDFDFTVLSKRGIKSRYKDCSMAALTSHLQNQSNNSNWNLRTRSKCK 185

148 TDVLPLPSGTSESPESSGLSNSNSACLLLREHRDIQDVDSEKRRKSKRKV 197
    ||  || .||  ||  ||||  |  |||:|   :  ||.  || | ||
186 KDVFMPPSSSSELQESRGLSNFTSTHLLLKEDEGVDDVNFRKVRKPKGKV 235

198 TVLKGTASQKTKQKCRKSLLESTQRNRKRAS.................. 228
    |:|||  .|||. |||| | . || |
236 TILKGIPIKKTKKGCRKSCSGFVQSDSKRESVCNKADAESEPVAQKSQLD 285

229 ..............EDSIPRTQVEKRKTSLYFSSKYNKEALSPPRRKSF 263
                  ||.||||:|:||||||||||||||||||||||||.|
386 CSPTRKDFTGEKIFQEDTIPRTQIERRKTSLYFSSKYNKEALSPPRRKAF 435

264 KKWTPPRSPFNLVQEILFHDPWKLLIATIFLNRTSGKMAIPVLWEFLELY 313
    |||||||||||||||| ||||||||||||||||||||||||||.||| |
436 KKWTPPRSPFNLVQETLFHDPWKLLIATIFLNRTSGKMAIPVLWKFLEKY 485

314 PSAEVARAADWRDVSELLKPLGLYDLRAKTIIKFSDEYLTKQWRYPIELH 363
    ||||||| ||||||||||||||||||||||:||||||||||||:||||||
486 PSAEVARTADWRDVSELLKPLGLYDLRAKTIVKFSDEYLTKQWKYPIELH 535

364 GIWLKYGNDSYRIFCVNEWKQ 384
    || |||||||||||||||||
536 GIG.KYGNDSYRIFCVNEWKQ 555
```

Exon 2 ggttttgtttttccagCAAGGAAGATATTGCTGTTGGACTGGGAGGAGTG
GGAGAAGATGGAAAGGACCTGGTGATAAGCAGTGAGCGCAGCTCCCTTCT
CCAAGAGCCCACTGCTTCTACTCTGTCTAGTACTACAGCGACAGAAGGCC
ACAAGCCTGTCCCGTGTGGATGGGAAAGAGTTGTGAAGCAAAGGTTATCT
GGGAAAACTGCAGGAAAATTTGATGTATACTTTATCAGgtaagcatttag
Gaaggaaaata

Fig. 18B

Exon 3 cttttttttttccttttaagCCCACAAGGATTGAAGTTCAGATCAAAAC
GTTCACTTGCTAATTATCTTCTCAAAAATGGGGAGACTTTTCTTAAGCCT
GAAGATTTTAATTTTACTGTACTGCCGAAAGGGAGCATCAATCCCGGTTA
TAAACACCAAAGTTTGGCAGCTCTGACTTCCCTGCAGCCAAATGAAACTG
ACGTTTCAAAGCAGAACCTCAAGACACGAAGCAAGTGGAAAACAGATGTG
TTGCCTCTGCCCAGTGGTACTTCAGAGTCGCCAGAAAGCAGCGGACTGTC
TAACTCTAACTCGGCTTGCTTGCTATTGAGAGAACATAGGGACATTCAGG
ATGTTGACTCTGAGAAGAGGAGAAAGTCCAAAAGAAAGGTGACTGTTTTG
AAAGGAACTGCAAGTCAGAAAACCAAACAAAAGTGCAGGAAGAGTCTCTT
AGAGTCTACTCAAAGAAACAGAAAAAGAGCATCTGTGGTTCAGAAGGTGG
GTGCTGATCGCGAGCTGGTGCCACAGGAAAGTCAACTCAACAGAACCCTC
TGCCCTGCAGATGCCTGTGCAAGGGAGACTGTTGGCCTGGCTGGGGAAGA
AAAATCACCAAGCCCAGGACTGGATCTTTGTTTCATACAAGTAACTTCTG
GCACCACAAACAAATTCCATTCAACTGAAGCAGCAGGTGAAGCAAATCGT
GAGCAGACTTTTTTAGAATCAGAGGAAATCAGATCGAAGGGAGACAGAAA
GGGGGAGGCACATTTGCATACTGGTGTTTTACAGGATGGCTCTGAAATGC
CCAGCTGCTCACAAGCCAAGAAACACTTTACTTCTGAGACATTTCAAGgt
actcagtgcatgaaaa

Fig. 18C

Exon 4 gactataaactaattttgcttctcagAAGACAGCATCCCACGGACACAAG
TAGAAAAAAGGAAAACAAGCCTGTATTTTTCCAGCAAGTACAACAAAGAA
Ggtacccacctttccctaagc

Fig. 18D

Exon 5 tatatttntgnagCTCTTAGCCCCCCAAGACGCAAATCCTTCAAGAAATG
GACCCCTCCTCGGTCACCTTTTAATCTTGTTCAAGAAATACTTTTCCATG
ACCCATGGAAGCTCCTCATCGCGACTATATTTCTCAATCGGACCTCAGg
ttnggggtcattgncat

Fig. 18E

Exon 6 tgtttatgctccccagGCAAGATGGCCATCCCTGTGCTGTGGGAGTTTCT
AGAGAAGTACCCTTCAGCTGAAGTGGCCCGAGCTGCCGACTGGAGGGACG
TGTCGGAGCTTCTCAAGCCTCTTGGTCTCTACGATCTCCGTGCAAAAACC
ATTATCAAGTTCTCAGgtatgtccccagcccag

Fig. 18F

Exon 7 tggatgtgtatccctcagATGAATATCTGACAAAGCAGTGGAGGTATCCG
ATTGAGCTTCATGGGATTTGGTTAAAATATGGCAACGACTCTACCGGAT
CTTTTGTGTCAATGAATGGAACAGgtaagcccaccactggggcc

Fig. 19A

Exon 1

GCGGCGGCGTCTGGGGCGCTTTCGCAACATTCAGACCTCGGTTGCAGCCCGGTGCCGTGAGCTGAA
GAGGTTTCACATCTTACTCCGCCCCACACCCTGGGCGTTGCGGCGCTGGGCTCGTTGCTGCAGCCG
GACCCTGCTCGATGGGCACGACTGGGCTGGAGAGTCTGAGTCTGGGGGACCGCGGAGCTGCCCCCA
CCGTCACCTCTAGTGAGCGCCTAGTCCCAGACCCGCCGAATGACCTCCGgtaagttactgtcccct
tttgggcctcagtttcaccacctgtaaaatggtatcgggagagtggacagtgtgtgggcctttcta
acctttgacagagggtcggcanaaacctcgaagcccacgggtttagttactagggtctggagccca
ggtgctcttcctgtgcgatcagc...

Fig. 19B

Exon 2

...tttggaagacaggaaatactcccatagcacaagagtggtccacactgactttaatctccc
tcattttaatatggataatctatgtggttcctgcattgtcatggattaaaactgagtaggcagtgg
aagataaattttaaataagttaatcacttagactttgtttttccagCAAAGAAGATGTTGCTATGG
AATTGGAAAGAGTGGGAGAAGATGAGGAACAAATGATGATAAAAAGAAGCAGTGAATGTAATCCCT
TGCTACAAGAACCCATCGCTTCTGCTCAGTTTGGTGCTACTGCAGGAACAGAATGCCGTAAGTCTG
TCCCATGTGGATGGAAAGAGTTGTGAAGCAAAGGTTATTTGGAAGACAGCAGGAAGATTTGATG
TGTACTTTATCAGgtaagcatataagatggtaaagatagtacagccaaatgatttgtctgggcag
gtagtgggagcatagcaggaatcttagcttctttatattttaccataaaccattgcagattc
tattctttcaatgttgctattaattacatcaagtgatttggggaaattacatacattttgtccct
ccttctgtgaatggttaacgggtaggttgcatttagttatatttataaatttatattgtcataga
ggaaccatttaaaggccattatcactctttttcattttaaatgacagagacctatggcaacatt
tggaaattaattagaatctgaaatgtggtccagttcttttaaaagtcccttctatttactagcagt
aagtttcctttaatatcattttctag(continues into exon 3, see below)

Fig. 19C

Exon 3 aatctgaaatgtggtccagttcttttaaaagtcccttctatttactagcagtaagtttccttt
aatatcattttctagCCCACAAGGACTGAAGTTCAGATCCAAAAGTTCACTTGCTAATTATCTTCA
CAAAAATGGAGAGACTTCTCTTAAGCCAGAAGATTTTGATTTTACTGTACTTTCTAAAGGGGTAT
CAAGTCAAGATATAAAGACTGCAGCATGGCAGCCCTGACATCCCATCTACAAAACCAAAGTAACAA
TTCAAACTGGAACCTCAGGACCCGAAGCAAGTGCAAAAAGGATGTGTTTATGCCGCCAAGTAGTAG
TTCAGAGTTGCAGGAGAGCAGAGGACTCTCTAACTTTACTTCCACTCATTTGCTTTTGAAAGAAGA
TGAGGGTGTTGATGATGTTAACTTCAGAAAGGTTAGAAAGCCCAAAGGAAAGGTGACTATTTTGAA
AGGAATCCCAATTAAGAAAACTAAAAAAGGATGTAGGAAGAGCTGTTCAGGTTTTGTTCAAAGTGA
TAGCAAAAGANAATCTGTGTGTAATAAAGCAGATGCTGAAAGTGAACCTGTTGCACAAAAAAGTCA
GCTTGATAGAACTGTCTGCATTTCTGATGCTGGAGCATGTGGTGAGACCCTCAGTGTGAGCAGTGA
AGAAAACNGCCTTGTAAAAAAAAAAGAAAGATCATTGAGTTCAGGATCAAATTTTTGTTCTGAACA
AAAAACTTCTGGCATCATAAACAAATTTTGTTCAGCCAAAGACTCAGAACACAACGAGAAGTATGA
GGATACCTTTTTAGAATCTGAAGAAATCGGAACAAAAGTAGAAGTTGTGGAAAGGAAAGAACATTT
GCATACTGACATTTTAAAACGTGGCTCTGAAATGGACAACAACTGCTCACCAACCAGGAAAGACTT
CACTGgtgagaaaatatttcaaggtatccagtgctttcagcactattaaacattagtgatgagaa
atttatatgctgcatctgtatcgtgccatac Please note: at the end of exon 3, two alternative splice donor sites are present (see Sequence Variations, page 40 of the application).

Fig. 19D

Exon 4 and Exon 5 tagtaccaagttcatgggtcattagttagattaattgggtatttatgtaaagggcttagaatagtg
cctggcatgctttgtaatagtgttgatattattatttgcatccctcaatattgctttaagcta
aaccatagactccataaagtgtttacttttcctttcagAAGATACCATCCCACGAACACAGATAG
AAAGAAGGAAAACAAGCCTGTATTTTTCCAGCAAATATAACAAAGAAGgtatccctttcccaatca
gaacagcaaattctaattccatttgggttttcaattctgatgcactatgtttgtttagCTCTTAG
CCCCCCACGACGTAAAGCCTTTAAGAAATGGACACCTCCTCGGTCACCTTTTAATCTCGTTCAAGA
AACACTTTTTCATGATCCATGGAAGCTTCTCATCGCTACTATATTTCTCAATCGGACCTCAGgttt
ggggattattatcatctttgtcttagtagagacagtgtggtagggagaaagcactgaattgag
gcctgggttcaaagtcattttgagtgtgtcacctgggatagggcattccccctttcaccttaaac
tcttcacctatgaggaaaatggggg

Fig. 19E

Exon 6 ccagtgtttttgtttttgttttctttaaaaaaaaaaaaaaccctctggatgagatttctatga
gaaactacttgaacgtgaaatcagcccacctggagtcttgtaatcattcagttacttttacnttcc
cagGCAAAATGGCAATACCTGTGCTTTGGAAGTTTCTGGAGAAGTATCCTTCAGCTGAGGTAGCAA
GAACCGCAGACTGGAGAGATGTGTCAGAACTTCTTAAACCTCTTGGTCTCTACGATCTTCGGGCAA
AAACCATTGTCAAGTTCTCAGgtattttcctatacacccaaaggaaaaacataatacattgtgctt
atttaagagagccacaccttaaactttaatgttctcagatactatattaatggaggtttttca
gctcaagcatttaaaaaagtccacttttccccaaaccacagtctcccactgacctaaacaataaat
cttt

Fig. 19F

Exon 7 ctttagaagctgacctgataatgtgggatgttgtattcttcagATGAATACCTGACAAAGCAG
TGGAAGTATCCAATTGAGCTTCATGGGATTGGTAAATATGGCAACGACTCTTACCGAATTTTTGT
GTCAATGAGTGGAAGCAGgtgaggctcactcccatccataattcagcacatttggtctctgagg
caaaataagtccaccattatggttaagacnatttattggggatacaaatgctattacagtcacaa
caattgtgttcctggctgcggggaagcgngtggcatgtgggttttggggtttttgatcagtaggcg
ctcccagg

Fig. 19G

Exon 8 tgtgtgagattaccttaatataaggtataacttaaaatattcatgaatcccaggaggttaaaggtt
ataacttttaggtatggtatcgtaatgtactgtcccccagcaaacatttaaaaagccaatttt
aaaaaatgtatttctgactaagttacatntaaggtctctgcctctgtatcttatgtttcttccagG
TGCACCCTGAAGACCACAAATTAAATAAATATCATGACTGGCTTTCCCAAAATCATGAAAAATTAA
GTTTATCTTAAACTCTGCAGCTTTCAAGCTCATCTGTTATGCATAGCTTTGCACTTCAAAAAAGCT
TAATTAAGTACAACCAACCACCTTTCCAGCCATAGAGATTTTAATTAGCCCAACTAGAAGCCTAGT
GTGTGTGCTTTCTTAATGTGTGTGCCAATGGTGGATCTTTGCTACTGAATGTGTTTGAACATGTTT
TGAGATTTTTTTAAAATAAATTATTATTTGACAACA*atccaaaaaaaatacggcttttccaatga
tgaaatataatcagaagatgaaaaatagttctaaactatcaataatacaaagcaaatttctatca
gccttgctaaagctaggggcccactaaatatttt Please note: asterisk indicates the poly(A) addition site.

Fig. 19H

Complete sequence of the intron between exon 7 and exon 8.

GGAAGCAGgtgaggctcactcccatccataattcagcacatttggtctctgaggcaaaataagtcc
accattatggttaagactatttattggatacaaatgctattacagtcacaaacaattgtgttcctg
gctgcggggaagcgagtggcatgtgggttttggggttttgatcagtaagcgctcccaagtccaca
aagaccagtccagcggcgtggcctctgactcatctccagtggtttgtcacctctggccctgttcct
gtcattccctatttgtgtgctatctctaagcctgacgtggttttcctcctgtcaaaagtacaccac
tacaggaaagcaggaaggtttgggccttgcaatgtatgcatattgggtttctcttagtggtctcag
actacgtttgtggtgactgggtcctgcttcagccctgttgaatatgcccagcctgtggcatgctgg
tggtcatcctggcagctggtgggtggcctggtatgctgcccactcagcttgagactcaccctcatg
cattcagccagtaggtctggccaagcctgaactgaaggaccatggtcctatcccagcttcatcaca
gcaatccattgtgacctgagaatccatttaacctctcggtctagaacctccttctggaaagtgagg
tattaatacttgactcaatgttatcgccaccccacattctaagtcatggttgagtagtaatttgga
cagtaccttgtaaattgtgtgagattaccttaatataaggtataacttaaaatattcatgaatccc
aggaggttaaaggttataactttaggtatggtatcgtaatgtactgtcccccagcaaacatttaa
aaagccaattttaaaaaatgtatttctgactaagttacattaaggtctctgcctctgtatcttatg
tttcttccagGTGCACCC

* The asterisk indicates that the bottom oligonucleotide strand is radioactively labelled

*The asterisk indicates that the bottom oligonucleotide strand is radioactively labelled

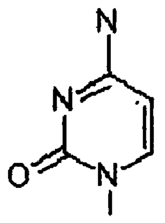
Cytosine
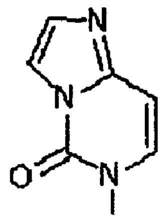
3, $N^4$-Ethenocytosine (E)
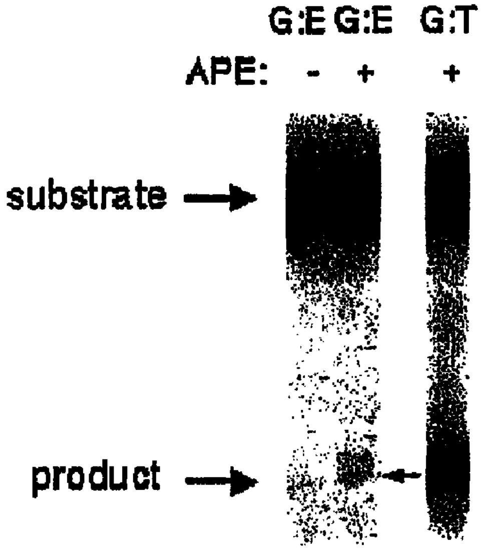
Fig. 29

1) Denature DNA fragments and mix with CT-SNP probe in order to generate heteroduplex 5'____CpG____3'  →  5'____CpG____3'   heteroduplex
3'____GpC____5'     3'____GpT____5'   with G:T mismatch allele 1 or

5'____CpA____3'  →  5'____CpA____3'   homoduplex
3'____GpT____5'     3'____GpT____5' allele 2

+

3'____GpT____5'
CT-SNP probe

2) Incubate annealed molecules with recombinant MED1 followed by NaOH in order to cleave heteroduplex ↓ + MED1   ↓
  + NaOH 5'____CpG____3'   or   5'____CpA____3'
3'____Gp  ____5'        3'____GpT____5' cleaved heteroduplex    uncleaved homoduplex

3) Separate fragments of the cleaved strand by standard techniques (e.g. by electrophoresis)

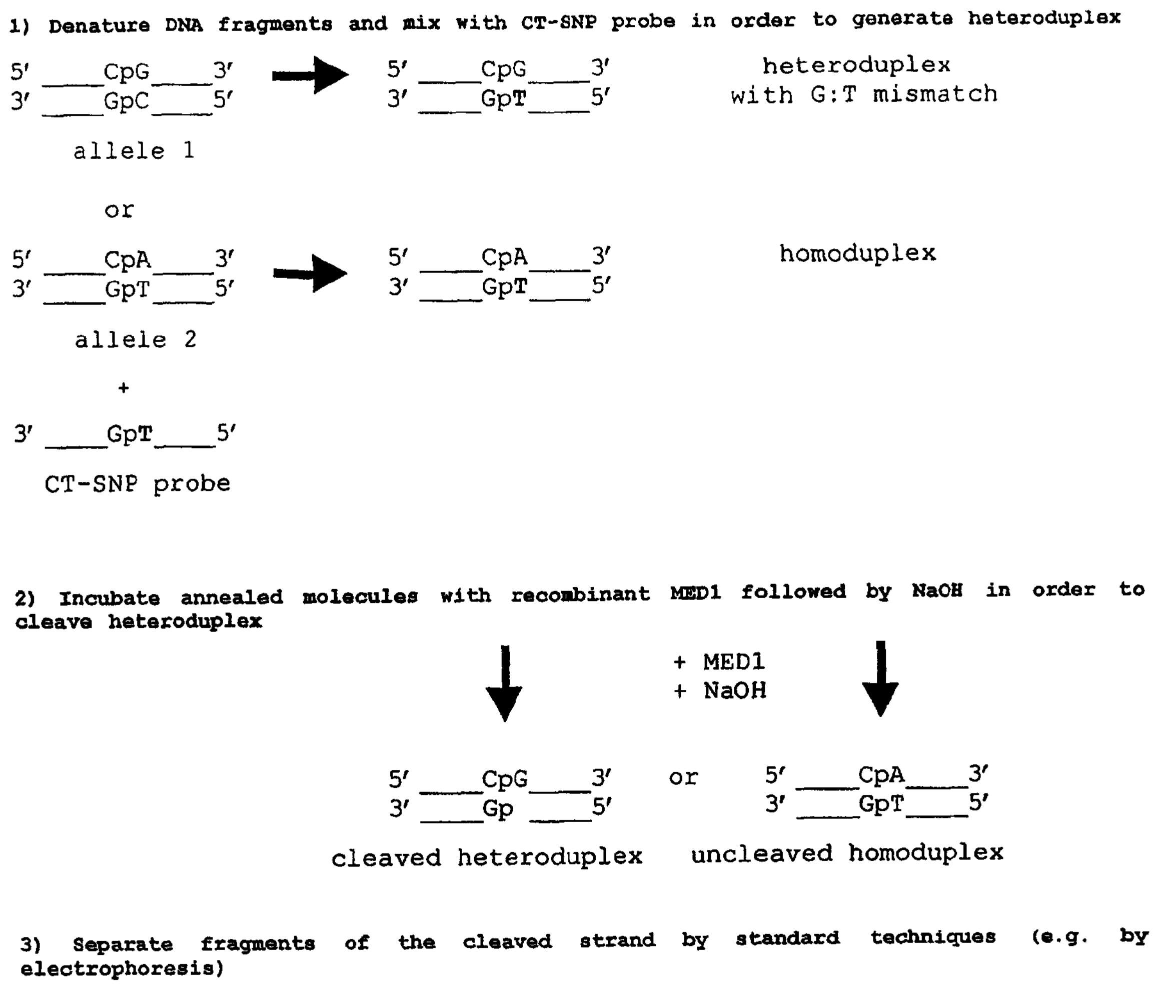

Fig. 30

SEQUENCE LISTING

<160> NUMBER OF SEQ ID NOS: 73

<210> SEQ ID NO 1
<211> LENGTH: 2152
<212> TYPE: DNA
<213> ORGANISM: Homo sapiens

<400> SEQUENCE: 1

```
ggcggcgtct ggggcgcttt cgcaacattc agacctcggt tgcagcccgg tgccgtgagc     60
tgaagaggtt tcacatctta ctccgcccca caccctgggc gttgcggcgc tgggctcgtt    120
gctgcagccg gaccctgctc gatgggcacg actgggctgg agagtctgag tctgggggac    180
cgcggagctg cccccaccgt cacctctagt gagcgcctag tcccagaccc gccgaatgac    240
ctccgcaaag aagatgttgc tatggaattg gaaagagtgg gagaagatga ggaacaaatg    300
atgataaaaa gaagcagtga atgtaatccc ttgctacaag aacccatcgc ttctgctcag    360
tttggtgcta ctgcaggaac agaatgccgt aagtctgtcc catgtggatg ggaaagagtt    420
gtgaagcaaa ggttatttgg gaagacagca ggaagatttg atgtgtactt tatcagccca    480
caaggactga agttcagatc caaaagttca cttgctaatt atcttcacaa aaatggagag    540
acttctctta agccagaaga ttttgatttt actgtacttt ctaaaagggg tatcaagtca    600
agatataaag actgcagcat ggcagccctg acatcccatc tacaaaacca aagtaacaat    660
tcaaactgga acctcaggac ccgaagcaag tgcaaaaagg atgtgtttat gccgccaagt    720
agtagttcag agttgcagga gagcagagga ctctctaact ttacttccac tcatttgctt    780
ttgaaagaag atgagggtgt tgatgatgtt aacttcagaa aggttagaaa gcccaaagga    840
aaggtgacta ttttgaaagg aatcccaatt aagaaaacta aaaaaggatg taggaagagc    900
tgttcaggtt ttgttcaaag tgatagcaaa agagaatctg tgtgtaataa agcagatgct    960
gaaagtgaac ctgttgcaca aaaaagtcag cttgatagaa ctgtctgcat ttctgatgct   1020
ggagcatgtg gtgagaccct cagtgtgacc agtgaagaaa acagccttgt aaaaaaaaaa   1080
gaaagatcat tgagttcagg atcaaatttt tgttctgaac aaaaaacttc tggcatcata   1140
aacaaatttt gttcagccaa agactcagaa cacaacgaga agtatgagga taccttttta   1200
gaatctgaag aaatcggaac aaaagtagaa gttgtggaaa ggaaagaaca tttgcatact   1260
gacattttaa aacgtggctc tgaaatggac aacaactgct caccaaccag gaaagacttc   1320
actggtgaga aaatatttca agaagatacc atcccacgaa cacagataga aagaaggaaa   1380
acaagcctgt atttttccag caaatataac aaagaagctc ttagcccccc acgacgtaaa   1440
gcctttaaga aatggacacc tcctcggtca ccttttaatc tcgttcaaga aacacttttt   1500
catgatccat ggaagcttct catcgctact atatttctca atcggacctc aggcaaaatg   1560
gcaatacctg tgctttggaa gtttctggag aagtatcctt cagctgaggt agcaagaacc   1620
gcagactgga gagatgtgtc agaacttctt aaacctcttg gtctctacga tcttcgggca   1680
aaaaccattg tcaagttctc agatgaatac ctgacaaagc agtggaagta tccaattgag   1740
cttcatggga ttggtaaata tggcaacgac tcttaccgaa ttttttgtgt caatgagtgg   1800
aagcaggtgc accctgaaga ccacaaatta aataaatatc atgactggct ttgggaaaat   1860
catgaaaaat taagtttatc ttaaactctg cagctttcaa gctcatctgt tatgcatagc   1920
tttgcacttc aaaaaagctt aattaagtac aaccaaccac ctttccagcc atagagattt   1980
taattagccc aactagaagc ctagtgtgtg tgctttctta atgtgtgtgc caatggtgga   2040
```

-continued tctttgctac tgaatgtgtt tgaacatgtt ttgagatttt tttaaaataa attattattt 2100
gacaacaaaa aaaaaaaaaa aaaaaaaaaa aaaaaaaaaa aaaaaaaaaa aa 2152

<210> SEQ ID NO 2
<211> LENGTH: 580
<212> TYPE: PRT
<213> ORGANISM: Homo sapiens

<400> SEQUENCE: 2

```
Met Gly Thr Thr Gly Leu Glu Ser Leu Ser Leu Gly Asp Arg Gly Ala
 1               5                  10                  15

Ala Pro Thr Val Thr Ser Ser Glu Arg Leu Val Pro Asp Pro Pro Asn
            20                  25                  30

Asp Leu Arg Lys Glu Asp Val Ala Met Glu Leu Glu Arg Val Gly Glu
        35                  40                  45

Asp Glu Glu Gln Met Met Ile Lys Arg Ser Ser Glu Cys Asn Pro Leu
    50                  55                  60

Leu Gln Glu Pro Ile Ala Ser Ala Gln Phe Gly Ala Thr Ala Gly Thr
65                  70                  75                  80

Glu Cys Arg Lys Ser Val Pro Cys Gly Trp Glu Arg Val Val Lys Gln
                85                  90                  95

Arg Leu Phe Gly Lys Thr Ala Gly Arg Phe Asp Val Tyr Phe Ile Ser
            100                 105                 110

Pro Gln Gly Leu Lys Phe Arg Ser Lys Ser Ser Leu Ala Asn Tyr Leu
        115                 120                 125

His Lys Asn Gly Glu Thr Ser Leu Lys Pro Glu Asp Phe Asp Phe Thr
    130                 135                 140

Val Leu Ser Lys Arg Gly Ile Lys Ser Arg Tyr Lys Asp Cys Ser Met
145                 150                 155                 160

Ala Ala Leu Thr Ser His Leu Gln Asn Gln Ser Asn Asn Ser Asn Trp
                165                 170                 175

Asn Leu Arg Thr Arg Ser Lys Cys Lys Lys Asp Val Phe Met Pro Pro
            180                 185                 190

Ser Ser Ser Ser Glu Leu Gln Glu Ser Arg Gly Leu Ser Asn Phe Thr
        195                 200                 205

Ser Thr His Leu Leu Leu Lys Glu Asp Glu Gly Val Asp Asp Val Asn
    210                 215                 220

Phe Arg Lys Val Arg Lys Pro Lys Gly Lys Val Thr Ile Leu Lys Gly
225                 230                 235                 240

Ile Pro Ile Lys Lys Thr Lys Lys Gly Cys Arg Lys Ser Cys Ser Gly
                245                 250                 255

Phe Val Gln Ser Asp Ser Lys Arg Glu Ser Val Cys Asn Lys Ala Asp
            260                 265                 270

Ala Glu Ser Glu Pro Val Ala Gln Lys Ser Gln Leu Asp Arg Thr Val
        275                 280                 285

Cys Ile Ser Asp Ala Gly Ala Cys Gly Glu Thr Leu Ser Val Thr Ser
    290                 295                 300

Glu Glu Asn Ser Leu Val Lys Lys Lys Glu Arg Ser Leu Ser Ser Gly
305                 310                 315                 320

Ser Asn Phe Cys Ser Glu Gln Lys Thr Ser Gly Ile Ile Asn Lys Phe
                325                 330                 335

Cys Ser Ala Lys Asp Ser Glu His Asn Glu Lys Tyr Glu Asp Thr Phe
            340                 345                 350
```

-continued

```
Leu Glu Ser Glu Glu Ile Gly Thr Lys Val Glu Val Val Glu Arg Lys
        355                 360                 365

Glu His Leu His Thr Asp Ile Leu Lys Arg Gly Ser Glu Met Asp Asn
    370                 375                 380

Asn Cys Ser Pro Thr Arg Lys Asp Phe Thr Gly Glu Lys Ile Phe Gln
385                 390                 395                 400

Glu Asp Thr Ile Pro Arg Thr Gln Ile Glu Arg Arg Lys Thr Ser Leu
                405                 410                 415

Tyr Phe Ser Ser Lys Tyr Asn Lys Glu Ala Leu Ser Pro Pro Arg Arg
            420                 425                 430

Lys Ala Phe Lys Lys Trp Thr Pro Pro Arg Ser Pro Phe Asn Leu Val
        435                 440                 445

Gln Glu Thr Leu Phe His Asp Pro Trp Lys Leu Leu Ile Ala Thr Ile
    450                 455                 460

Phe Leu Asn Arg Thr Ser Gly Lys Met Ala Ile Pro Val Leu Trp Lys
465                 470                 475                 480

Phe Leu Glu Lys Tyr Pro Ser Ala Glu Val Ala Arg Thr Ala Asp Trp
                485                 490                 495

Arg Asp Val Ser Glu Leu Leu Lys Pro Leu Gly Leu Tyr Asp Leu Arg
            500                 505                 510

Ala Lys Thr Ile Val Lys Phe Ser Asp Glu Tyr Leu Thr Lys Gln Trp
        515                 520                 525

Lys Tyr Pro Ile Glu Leu His Gly Ile Gly Lys Tyr Gly Asn Asp Ser
    530                 535                 540

Tyr Arg Ile Phe Cys Val Asn Glu Trp Lys Gln Val His Pro Glu Asp
545                 550                 555                 560

His Lys Leu Asn Lys Tyr His Asp Trp Leu Trp Glu Asn His Glu Lys
                565                 570                 575

Leu Ser Leu Ser
            580


<210> SEQ ID NO 3
<211> LENGTH: 46
<212> TYPE: DNA
<213> ORGANISM: Artificial Sequence
<220> FEATURE:
<223> OTHER INFORMATION: mobility shift assay oligonucleotide
<220> FEATURE:
<221> NAME/KEY: misc_feature
<222> LOCATION: 9, 16, 22, 30, 37
<223> OTHER INFORMATION: n = methylcytosine

<400> SEQUENCE: 3

gcgaattcng tgcgangaag cnggacgatn gaccagngct cgagca                    46


<210> SEQ ID NO 4
<211> LENGTH: 46
<212> TYPE: DNA
<213> ORGANISM: Artificial Sequence
<220> FEATURE:
<223> OTHER INFORMATION: mobility shift assay oligonucleotide
<220> FEATURE:
<221> NAME/KEY: misc_feature
<222> LOCATION: 10, 17, 25, 31, 38
<223> OTHER INFORMATION: n = methylcytosine

<400> SEQUENCE: 4

gtgctcgagn gctggtngat cgtcnggctt ngtcgcangg aattcg                    46


<210> SEQ ID NO 5
```

-continued

<211> LENGTH: 1514
<212> TYPE: DNA
<213> ORGANISM: Mus musculus

<400> SEQUENCE: 5
caaggaagat attgctgttg gactgggagg agtgggagaa gatggaaagg acctggtgat 60
aagcagtgag cgcagctccc ttctccaaga gcccactgct tctactctgt ctagtactac 120
agcgacagaa ggccacaagc ctgtcccgtg tggatgggaa agagttgtga agcaaaggtt 180
atctgggaaa actgcaggaa aatttgatgt atactttatc agcccacaag gattgaagtt 240
caggatcaaa acgttcactt gctaattatc ttctcaaaaa tggggagact tttcttaagc 300
ctgaagattt taattttact gtactgccga aagggagcat caatcccggt tataaacacc 360
aaagtttggc agctctgact tccctgcagc caaatgaaac tgacgtttca aagcagaacc 420
tcaagacacg aagcaagtgg aaaacagatg tgttgcctct gcccagtggt acttcagagt 480
cgccagaaag cagcggactg tctaactcta actcggcttg cttgctattg agagaacata 540
gggacattca ggatgttgac tctgagaaga ggagaaagtc caaaagaaag gtgactgttt 600
tgaaaggaac tgcaagtcag aaaaccaaac aaaagtgcag gaagagtctc ttagagtcta 660
ctcaaagaaa cagaaaaaga gcatctgtgg ttcagaaggt gggtgctgat cgcgagctgg 720
tgccacagga aagtcaactc aacagaaccc tctgccctgc agatgcctgt gcaagggaga 780
ctgttggcct ggctggggaa gaaaaatcac caagcccagg actggatctt tgtttcatac 840
aagtaacttc tggcaccaca aacaaattcc attcaactga agcagcaggt gaagcaaatc 900
gtgagcagac ttttttagaa tcagaggaaa tcagatcgaa gggagacaga aagggggagg 960
cacatttgca tactggtgtt ttacaggatg gctctgaaat gcccagctgc tcacaagcca 1020
agaaacactt tacttctgag acatttcaag aagacagcat cccacggaca caagtagaaa 1080
aaaggaaaac aagcctgtat ttttccagca agtacaacaa agaagctctt agccccccaa 1140
gacgcaaatc cttcaagaaa tggacccctc ctcggtcacc ttttaatctt gttcaagaaa 1200
tacttttcca tgacccatgg aagctcctca tcgcgactat atttctcaat cggacctcag 1260
gcaagatggc catccctgtg ctgtgggagt ttctagagaa gtacccttca gctgaagtgg 1320
cccgagctgc cgactggagg gacgtgtcgg agcttctcaa gcctcttggt ctctacgatc 1380
tccgtgcaaa aacattatca agttctcaga tgaatatctg acaaagcagt ggaggtatcc 1440
gattgagctt catgggattt ggttaaaata tggcaacgac tctaccggat cttttgtgtc 1500
aatgaatgga acag 1514

<210> SEQ ID NO 6
<211> LENGTH: 19
<212> TYPE: DNA
<213> ORGANISM: Artificial Sequence
<220> FEATURE:
<223> OTHER INFORMATION: PCR primer

<400> SEQUENCE: 6
gtctggggcg ctttcgcaa 19

<210> SEQ ID NO 7
<211> LENGTH: 22
<212> TYPE: DNA
<213> ORGANISM: Artificial Sequence
<220> FEATURE:
<223> OTHER INFORMATION: PCR primer

<400> SEQUENCE: 7

-continued ccacacactg tccactctcc cg 22

<210> SEQ ID NO 8
<211> LENGTH: 21
<212> TYPE: DNA
<213> ORGANISM: Artificial Sequence
<220> FEATURE:
<223> OTHER INFORMATION: PCR primer

<400> SEQUENCE: 8
actcccatag cacaagactg g 21

<210> SEQ ID NO 9
<211> LENGTH: 20
<212> TYPE: DNA
<213> ORGANISM: Artificial Sequence
<220> FEATURE:
<223> OTHER INFORMATION: PCR primer

<400> SEQUENCE: 9
gctatgctcc cactacctgc 20

<210> SEQ ID NO 10
<211> LENGTH: 21
<212> TYPE: DNA
<213> ORGANISM: Artificial Sequence
<220> FEATURE:
<223> OTHER INFORMATION: PCR primer

<400> SEQUENCE: 10
cccttctatt tactagcagt a 21

<210> SEQ ID NO 11
<211> LENGTH: 21
<212> TYPE: DNA
<213> ORGANISM: Artificial Sequence
<220> FEATURE:
<223> OTHER INFORMATION: PCR primer

<400> SEQUENCE: 11
gatgcagcat ataaatttct c 21

<210> SEQ ID NO 12
<211> LENGTH: 21
<212> TYPE: DNA
<213> ORGANISM: Artificial Sequence
<220> FEATURE:
<223> OTHER INFORMATION: PCR primer

<400> SEQUENCE: 12
tgcatccctc aatattgctt t 21

<210> SEQ ID NO 13
<211> LENGTH: 21
<212> TYPE: DNA
<213> ORGANISM: Artificial Sequence
<220> FEATURE:
<223> OTHER INFORMATION: PCR primer

<400> SEQUENCE: 13
tcaattcagt gctttctccc t 21

<210> SEQ ID NO 14
<211> LENGTH: 21
<212> TYPE: DNA

-continued

<213> ORGANISM: Artificial Sequence
<220> FEATURE:
<223> OTHER INFORMATION: PCR primer

<400> SEQUENCE: 14
agcccacctg gagtcttgta a 21

<210> SEQ ID NO 15
<211> LENGTH: 21
<212> TYPE: DNA
<213> ORGANISM: Artificial Sequence
<220> FEATURE:
<223> OTHER INFORMATION: PCR primer

<400> SEQUENCE: 15
aaagtttaag gtgtggctct c 21

<210> SEQ ID NO 16
<211> LENGTH: 21
<212> TYPE: DNA
<213> ORGANISM: Artificial Sequence
<220> FEATURE:
<223> OTHER INFORMATION: PCR primer

<400> SEQUENCE: 16
gaagctgacc tgataatgtg g 21

<210> SEQ ID NO 17
<211> LENGTH: 21
<212> TYPE: DNA
<213> ORGANISM: Artificial Sequence
<220> FEATURE:
<223> OTHER INFORMATION: PCR primer

<400> SEQUENCE: 17
cttattttgc ctcagagacc a 21

<210> SEQ ID NO 18
<211> LENGTH: 21
<212> TYPE: DNA
<213> ORGANISM: Artificial Sequence
<220> FEATURE:
<223> OTHER INFORMATION: PCR primer

<400> SEQUENCE: 18
tatcgtaatg tactgtcccc c 21

<210> SEQ ID NO 19
<211> LENGTH: 21
<212> TYPE: DNA
<213> ORGANISM: Artificial Sequence
<220> FEATURE:
<223> OTHER INFORMATION: PCR primer

<400> SEQUENCE: 19
gctttagcaa ggctgataga a 21

<210> SEQ ID NO 20
<211> LENGTH: 21
<212> TYPE: DNA
<213> ORGANISM: Artificial Sequence
<220> FEATURE:
<223> OTHER INFORMATION: PCR primer

<400> SEQUENCE: 20
caaatcttcc tgctgtcttc c 21

-continued

<210> SEQ ID NO 21
<211> LENGTH: 261
<212> TYPE: DNA
<213> ORGANISM: Mus musculus

<400> SEQUENCE: 21

```
ggttttgttt ttccagcaag gaagatattg ctgttggact gggaggagtg ggagaagatg     60

gaaaggacct ggtgataagc agtgagcgca gctcccttct ccaagagccc actgcttcta    120

ctctgtctag tactacagcg acagaaggcc acaagcctgt cccgtgtgga tgggaaagag    180

ttgtgaagca aaggttatct gggaaaactg caggaaaatt tgatgtatac tttatcaggt    240

aagcatttag gaaggaaaat a                                              261
```

<210> SEQ ID NO 22
<211> LENGTH: 419
<212> TYPE: DNA
<213> ORGANISM: Homo sapiens
<220> FEATURE:
<221> NAME/KEY: misc_feature
<222> LOCATION: 352
<223> OTHER INFORMATION: n = a, t, c, or g

<400> SEQUENCE: 22

```
gcggcggcgt ctggggcgct ttcgcaacat tcagacctcg gttgcagccc ggtgccgtga     60

gctgaagagg tttcacatct tactccgccc cacaccctgg gcgttgcggc gctgggctcg    120

ttgctgcagc cggaccctgc tcgatgggca cgactgggct ggagagtctg agtctggggg    180

accgcggagc tgcccccacc gtcacctcta gtgagcgcct agtcccagac ccgccgaatg    240

acctccggta agttactgtc cccttttggg cctcagtttc accacctgta aaatggtatc    300

gggagagtgg acagtgtgtg ggcctttcta acctttgaca gagggtcggc anaaacctcg    360

aagcccacgg gtttagttac tagggtctgg agcccaggtg ctcttcctgt gcgatcagc     419
```

<210> SEQ ID NO 23
<211> LENGTH: 2134
<212> TYPE: DNA
<213> ORGANISM: Homo sapiens

<400> SEQUENCE: 23

```
ggcggcgtct ggggcgcttt cgcaacattc agacctcggt tgcagcccgg tgccgtgagc     60

tgaagaggtt tcacatctta ctccgcccca caccctgggc gttgcggcgc tgggctcgtt    120

gctgcagccg gaccctgctc gatgggcacg actgggctgg agagtctgag tctgggggac    180

cgcggagctg cccccaccgt cacctctagt gagcgcctag tcccagaccc gccgaatgac    240

ctccgcaaag aagatgttgc tatggaattg gaaagagtgg gagaagatga ggaacaaatg    300

atgataaaaa gaagcagtga atgtaatccc ttgctacaag aacccatcgc ttctgctcag    360

tttggtgcta ctgcaggaac agaatgccgt aagtctgtcc catgtggatg ggaaagagtt    420

gtgaagcaaa ggttatttgg gaagacagca ggaagatttg atgtgtactt tatcagccca    480

caaggactga agttcagatc caaaagttca cttgctaatt atcttcacaa aaatggagag    540

acttctctta agccagaaga ttttgatttt actgtacttt ctaaaagggg tatcaagtca    600

agatataaag actgcagcat ggcagccctg acatcccatc tacaaaacca aagtaacaat    660

tcaaactgga acctcaggac ccgaagcaag tgcaaaaagg atgtgtttat gccgccaagt    720

agtagttcag agttgcagga gagcagagga ctctctaact ttacttccac tcatttgctt    780
```

-continued

```
ttgaaagaag atgagggtgt tgatgatgtt aacttcagaa aggttagaaa gcccaaagga    840

aaggtgacta ttttgaaagg aatcccaatt aagaaaacta aaaaaggatg taggaagagc    900

tgttcaggtt ttgttcaaag tgatagcaaa agagaatctg tgtgtaataa agcagatgct    960

gaaagtgaac ctgttgcaca aaaaagtcag cttgatagaa ctgtctgcat ttctgatgct   1020

ggagcatgtg gtgagaccct cagtgtgacc agtgaagaaa acagccttgt aaaaaaaaaa   1080

gaaagatcat tgagttcagg atcaaatttt tgttctgaac aaaaaacttc tggcatcata   1140

aacaaatttt gttcagccaa agactcagaa cacaacgaga agtatgagga taccttttta   1200

gaatctgaag aaatcggaac aaaagtagaa gttgtggaaa ggaaagaaca tttgcatact   1260

gacattttaa aacgtggctc tgaaatggac aacaactgct caccaaccag gaaagacttc   1320

actgaagata ccatcccacg aacacagata gaaagaagga aaacaagcct gtatttttcc   1380

agcaaatata acaaagaagc tcttagcccc ccacgacgta aagcctttaa gaaatggaca   1440

cctcctcggt caccttttaa tctcgttcaa gaaacacttt ttcatgatcc atggaagctt   1500

ctcatcgcta ctatatttct caatcggacc tcaggcaaaa tggcaatacc tgtgctttgg   1560

aagtttctgg agaagtatcc ttcagctgag gtagcaagaa ccgcagactg gagagatgtg   1620

tcagaacttc ttaaacctct tggtctctac gatcttcggg caaaaaccat tgtcaagttc   1680

tcagatgaat acctgacaaa gcagtggaag tatccaattg agcttcatgg gattggtaaa   1740

tatggcaacg actcttaccg aatttttgt gtcaatgagt ggaagcaggt gcaccctgaa   1800

gaccacaaat taaataaata tcatgactgg ctttgggaaa atcatgaaaa attaagttta   1860

tcttaaactc tgcagctttc aagctcatct gttatgcata gctttgcact tcaaaaaagc   1920

ttaattaagt acaaccaacc acctttccag ccatagagat tttaattagc ccaactagaa   1980

gcctagtgtg tgtgctttct taatgtgtgt gccaatggtg gatctttgct actgaatgtg   2040

tttgaacatg ttttgagatt tttttaaaat aaattattat ttgacaacaa aaaaaaaaaa   2100

aaaaaaaaaa aaaaaaaaaa aaaaaaaaaa aaaa                               2134
```

<210> SEQ ID NO 24
<211> LENGTH: 574
<212> TYPE: PRT
<213> ORGANISM: Homo sapiens

<400> SEQUENCE: 24

```
Met Gly Thr Thr Gly Leu Glu Ser Leu Ser Leu Gly Asp Arg Gly Ala
 1               5                  10                  15

Ala Pro Thr Val Thr Ser Ser Glu Arg Leu Val Pro Asp Pro Pro Asn
            20                  25                  30

Asp Leu Arg Lys Glu Asp Val Ala Met Glu Leu Glu Arg Val Gly Glu
        35                  40                  45

Asp Glu Glu Gln Met Met Ile Lys Arg Ser Ser Glu Cys Asn Pro Leu
    50                  55                  60

Leu Gln Glu Pro Ile Ala Ser Ala Gln Phe Gly Ala Thr Ala Gly Thr
65                  70                  75                  80

Glu Cys Arg Lys Ser Val Pro Cys Gly Trp Glu Arg Val Val Lys Gln
                85                  90                  95

Arg Leu Phe Gly Lys Thr Ala Gly Arg Phe Asp Val Tyr Phe Ile Ser
            100                 105                 110

Pro Gln Gly Leu Lys Phe Arg Ser Lys Ser Ser Leu Ala Asn Tyr Leu
        115                 120                 125

His Lys Asn Gly Glu Thr Ser Leu Lys Pro Glu Asp Phe Asp Phe Thr
```

-continued

```
    130                 135                 140

Val Leu Ser Lys Arg Gly Ile Lys Ser Arg Tyr Lys Asp Cys Ser Met
145                 150                 155                 160

Ala Ala Leu Thr Ser His Leu Gln Asn Gln Ser Asn Asn Ser Asn Trp
                165                 170                 175

Asn Leu Arg Thr Arg Ser Lys Cys Lys Lys Asp Val Phe Met Pro Pro
            180                 185                 190

Ser Ser Ser Ser Glu Leu Gln Glu Ser Arg Gly Leu Ser Asn Phe Thr
        195                 200                 205

Ser Thr His Leu Leu Leu Lys Glu Asp Glu Gly Val Asp Asp Val Asn
    210                 215                 220

Phe Arg Lys Val Arg Lys Pro Lys Gly Lys Val Thr Ile Leu Lys Gly
225                 230                 235                 240

Ile Pro Ile Lys Lys Thr Lys Lys Gly Cys Arg Lys Ser Cys Ser Gly
                245                 250                 255

Phe Val Gln Ser Asp Ser Lys Arg Glu Ser Val Cys Asn Lys Ala Asp
            260                 265                 270

Ala Glu Ser Glu Pro Val Ala Gln Lys Ser Gln Leu Asp Arg Thr Val
        275                 280                 285

Cys Ile Ser Asp Ala Gly Ala Cys Gly Glu Thr Leu Ser Val Thr Ser
    290                 295                 300

Glu Glu Asn Ser Leu Val Lys Lys Lys Glu Arg Ser Leu Ser Ser Gly
305                 310                 315                 320

Ser Asn Phe Cys Ser Glu Gln Lys Thr Ser Gly Ile Ile Asn Lys Phe
                325                 330                 335

Cys Ser Ala Lys Asp Ser Glu His Asn Glu Lys Tyr Glu Asp Thr Phe
            340                 345                 350

Leu Glu Ser Glu Glu Ile Gly Thr Lys Val Glu Val Val Glu Arg Lys
        355                 360                 365

Glu His Leu His Thr Asp Ile Leu Lys Arg Gly Ser Glu Met Asp Asn
    370                 375                 380

Asn Cys Ser Pro Thr Arg Lys Asp Phe Thr Glu Asp Thr Ile Pro Arg
385                 390                 395                 400

Thr Gln Ile Glu Arg Arg Lys Thr Ser Leu Tyr Phe Ser Ser Lys Tyr
                405                 410                 415

Asn Lys Glu Ala Leu Ser Pro Pro Arg Arg Lys Ala Phe Lys Lys Trp
            420                 425                 430

Thr Pro Pro Arg Ser Pro Phe Asn Leu Val Gln Glu Thr Leu Phe His
        435                 440                 445

Asp Pro Trp Lys Leu Leu Ile Ala Thr Ile Phe Leu Asn Arg Thr Ser
    450                 455                 460

Gly Lys Met Ala Ile Pro Val Leu Trp Lys Phe Leu Glu Lys Tyr Pro
465                 470                 475                 480

Ser Ala Glu Val Ala Arg Thr Ala Asp Trp Arg Asp Val Ser Glu Leu
                485                 490                 495

Leu Lys Pro Leu Gly Leu Tyr Asp Leu Arg Ala Lys Thr Ile Val Lys
            500                 505                 510

Phe Ser Asp Glu Tyr Leu Thr Lys Gln Trp Lys Tyr Pro Ile Glu Leu
        515                 520                 525

His Gly Ile Gly Lys Tyr Gly Asn Asp Ser Tyr Arg Ile Phe Cys Val
    530                 535                 540

Asn Glu Trp Lys Gln Val His Pro Glu Asp His Lys Leu Asn Lys Tyr
545                 550                 555                 560
```

-continued

```
His Asp Trp Leu Trp Glu Asn His Glu Lys Leu Ser Leu Ser
                565                 570


<210> SEQ ID NO 25
<211> LENGTH: 2152
<212> TYPE: DNA
<213> ORGANISM: Homo sapiens

<400> SEQUENCE: 25

ggcggcgtct ggggcgcttt cgcaacattc agacctcggt tgcagcccgg tgccgtgagc      60

tgaagaggtt tcacatctta ctccgcccca caccctgggc gttgcggcgc tgggctcgtt     120

gctgcagccg gaccctgctc gatgggcacg actgggctgg agagtctgag tctgggggac     180

cgcggagctg cccccaccgt cacctctagt gagcgcctag tcccagaccc gccgaatgac     240

ctccgcaaag aagatgttgc tatggaattg gaaagagtgg gagaagatga ggaacaaatg     300

atgataaaaa gaagcagtga atgtaatccc ttgctacaag aacccatcgc ttctgctcag     360

tttggtgcta ctgcaggaac agaatgccgt aagtctgtcc catgtggatg ggaaagagtt     420

gtgaagcaaa ggttatttgg gaagacagca ggaagatttg atgtgtactt tatcagccca     480

caaggactga agttcagatc caaaagttca cttgctaatt atcttcacaa aaatggagag     540

acttctctta agccagaaga ttttgatttt actgtacttt ctaaaagggg tatcaagtca     600

agatataaag actgcagcat ggcagccctg acatcccatc tacaaaacca aagtaacaat     660

tcaaactgga acctcaggac ccgaagcaag tgcaaaaagg atgtgtttat gccgccaagt     720

agtagttcag agttgcagga gagcagagga ctctctaact ttacttccac tcatttgctt     780

ttgaaagaag atgagggtgt tgatgatgtt aacttcagaa aggttagaaa gcccaaagga     840

aaggtgacta ttttgaaagg aatcccaatt aagaaaacta aaaaaggatg taggaagagc     900

tgttcaggtt ttgttcaaag tgatagcaaa agagaatctg tgtgtaataa agcagatgct     960

gaaagtgaac ctgttgcaca aaaaagtcag cttgatagaa ctgtctgcat ttctgatgct    1020

ggagcatgtg gtgagaccct cagtgtgacc agtgaagaaa acagccttgt aaaaaaaaaa    1080

gaaagatcat tgagttcagg atcaaatttt tgttctgaac aaaaaacttc tggcatcata    1140

aacaaatttt gttcagccaa agactcagaa cacaacgaga agtatgagga taccttttta    1200

gaatctgaag aaatcggaac aaaagtagaa gttgtggaaa ggaaagaaca tttgcatact    1260

gacattttaa aacgtggctc tgaaatggac aacaactgct caccaaccag gaaagacttc    1320

actggtgaga aaatatttca agaagatacc atcccacgaa cacagataga aagaaggaaa    1380

acaagcctgt atttttccag caaatataac aaagaagctc ttagcccccc acgacgtaaa    1440

gcctttaaga aatggacacc tcctcggtca cctttttaatc tcgttcaaga aacacttttt    1500

catgatccat ggaagcttct catcgctact atatttctca atcggacctc aggcaaaatg    1560

gcaatacctg tgctttggaa gtttctggag aagtatcctt cagctgaggt agcaagaacc    1620

gcagactgga gagatgtgtc agaacttctt aaacctcttg gtctctacga tcttcgggca    1680

aaaaccattg tcaagttctc agatgaatac ctgacaaagc agtggaagta tccaattgag    1740

cttcatggga ttggtaaata tggcaacgac tcttaccgaa tttttgtgt caatgagtgg    1800

aagcaggtgc accctgaaga ccacaaatta aataaatatc atgactggct ttgggaaaat    1860

catgaaaaat taagtctatc ttaaactctg cagctttcaa gctcatctgt tatgcatagc    1920

tttgcacttc aaaaaagctt aattaagtac aaccaaccac ctttccagcc atagagattt    1980

taattagccc aactagaagc ctagtgtgtg tgctttctta atgtgtgtgc caatggtgga    2040
```

-continued

```
tctttgctac tgaatgtgtt tgaacatgtt ttgagatttt tttaaaataa attattattt   2100

gacaacaaaa aaaaaaaaaa aaaaaaaaaa aaaaaaaaaa aaaaaaaaaa aa           2152
```

<210> SEQ ID NO 26
<211> LENGTH: 2152
<212> TYPE: DNA
<213> ORGANISM: Homo sapiens

<400> SEQUENCE: 26

```
ggcggcgtct ggggcgcttt cgcaacattc agacctcggt tgcagcccgg tgccgtgagc     60

tgaagaggtt tcacatctta ctccgcccca caccctgggc gttgcggcgc tgggctcgtt    120

gctgcagccg gaccctgctc gatgggcacg actgggctgg agagtctgag tctgggggac    180

cgcggagctg cccccaccgt cacctctagt gagcgcctag tcccagaccc gccgaatgac    240

ctccgcaaag aagatgttgc tatggaattg gaaagagtgg gagaagatga ggaacaaatg    300

atgataaaaa gaagcagtga atgtaatccc ttgctacaag aacccatcgc ttctgctcag    360

tttggtgcta ctgcaggaac agaatgccgt aagtctgtcc catgtggatg ggaaagagtt    420

gtgaagcaaa ggttatttgg gaagacagca ggaagatttg atgtgtactt tatcagccca    480

caaggactga agttcagatc caaaagttca cttgctaatt atcttcacaa aaatggagag    540

acttctctta agccagaaga ttttgatttt actgtacttt ctaaaagggg tatcaagtca    600

agatataaag actgcagcat ggcagccctg acatcccatc tacaaaacca aagtaacaat    660

tcaaactgga acctcaggac ccgaagcaag tgcaaaaagg atgtgtttat gccgccaagt    720

agtagttcag agttgcagga gagcagagga ctctctaact ttacttccac tcatttgctt    780

ttgaaagaag atgagggtgt tgatgatgtt aacttcagaa aggttagaaa gcccaaagga    840

aaggtgacta ttttgaaagg aatcccaatt aagaaaacta aaaaaggatg taggaagagc    900

tgttcaggtt ttgttcaaag tgatagcaaa agagaatctg tgtgtaataa agcagatgct    960

gaaagtgaac ctgttgcaca aaaaagtcag cttgatagaa ctgtctgcat ttctgatgct   1020

ggagcatgtg gtgagaccct cagtgtgacc agtgaagaaa acagccttgt aaaaaaaaaa   1080

gaaagatcat tgagttcagg atcaaatttt tgttctgaac aaaaaacttc tggcatcata   1140

aacaaatttt gttcagccaa agactcagaa cacaacgaga agtatgagga tacctttttta   1200

gaatctgaag aaatcggaac aaaagtagaa gttgtggaaa ggaaagaaca tttgcatact   1260

gacattttaa aacgtggctc tgaaatggac aacaactgct caccaaccag gaaagacttc   1320

actggtgaga aaatatttca agaagatacc atcccacgaa cacagataga aagaaggaaa   1380

acaagcctgt atttttccag caaatataac aaagaagctc ttagcccccc acgacgtaaa   1440

gcctttaaga aatggacacc tcctcggtca ccttttaatc tcgttcaaga aacacttttt   1500

catgatccat ggaagcttct catcgctact atatttctca atcggacctc aggcaaaatg   1560

gcaatacctg tgctttggaa gtttctggag aagtatcctt cagctgaggt agcaagaacc   1620

gcagactgga gagatgtgtc agaacttctt aaacctcttg gtctctacga tcttcgggca   1680

aaaaccattg tcaagttctc agatgaatac ctgacaaagc agtggaagta tccaattgag   1740

cttcatggga ttggtaaata tggcaacgac tcttaccgaa ttttttgtgt caatgagtgg   1800

aagcaggtgc accctgaaga ccacaaatta aataaatatc atgactggct ttgggaaaat   1860

catgaaaaat taagtttatc ttaaactctg cagctttcaa gctcatctgt tatgcatagc   1920

tttgcacttc aaaaaagctt aattaagtac aaccaaccac ctttccagcc atagagattt   1980
```

-continued

```
taattagccc aactagaagc ctagtgtgtg tgctttctta atgtgtgtgc caatggtgga   2040

tttttgctac tgaatgtgtt tgaacatgtt ttgagatttt tttaaaataa attattattt   2100

gacaacaaaa aaaaaaaaaa aaaaaaaaaa aaaaaaaaaa aaaaaaaaaa aa           2152


<210> SEQ ID NO 27
<211> LENGTH: 2152
<212> TYPE: DNA
<213> ORGANISM: Homo sapiens

<400> SEQUENCE: 27

ggcggcgtct ggggcgcttt cgcaacattc agacctcggt tgcagcccgg tgccgtgagc     60

tgaagaggtt tcacatctta ctccgcccca caccctgggc gttgcggcgc tgggctcgtt    120

gctgcagccg gaccctgctc gatgggcacg actgggctgg agagtctgag tctgggggac    180

cgcggagctg cccccaccgt cacctctagt gagcgcctag tcccagaccc gccgaatgac    240

ctccgcaaag aagatgttgc tatggaattg gaaagagtgg gagaagatga ggaacaaatg    300

atgataaaaa gaagcagtga atgtaatccc ttgctacaag aacccatcgc ttctgctcag    360

tttggtgcta ctgcaggaac agaatgccgt aagtctgtcc catgtggatg ggaaagagtt    420

gtgaagcaaa ggttatttgg gaagacagca ggaagatttg atgtgtactt tatcagccca    480

caaggactga agttcagatc caaaagttca cttgctaatt atcttcacaa aaatggagag    540

acttctctta agccagaaga ttttgatttt actgtacttt ctaaaagggg tatcaagtca    600

agatataaag actgcagcat ggcagccctg acatcccatc tacaaaacca aagtaacaat    660

tcaaactgga acctcaggac ccgaagcaag tgcaaaaagg atgtgtttat gccgccaagt    720

agtagttcag agttgcagga gagcagagga ctctctaact ttacttccac tcatttgctt    780

ttgaaagaag atgagggtgt tgatgatgtt aacttcagaa aggttagaaa gcccaaagga    840

aaggtgacta ttttgaaagg aatcccaatt aagaaaacta aaaaaggatg taggaagagc    900

tgttcaggtt ttgttcaaag tgatagcaaa agagaatctg tgtgtaataa agcagatgct    960

gaaagtgaac ctgttgcaca aaaaagtcag cttgatagaa ctgtctgcat ttctgatgct   1020

ggagcatgtg gtgagaccct cagtgtgacc agtgaagaaa acagccttgt aaaaaaaaaa   1080

gaaagatcat tgagttcagg atcaaatttt tgttctgaac aaaaaacttc tggcatcata   1140

aacaaatttt gttcagccaa agactcagaa cacaacgaga agtatgagga tacctttta    1200

gaatctgaag aaaccggaac aaaagtagaa gttgtggaaa ggaaagaaca tttgcatact   1260

gacattttaa aacgtggctc tgaaatggac aacaactgct caccaaccag gaaagacttc   1320

actggtgaga aaatatttca agaagatacc atcccacgaa cacagataga aagaaggaaa   1380

acaagcctgt atttttccag caaatataac aaagaagctc ttagcccccc acgacgtaaa   1440

gcctttaaga aatggacacc tcctcggtca ccttttaatc tcgttcaaga aacacttttt   1500

catgatccat ggaagcttct catcgctact atatttctca atcggacctc aggcaaaatg   1560

gcaatacctg tgctttggaa gtttctggag aagtatcctt cagctgaggt agcaagaacc   1620

gcagactgga gagatgtgtc agaacttctt aaacctcttg gtctctacga tcttcgggca   1680

aaaaccattg tcaagttctc agatgaatac ctgacaaagc agtggaagta tccaattgag   1740

cttcatggga ttggtaaata tggcaacgac tcttaccgaa ttttttgtgt caatgagtgg   1800

aagcaggtgc accctgaaga ccacaaatta aataaatatc atgactggct ttgggaaaat   1860

catgaaaaat taagtttatc ttaaactctg cagctttcaa gctcatctgt tatgcatagc   1920

tttgcacttc aaaaaagctt aattaagtac aaccaaccac ctttccagcc atagagattt   1980
```

-continued

```
taattagccc aactagaagc ctagtgtgtg tgctttctta atgtgtgtgc caatggtgga   2040

tttttgctac tgaatgtgtt tgaacatgtt ttgagatttt tttaaaataa attattattt   2100

gacaacaaaa aaaaaaaaaa aaaaaaaaaa aaaaaaaaaa aaaaaaaaaa aa           2152


<210> SEQ ID NO 28
<211> LENGTH: 942
<212> TYPE: DNA
<213> ORGANISM: Homo sapiens

<400> SEQUENCE: 28

ggaagcaggt gaggctcact cccatccata attcagcaca tttggtctct gaggcaaaat     60

aagtccacca ttatggttaa gactatttat tggatacaaa tgctattaca gtcacaaaca    120

attgtgttcc tggctgcggg gaagcgagtg gcatgtgggt tttggggttt ttgatcagta    180

agcgctccca agtccacaaa gaccagtcca gcggcgtggc ctctgactca tctccagtgg    240

tttgtcacct ctggccctgt tcctgtcatt ccctatttgt gtgctatctc taagcctgac    300

gtggttttcc tcctgtcaaa agtacaccac tacaggaaag caggaaggtt tgggccttgc    360

aatgtatgca tattgggttt ctcttagtgg tctcagacta cgtttgtggt gactgggtcc    420

tgcttcagcc ctgttgaata tgcccagcct gtggcatgct ggtggtcatc ctggcagctg    480

gtgggtggcc tggtatgctg cccactcagc ttgagactca ccctcatgca ttcagccagt    540

aggtctggcc aagcctgaac tgaaggacca tggtcctatc ccagcttcat cacagcaatc    600

cattgtgacc tgagaatcca tttaacctct cggtctagaa cctccttctg gaaagtgagg    660

tattaatact tgactcaatg ttatcgccac cccacattct aagtcatggt tgagtagtaa    720

tttggacagt accttgtaaa ttgtgtgaga ttaccttaat ataaggtata acttaaaata    780

ttcatgaatc ccaggaggtt aaaggttata acttttaggt atggtatcgt aatgtactgt    840

cccccagcaa acatttaaaa agccaatttt aaaaaatgta tttctgacta agttacatta    900

aggtctctgc ctctgtatct tatgtttctt ccaggtgcac cc                       942


<210> SEQ ID NO 29
<211> LENGTH: 384
<212> TYPE: PRT
<213> ORGANISM: Mus musculus

<400> SEQUENCE: 29

Lys Glu Asp Ile Ala Val Gly Leu Gly Gly Val Gly Glu Asp Gly Lys
1               5                   10                  15

Asp Leu Val Ile Ser Ser Glu Arg Ser Ser Leu Leu Gln Glu Pro Thr
            20                  25                  30

Ala Ser Thr Leu Ser Ser Thr Thr Ala Thr Glu Gly His Lys Pro Val
        35                  40                  45

Pro Cys Gly Trp Glu Arg Val Val Lys Gln Arg Leu Ser Gly Lys Thr
    50                  55                  60

Ala Gly Lys Phe Asp Val Tyr Phe Ile Ser Pro Gln Gly Leu Lys Phe
65                  70                  75                  80

Arg Ser Lys Arg Ser Leu Ala Asn Tyr Leu Leu Lys Asn Gly Glu Thr
                85                  90                  95

Phe Leu Lys Pro Glu Asp Phe Asn Phe Thr Val Leu Pro Lys Gly Ser
            100                 105                 110

Ile Asn Pro Gly Tyr Lys His Gln Ser Leu Ala Ala Leu Thr Ser Leu
        115                 120                 125
```

-continued

```
Gln Pro Asn Glu Thr Asp Val Ser Lys Gln Asn Leu Lys Thr Arg Ser
    130                 135                 140

Lys Trp Lys Thr Asp Val Leu Pro Leu Pro Ser Gly Thr Ser Glu Ser
145                 150                 155                 160

Pro Glu Ser Ser Gly Leu Ser Asn Ser Asn Ser Ala Cys Leu Leu Leu
                165                 170                 175

Arg Glu His Arg Asp Ile Gln Asp Val Asp Ser Glu Lys Arg Arg Lys
            180                 185                 190

Ser Lys Arg Lys Val Thr Val Leu Lys Gly Thr Ala Ser Gln Lys Thr
        195                 200                 205

Lys Gln Lys Cys Arg Lys Ser Leu Leu Glu Ser Thr Gln Arg Asn Arg
    210                 215                 220

Lys Arg Ala Ser Glu Asp Ser Ile Pro Arg Thr Gln Val Glu Lys Arg
225                 230                 235                 240

Lys Thr Ser Leu Tyr Phe Ser Ser Lys Tyr Asn Lys Glu Ala Leu Ser
                245                 250                 255

Pro Pro Arg Arg Lys Ser Phe Lys Lys Trp Thr Pro Pro Arg Ser Pro
            260                 265                 270

Phe Asn Leu Val Gln Glu Ile Leu Phe His Asp Pro Trp Lys Leu Leu
        275                 280                 285

Ile Ala Thr Ile Phe Leu Asn Arg Thr Ser Gly Lys Met Ala Ile Pro
    290                 295                 300

Val Leu Trp Glu Phe Leu Glu Lys Tyr Pro Ser Ala Glu Val Ala Arg
305                 310                 315                 320

Ala Ala Asp Trp Arg Asp Val Ser Glu Leu Leu Lys Pro Leu Gly Leu
                325                 330                 335

Tyr Asp Leu Arg Ala Lys Thr Ile Ile Lys Phe Ser Asp Glu Tyr Leu
            340                 345                 350

Thr Lys Gln Trp Arg Tyr Pro Ile Glu Leu His Gly Ile Trp Leu Lys
        355                 360                 365

Tyr Gly Asn Asp Ser Tyr Arg Ile Phe Cys Val Asn Glu Trp Lys Gln
    370                 375                 380


<210> SEQ ID NO 30
<211> LENGTH: 119
<212> TYPE: PRT
<213> ORGANISM: Homo sapiens

<400> SEQUENCE: 30

Lys Glu Asp Val Ala Met Glu Leu Glu Arg Val Gly Glu Asp Glu Glu
 1               5                  10                  15

Gln Met Met Ile Lys Arg Ser Ser Glu Cys Asn Pro Leu Leu Gln Glu
            20                  25                  30

Pro Ile Ala Ser Ala Gln Phe Gly Ala Thr Ala Gly Thr Glu Cys Arg
        35                  40                  45

Lys Ser Val Pro Cys Gly Trp Glu Arg Val Val Lys Gln Arg Leu Phe
    50                  55                  60

Gly Lys Thr Ala Gly Arg Phe Asp Val Tyr Phe Ile Ser Pro Gln Gly
65                  70                  75                  80

Leu Lys Phe Arg Ser Lys Ser Ser Leu Ala Asn Tyr Leu His Lys Asn
                85                  90                  95

Gly Glu Thr Ser Leu Lys Pro Glu Asp Phe Asp Phe Thr Val Leu Ser
            100                 105                 110

Lys Arg Gly Ile Lys Ser Arg
        115
```

-continued

<210> SEQ ID NO 31
<211> LENGTH: 132
<212> TYPE: PRT
<213> ORGANISM: Rattus

<400> SEQUENCE: 31

Lys Glu Asp Lys Glu Gly Lys His Glu Pro Leu Gln Pro Ser Ala His
1 5 10 15

His Ser Ala Glu Pro Ala Glu Ala Gly Lys Ala Glu Thr Ser Glu Ser
20 25 30

Ser Gly Ser Ala Pro Ala Val Pro Glu Ala Ser Ala Ser Pro Lys Gln
35 40 45

Arg Arg Ser Ile Ile Arg Asp Arg Gly Pro Met Tyr Asp Asp Pro Thr
50 55 60

Leu Pro Glu Gly Trp Thr Arg Lys Leu Lys Gln Arg Lys Ser Gly Arg
65 70 75 80

Ser Ala Gly Lys Tyr Asp Val Tyr Leu Ile Asn Pro Gln Gly Lys Ala
85 90 95

Phe Arg Ser Lys Val Glu Leu Ile Ala Tyr Phe Glu Lys Val Gly Asp
100 105 110

Thr Ser Leu Asp Pro Asn Asp Phe Asp Phe Thr Val Thr Gly Arg Gly
115 120 125

Ser Pro Ser Arg
130

<210> SEQ ID NO 32
<211> LENGTH: 126
<212> TYPE: PRT
<213> ORGANISM: Homo sapiens

<400> SEQUENCE: 32

Asp Pro Trp Lys Leu Leu Ile Ala Thr Ile Phe Leu Asn Arg Thr Ser
1 5 10 15

Gly Lys Met Ala Ile Pro Val Leu Trp Lys Phe Leu Glu Lys Tyr Pro
20 25 30

Ser Ala Glu Val Ala Arg Thr Ala Asp Trp Arg Asp Val Ser Glu Leu
35 40 45

Leu Lys Pro Leu Gly Leu Tyr Asp Leu Arg Ala Lys Thr Ile Val Lys
50 55 60

Phe Ser Asp Glu Tyr Leu Thr Lys Gln Trp Lys Tyr Pro Ile Glu Leu
65 70 75 80

His Gly Ile Gly Lys Tyr Gly Asn Asp Ser Tyr Arg Ile Phe Cys Val
85 90 95

Asn Glu Trp Lys Gln Val His Pro Glu Asp His Lys Leu Asn Lys Tyr
100 105 110

His Asp Trp Leu Trp Glu Asn His Glu Lys Leu Ser Leu Ser
115 120 125

<210> SEQ ID NO 33
<211> LENGTH: 184
<212> TYPE: PRT
<213> ORGANISM: E. coli

<400> SEQUENCE: 33

Ser Pro Phe Glu Leu Leu Ile Ala Val Leu Leu Ser Ala Gln Ala Thr
1 5 10 15

-continued

```
Asp Val Ser Val Asn Lys Ala Thr Ala Lys Leu Tyr Pro Val Ala Asn
            20                  25                  30

Thr Pro Ala Ala Met Leu Glu Leu Gly Val Glu Gly Val Lys Thr Tyr
        35                  40                  45

Ile Lys Thr Ile Gly Leu Tyr Asn Ser Lys Ala Glu Asn Ile Ile Lys
    50                  55                  60

Thr Cys Arg Ile Leu Leu Glu Gln His Asn Gly Glu Val Pro Glu Asp
65                  70                  75                  80

Arg Ala Ala Leu Glu Ala Leu Pro Gly Val Gly Arg Lys Thr Ala Asn
                85                  90                  95

Val Val Leu Asn Thr Ala Phe Gly Trp Pro Thr Ile Ala Val Asp Thr
            100                 105                 110

His Ile Phe Arg Val Cys Asn Arg Thr Gln Phe Ala Pro Gly Lys Asn
        115                 120                 125

Val Glu Gln Val Glu Glu Lys Leu Leu Lys Val Val Pro Ala Glu Phe
    130                 135                 140

Lys Val Asp Cys His His Trp Leu Ile Leu His Gly Arg Tyr Thr Cys
145                 150                 155                 160

Ile Ala Arg Lys Pro Arg Cys Gly Ser Cys Ile Ile Glu Asp Leu Cys
                165                 170                 175

Glu Tyr Lys Glu Lys Val Asp Ile
            180
```

<210> SEQ ID NO 34
<211> LENGTH: 188
<212> TYPE: PRT
<213> ORGANISM: M. thermoformicicum

<400> SEQUENCE: 34

```
Asp Pro Tyr Val Ile Leu Ile Thr Glu Ile Leu Leu Arg Arg Thr Thr
 1               5                  10                  15

Ala Gly His Val Lys Lys Ile Tyr Asp Lys Phe Phe Val Lys Tyr Lys
            20                  25                  30

Cys Phe Glu Asp Ile Leu Lys Thr Pro Lys Ser Glu Ile Ala Lys Asp
        35                  40                  45

Ile Lys Glu Ile Gly Leu Ser Asn Gln Arg Ala Glu Gln Leu Lys Glu
    50                  55                  60

Leu Ala Arg Val Val Ile Asn Asp Tyr Gly Gly Arg Val Pro Arg Asn
65                  70                  75                  80

Arg Lys Ala Ile Leu Asp Leu Pro Gly Val Gly Lys Tyr Thr Cys Ala
                85                  90                  95

Ala Val Met Cys Leu Ala Phe Gly Lys Lys Ala Ala Met Val Asp Ala
            100                 105                 110

Asn Phe Val Arg Val Ile Asn Arg Tyr Phe Gly Gly Ser Tyr Glu Asn
        115                 120                 125

Leu Asn Tyr Asn His Lys Ala Leu Trp Glu Leu Ala Glu Thr Leu Val
    130                 135                 140

Pro Gly Gly Lys Cys Arg Asp Phe Asn Leu Gly Leu Met Asp Phe Ser
145                 150                 155                 160

Ala Ile Ile Cys Ala Pro Arg Lys Pro Lys Cys Glu Lys Cys Gly Met
                165                 170                 175

Ser Lys Leu Cys Ser Tyr Tyr Glu Lys Cys Ser Thr
            180                 185
```

<210> SEQ ID NO 35

-continued

```
<211> LENGTH: 185
<212> TYPE: PRT
<213> ORGANISM: M. luteus

<400> SEQUENCE: 35

Thr Pro Phe Glu Leu Leu Val Ala Thr Val Leu Ser Ala Gln Thr Thr
 1               5                  10                  15

Asp Val Arg Val Asn Ala Ala Thr Pro Ala Leu Phe Ala Arg Phe Pro
            20                  25                  30

Asp Ala His Ala Met Ala Ala Ala Thr Glu Pro Glu Leu Gln Glu Leu
        35                  40                  45

Val Arg Ser Thr Gly Phe Tyr Arg Asn Lys Ala Ser Ala Ile Leu Arg
    50                  55                  60

Leu Ser Gln Glu Leu Val Gly Arg His Asp Gly Glu Val Pro Ala Arg
65                  70                  75                  80

Leu Glu Asp Leu Val Ala Leu Pro Gly Val Gly Arg Lys Thr Ala Phe
                85                  90                  95

Val Val Leu Gly Asn Ala Phe Gly Gln Pro Gly Ile Thr Val Asp Thr
            100                 105                 110

His Phe Gly Arg Leu Ala Arg Arg Leu Gly Phe Thr Asp Glu Thr Asp
        115                 120                 125

Pro Gly Lys Gly Arg Ala Arg Arg Gly Arg Pro Val Pro Pro Ala Arg
    130                 135                 140

Asp Trp Thr Met Leu Ser His Arg Leu Ile Phe His Gly Arg Arg Val
145                 150                 155                 160

Cys His Ala Arg Arg Pro Ala Cys Gly Arg Cys Pro Ile Ala Arg Trp
                165                 170                 175

Cys Pro Ser Tyr Ala Ala Gly Glu Thr
            180                 185


<210> SEQ ID NO 36
<211> LENGTH: 188
<212> TYPE: PRT
<213> ORGANISM: E. coli

<400> SEQUENCE: 36

Thr Pro Tyr Lys Val Trp Leu Ser Glu Val Met Leu Gln Gln Thr Gln
 1               5                  10                  15

Val Ala Thr Val Ile Pro Tyr Phe Glu Arg Phe Met Ala Arg Phe Pro
            20                  25                  30

Thr Val Thr Asp Leu Ala Asn Ala Pro Leu Asp Glu Val Leu His Leu
        35                  40                  45

Trp Thr Gly Leu Gly Tyr Tyr Ala Arg Ala Arg Asn Leu His Lys Ala
    50                  55                  60

Ala Gln Gln Val Ala Thr Leu His Gly Gly Lys Phe Pro Glu Thr Phe
65                  70                  75                  80

Glu Glu Val Ala Ala Leu Pro Gly Val Gly Arg Ser Thr Ala Gly Ala
                85                  90                  95

Ile Leu Ser Leu Ser Leu Gly Lys His Phe Pro Ile Leu Asp Gly Asn
            100                 105                 110

Val Lys Arg Val Leu Ala Arg Cys Tyr Ala Val Ser Gly Trp Pro Gly
        115                 120                 125

Lys Lys Glu Val Glu Asn Lys Leu Trp Ser Leu Ser Glu Gln Val Thr
    130                 135                 140

Pro Ala Val Gly Val Glu Arg Phe Asn Gln Ala Met Met Asp Leu Gly
145                 150                 155                 160
```

-continued

Ala Met Ile Cys Thr Arg Ser Lys Pro Lys Cys Ser Leu Cys Pro Leu
165 170 175

Gln Asn Gly Cys Ile Ala Ala Ala Asn Asn Ser Trp
180 185

<210> SEQ ID NO 37
<211> LENGTH: 85
<212> TYPE: PRT
<213> ORGANISM: Homo sapiens

<400> SEQUENCE: 37

Ile Ala Ser Ala Gln Phe Gly Ala Thr Ala Gly Thr Glu Cys Arg Lys
1 5 10 15

Ser Val Pro Cys Gly Trp Glu Arg Val Val Lys Gln Arg Leu Phe Gly
20 25 30

Lys Thr Ala Gly Arg Phe Asp Val Tyr Phe Ile Ser Pro Gln Gly Leu
35 40 45

Lys Phe Arg Ser Lys Ser Ser Leu Ala Asn Tyr Leu His Lys Asn Gly
50 55 60

Glu Thr Ser Leu Lys Pro Glu Asp Phe Asp Phe Thr Val Leu Ser Lys
65 70 75 80

Arg Gly Ile Lys Ser
85

<210> SEQ ID NO 38
<211> LENGTH: 76
<212> TYPE: PRT
<213> ORGANISM: Homo sapiens

<400> SEQUENCE: 38

Met Ala Glu Asp Trp Leu Asp Cys Pro Ala Leu Gly Pro Gly Trp Lys
1 5 10 15

Arg Arg Glu Val Phe Arg Lys Ser Gly Ala Thr Cys Gly Arg Ser Asp
20 25 30

Thr Tyr Tyr Gln Ser Pro Thr Gly Asp Arg Ile Arg Ser Lys Val Glu
35 40 45

Leu Thr Arg Tyr Leu Gly Pro Ala Cys Asp Leu Thr Leu Phe Asp Phe
50 55 60

Lys Gln Gly Ile Leu Cys Tyr Pro Ala Pro Lys Ala
65 70 75

<210> SEQ ID NO 39
<211> LENGTH: 24
<212> TYPE: DNA
<213> ORGANISM: Homo sapiens

<400> SEQUENCE: 39
taaaaaaaaa agaaagatca ttga 24

<210> SEQ ID NO 40
<211> LENGTH: 14
<212> TYPE: DNA
<213> ORGANISM: Homo sapiens

<400> SEQUENCE: 40
gaaagatcat tgag 14

<210> SEQ ID NO 41
<211> LENGTH: 16

-continued

<212> TYPE: DNA
<213> ORGANISM: Homo sapiens

<400> SEQUENCE: 41
taaaaaagga tgtagg 16

<210> SEQ ID NO 42
<211> LENGTH: 10
<212> TYPE: DNA
<213> ORGANISM: Homo sapiens

<400> SEQUENCE: 42
ggatgtagga 10

<210> SEQ ID NO 43
<211> LENGTH: 17
<212> TYPE: PRT
<213> ORGANISM: Homo sapiens
<220> FEATURE:
<221> NAME/KEY: misc_feature
<222> LOCATION: (2)...(7)
<223> OTHER INFORMATION: Xaa = any amino acid
<220> FEATURE:
<221> NAME/KEY: misc_feature
<222> LOCATION: 9, 10
<223> OTHER INFORMATION: Xaa = any amino acid
<220> FEATURE:
<221> NAME/KEY: misc_feature
<222> LOCATION: (12)...(16)
<223> OTHER INFORMATION: Xaa = any amino acid

<400> SEQUENCE: 43

Cys Xaa Xaa Xaa Xaa Xaa Xaa Cys Xaa Xaa Cys Xaa Xaa Xaa Xaa Xaa
1 5 10 15

Cys

<210> SEQ ID NO 44
<211> LENGTH: 866
<212> TYPE: DNA
<213> ORGANISM: Mus musculus

<400> SEQUENCE: 44
cttttttttt ttccttttaa gcccacaagg attgaagttc agatcaaaac gttcacttgc 60
taattatctt ctcaaaaatg gggagacttt tcttaagcct gaagatttta attttactgt 120
actgccgaaa gggagcatca atcccggtta taaacaccaa agtttggcag ctctgacttc 180
cctgcagcca aatgaaactg acgtttcaaa gcagaacctc aagacacgaa gcaagtggaa 240
aacagatgtg ttgcctctgc ccagtggtac ttcagagtcg ccagaaagca gcggactgtc 300
taactctaac tcggcttgct tgctattgag agaacatagg gacattcagg atgttgactc 360
tgagaagagg agaaagtcca aaagaaaggt gactgttttg aaaggaactg caagtcagaa 420
aaccaaacaa aagtgcagga agagtctctt agagtctact caaagaaaca gaaaaagagc 480
atctgtggtt cagaaggtgg gtgctgatcg cgagctggtg ccacaggaaa gtcaactcaa 540
cagaaccctc tgccctgcag atgcctgtgc aagggagact gttggcctgg ctggggaaga 600
aaaatcacca agcccaggac tggatctttg tttcatacaa gtaacttctg gcaccacaaa 660
caaattccat tcaactgaag cagcaggtga agcaaatcgt gagcagactt ttttagaatc 720
agaggaaatc agatcgaagg gagacagaaa gggggaggca catttgcata ctggtgtttt 780
acaggatggc tctgaaatgc ccagctgctc acaagccaag aaacacttta cttctgagac 840
atttcaaggt actcagtgca tgaaaa 866

-continued

<210> SEQ ID NO 45
<211> LENGTH: 121
<212> TYPE: DNA
<213> ORGANISM: Mus musculus

<400> SEQUENCE: 45
gactataaac taattttgct tctcagaaga cagcatccca cggacacaag tagaaaaaag 60
gaaaacaagc ctgtattttt ccagcaagta caacaaagaa ggtacccacc tttccctaag 120
c 121

<210> SEQ ID NO 46
<211> LENGTH: 166
<212> TYPE: DNA
<213> ORGANISM: Mus musculus
<220> FEATURE:
<221> NAME/KEY: misc_feature
<222> LOCATION: 8, 11, 152, 163
<223> OTHER INFORMATION: n = a, t, c, or g

<400> SEQUENCE: 46
tatatttntg nagctcttag ccccccaaga cgcaaatcct tcaagaaatg gacccctcct 60
cggtcacctt ttaatcttgt tcaagaaata cttttccatg acccatggaa gctcctcatc 120
gcgactatat ttctcaatcg gacctcaggt tnggggtcat tgncat 166

<210> SEQ ID NO 47
<211> LENGTH: 183
<212> TYPE: DNA
<213> ORGANISM: Mus musculus

<400> SEQUENCE: 47
tgtttatgct ccccaggcaa gatggccatc cctgtgctgt gggagtttct agagaagtac 60
ccttcagctg aagtggcccg agctgccgac tggagggacg tgtcggagct tctcaagcct 120
cttggtctct acgatctccg tgcaaaaacc attatcaagt tctcaggtat gtccccagcc 180
cag 183

<210> SEQ ID NO 48
<211> LENGTH: 143
<212> TYPE: DNA
<213> ORGANISM: Mus musculus

<400> SEQUENCE: 48
tggatgtgta tccctcagat gaatatctga caaagcagtg gaggtatccg attgagcttc 60
atgggatttg gttaaaatat ggcaacgact ctaccggatc ttttgtgtca atgaatggaa 120
caggtaagcc caccactggg gcc 143

<210> SEQ ID NO 49
<211> LENGTH: 810
<212> TYPE: DNA
<213> ORGANISM: Homo sapiens

<400> SEQUENCE: 49
tttggaagac aggaaatact cccatagcac aagactggtc cacactgact ttaatctccc 60
tcattttaat atggataatc tatgtggttc ctgcattgtc atggattaaa actgagtagg 120
cagtggaaga taaattttaa ataagttaat cacttagact ttgtttttcc agcaaagaag 180
atgttgctat ggaattggaa agagtgggag aagatgagga acaaatgatg ataaaaagaa 240

-continued

```
gcagtgaatg taatcccttg ctacaagaac ccatcgcttc tgctcagttt ggtgctactg    300

caggaacaga atgccgtaag tctgtcccat gtggatggga aagagttgtg aagcaaaggt    360

tatttgggaa gacagcagga agatttgatg tgtactttat caggtaagca tataagatgg    420

taaagatagt acagccaaat gattttgtct gggcaggtag tgggagcata gcaggaatct    480

tagcttcttt atatttttac cataaaacca ttgcagattc tattctttca atgttgctat    540

taattacatc aagtgatttg gggaaaatta catacatttt gtccctcctt ctgtgaatgg    600

ttaacgggta ggttgcattt tagttatatt tataaattta tattgtcata gaggaaccat    660

ttaaaaggcc attatcactc tttttcattt ttaaatgaca gagacctatg gcaacatttg    720

gaaattaatt agaatctgaa atgtggtcca gttcttttaa aagtcccttc tatttactag    780

cagtaagttt cctttaatat cattttctag                                     810


<210> SEQ ID NO 50
<211> LENGTH: 1017
<212> TYPE: DNA
<213> ORGANISM: Homo sapiens
<220> FEATURE:
<221> NAME/KEY: misc_feature
<222> LOCATION: 536, 665
<223> OTHER INFORMATION: n = a, t, c, or g

<400> SEQUENCE: 50

aatctgaaat gtggtccagt tcttttaaaa gtcccttcta tttactagca gtaagtttcc     60

tttaatatca ttttctagcc cacaaggact gaagttcaga tccaaaagtt cacttgctaa    120

ttatcttcac aaaaatggag agacttctct taagccagaa gattttgatt ttactgtact    180

ttctaaaagg ggtatcaagt caagatataa agactgcagc atggcagccc tgacatccca    240

tctacaaaac caaagtaaca attcaaactg gaacctcagg acccgaagca agtgcaaaaa    300

ggatgtgttt atgccgccaa gtagtagttc agagttgcag gagagcagag gactctctaa    360

ctttacttcc actcatttgc ttttgaaaga agatgagggt gttgatgatg ttaacttcag    420

aaaggttaga aagcccaaag gaaaggtgac tattttgaaa ggaatcccaa ttaagaaaac    480

taaaaaagga tgtaggaaga gctgttcagg ttttgttcaa agtgatagca aaaganaatc    540

tgtgtgtaat aaagcagatg ctgaaagtga acctgttgca caaaaaagtc agcttgatag    600

aactgtctgc atttctgatg ctggagcatg tggtgagacc ctcagtgtga gcagtgaaga    660

aaacngcctt gtaaaaaaaa aagaaagatc attgagttca ggatcaaatt tttgttctga    720

acaaaaaact tctggcatca taaacaaatt ttgttcagcc aaagactcag aacacaacga    780

gaagtatgag gataccttttt tagaatctga agaaatcgga acaaaagtag aagttgtgga    840

aaggaaagaa catttgcata ctgacatttt aaaacgtggc tctgaaatgg acaacaactg    900

ctcaccaacc aggaaagact tcactggtga gaaaatattt caaggtatcc agtgctttca    960

gcactattaa acattagtga tgagaaattt atatgctgca tctgtatcgt gccatac      1017


<210> SEQ ID NO 51
<211> LENGTH: 613
<212> TYPE: DNA
<213> ORGANISM: Homo sapiens

<400> SEQUENCE: 51

tagtaccaag ttcatgggtc attagttaga ttaattgggt atttatgtaa agggcttaga     60

atagtgcctg gcatgctttg taatagtgtt gatattatta tttgcatccc tcaatattgc    120

tttaagctaa accatagact ccataaagtg tttacttttc cttttcagaa gataccatcc    180
```

-continued

```
cacgaacaca gatagaaaga aggaaaacaa gcctgtattt ttccagcaaa tataacaaag    240

aaggtatccc tttcccaatc agaacagcaa attctaattc cattttgggt tttcaattct    300

gatgcactat gtttgtttag ctcttagccc cccacgacgt aaagccttta agaaatggac    360

acctcctcgg tcacctttta atctcgttca agaaacactt tttcatgatc catggaagct    420

tctcatcgct actatatttc tcaatcggac ctcaggtttg gggattatta tcatctttgt    480

cttagtagag acagtgtggt agggagaaag cactgaattg aggcctgggt tcaaagtcat    540

tttgagtgtg tcacctggga tagggcattc ccccttcac ccttaaactc ttcacctatg    600

aggaaaatgg ggg                                                        613
```

```
<210> SEQ ID NO 52
<211> LENGTH: 463
<212> TYPE: DNA
<213> ORGANISM: Homo sapiens
<220> FEATURE:
<221> NAME/KEY: misc_feature
<222> LOCATION: 128
<223> OTHER INFORMATION: n = a, t, c, or g

<400> SEQUENCE: 52

ccagtgtttt ttgtttttttg ttttctttaa aaaaaaaaaa aaaccctctg gatgagattt     60

ctatgagaaa ctacttgaac gtgaaatcag cccacctgga gtcttgtaat cattcagtta    120

cttttacntt cccaggcaaa atggcaatac ctgtgctttg gaagtttctg gagaagtatc    180

cttcagctga ggtagcaaga accgcagact ggagagatgt gtcagaactt cttaaacctc    240

ttggtctcta cgatcttcgg gcaaaaacca ttgtcaagtt ctcaggtatt ttcctataca    300

cccaaaggaa aaacataata cattgtgctt atttaagaga gccacacctt aaactttaat    360

gttctcagat actatattaa tggaggtttt tcagctcaag catttaaaaa agtccacttt    420

tccccaaacc acagtctccc actgacctaa acaataaatc ttt                       463
```

```
<210> SEQ ID NO 53
<211> LENGTH: 332
<212> TYPE: DNA
<213> ORGANISM: Homo sapiens
<220> FEATURE:
<221> NAME/KEY: misc_feature
<222> LOCATION: 223, 287
<223> OTHER INFORMATION: n = a, t, c, or g

<400> SEQUENCE: 53

ctttagaagc tgacctgata atgtgggatg ttgtattctt cagatgaata cctgacaaag     60

cagtggaagt atccaattga gcttcatggg attggtaaat atggcaacga ctcttaccga    120

attttttgtg tcaatgagtg gaagcaggtg aggctcactc ccatccataa ttcagcacat    180

ttggtctctg aggcaaaata agtccaccat tatggttaag acnatttatt ggggatacaa    240

atgctattac agtcacaaca attgtgttcc tggctgcggg gaagcgngtg gcatgtgggt    300

tttggggttt ttgatcagta ggcgctccca gg                                   332
```

```
<210> SEQ ID NO 54
<211> LENGTH: 623
<212> TYPE: DNA
<213> ORGANISM: Homo sapiens
<220> FEATURE:
<221> NAME/KEY: misc_feature
<222> LOCATION: 158
<223> OTHER INFORMATION: n = a, t, c, or g
```

-continued

<400> SEQUENCE: 54
tgtgtgagat taccttaata taaggtataa cttaaaatat tcatgaatcc caggaggtta 60
aaggttataa cttttaggta tggtatcgta atgtactgtc ccccagcaaa catttaaaaa 120
gccaatttta aaaaatgtat ttctgactaa gttacatnta aggtctctgc ctctgtatct 180
tatgtttctt ccaggtgcac cctgaagacc acaaattaaa taaatatcat gactggcttt 240
cccaaaatca tgaaaaatta agtttatctt aaactctgca gctttcaagc tcatctgtta 300
tgcatagctt tgcacttcaa aaaagcttaa ttaagtacaa ccaaccacct ttccagccat 360
agagatttta attagcccaa ctagaagcct agtgtgtgtg ctttcttaat gtgtgtgcca 420
atggtggatc tttgctactg aatgtgtttg aacatgtttt gagatttttt taaaataaat 480
tattatttga caacaatcca aaaaaaatac ggcttttcca atgatgaaat ataatcagaa 540
gatgaaaaat agttctaaac tatcaataat acaaagcaaa tttctatcag ccttgctaaa 600
gctaggggcc cactaaatat ttt 623

<210> SEQ ID NO 55
<211> LENGTH: 24
<212> TYPE: DNA
<213> ORGANISM: Artificial Sequence
<220> FEATURE:
<223> OTHER INFORMATION: primer

<400> SEQUENCE: 55
ctcgttgtgt tctgagcttt tggc 24

<210> SEQ ID NO 56
<211> LENGTH: 21
<212> TYPE: DNA
<213> ORGANISM: Artificial Sequence
<220> FEATURE:
<223> OTHER INFORMATION: primer

<400> SEQUENCE: 56
cagtgtgacc agtgaagaaa a 21

<210> SEQ ID NO 57
<211> LENGTH: 20
<212> TYPE: DNA
<213> ORGANISM: Artificial Sequence
<220> FEATURE:
<223> OTHER INFORMATION: primer

<400> SEQUENCE: 57
tgaaaggaat cccaattaag 20

<210> SEQ ID NO 58
<211> LENGTH: 20
<212> TYPE: DNA
<213> ORGANISM: Artificial Sequence
<220> FEATURE:
<223> OTHER INFORMATION: primer

<400> SEQUENCE: 58
gacagttcta tcaagctgac 20

<210> SEQ ID NO 59
<211> LENGTH: 63
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: 34
<223> OTHER INFORMATION: n = a, g, c, t

<400> SEQUENCE: 59
ccgtcatgct agttcacttt atgcttccgg ctcncgtcat gtgtggaatt gtgattaaaa 60
tcg 63

<210> SEQ ID NO 60
<211> LENGTH: 63
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (31)...(31)
<223> OTHER INFORMATION: n = a, g, c, t, u, ethenocytosine

<400> SEQUENCE: 60
gcgattttaa tcacaattcc acacatgacg ngagccggaa gcataaagtg aactagcatg 60
acg 63

<210> SEQ ID NO 61
<211> LENGTH: 63
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: 33
<223> OTHER INFORMATION: n = a, g, c, t

<400> SEQUENCE: 61
ccgtcatgct agttcacttt atgcttccgg ctngcgtcat gtgtggaatt gtgattaaaa 60
tcg 63

<210> SEQ ID NO 62
<211> LENGTH: 63
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: 31
<223> OTHER INFORMATION: n = t, u
<220> FEATURE:
<221> NAME/KEY: misc_feature
<222> LOCATION: 32
<223> OTHER INFORMATION: n = a, g, c, t

<400> SEQUENCE: 62
gcgattttaa tcacaattcc acacatgacg nnagccggaa gcataaagtg aactagcatg 60
acg 63

<210> SEQ ID NO 63
<211> LENGTH: 64
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: 35

-continued

<223> OTHER INFORMATION: n = a, g, c, t

<400> SEQUENCE: 63
ccgtcatgct agttcacttt atgcttccgg ctcgncgtca tgtgtggaat tgtgattaaa 60
atcg 64

<210> SEQ ID NO 64
<211> LENGTH: 65
<212> TYPE: DNA
<213> ORGANISM: Artificial Sequence
<220> FEATURE:
<223> OTHER INFORMATION: synthetic oligonucleotide

<400> SEQUENCE: 64
ccgtcatgct agttcacttt atgcttccgg ctcggtcgtc atgtgtggaa ttgtgattaa 60
aatcg 65

<210> SEQ ID NO 65
<211> LENGTH: 66
<212> TYPE: DNA
<213> ORGANISM: Artificial Sequence
<220> FEATURE:
<223> OTHER INFORMATION: synthetic oligonucleotide

<400> SEQUENCE: 65
ccgtcatgct agttcacttt atgcttccgg ctcggtacgt catgtgtgga attgtgatta 60
aaatcg 66

<210> SEQ ID NO 66
<211> LENGTH: 67
<212> TYPE: DNA
<213> ORGANISM: Artificial Sequence
<220> FEATURE:
<223> OTHER INFORMATION: synthetic oligonucleotide

<400> SEQUENCE: 66
ccgtcatgct agttcacttt atgcttccgg ctcggtaccg tcatgtgtgg aattgtgatt 60
aaaatcg 67

<210> SEQ ID NO 67
<211> LENGTH: 68
<212> TYPE: DNA
<213> ORGANISM: Artificial Sequence
<220> FEATURE:
<223> OTHER INFORMATION: synthetic oligonucleotide

<400> SEQUENCE: 67
ccgtcatgct agttcacttt atgcttccgg ctcggtactc gtcatgtgtg gaattgtgat 60
taaaatcg 68

<210> SEQ ID NO 68
<211> LENGTH: 68
<212> TYPE: DNA
<213> ORGANISM: Artificial Sequence
<220> FEATURE:
<223> OTHER INFORMATION: synthetic oligonucleotide

<400> SEQUENCE: 68
ccgtcatgct agttcacttt atgcttccgg ctcggggggc gtcatgtgtg gaattgtgat 60
taaaatcg 68

-continued

<210> SEQ ID NO 69
<211> LENGTH: 62
<212> TYPE: DNA
<213> ORGANISM: Artificial Sequence
<220> FEATURE:
<223> OTHER INFORMATION: synthetic oligonucleotide

<400> SEQUENCE: 69
ccgtcatgct agttcacttt atgcttccgg ctcggtcatg tgtggaattg tgattaaaat 60
cg 62

<210> SEQ ID NO 70
<211> LENGTH: 63
<212> TYPE: DNA
<213> ORGANISM: Artificial Sequence
<220> FEATURE:
<223> OTHER INFORMATION: synthetic oligonucleotide

<400> SEQUENCE: 70
gcgattttaa tcacaattcc acacatgacg cgagccggaa gcataaagtg aactagcatg 60
acg 63

<210> SEQ ID NO 71
<211> LENGTH: 37
<212> TYPE: DNA
<213> ORGANISM: Artificial Sequence
<220> FEATURE:
<223> OTHER INFORMATION: synthetic oligonucleotide

<400> SEQUENCE: 71
caatcctagc tgacacgatg tggccaatgg catgact 37

<210> SEQ ID NO 72
<211> LENGTH: 37
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: 22
<223> OTHER INFORMATION: n = c, t, u, ethenocytosine

<400> SEQUENCE: 72
gagtcatgcc attggccaca tngtgtcagc taggatt 37

<210> SEQ ID NO 73
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 73
gacttcactg gtgagaaaat atttcaaggt 30

GENE ENCODING A DNA REPAIR ENZYME AND METHODS OF USE THEREOF

CROSS-REFERENCE TO RELATED APPLICATIONS

This application is a continuation of U.S. patent application Ser. No. 11/739,558, filed Apr. 24, 2007, now U.S. Pat. No. 7,491,807 which is a continuation of U.S. patent application Ser. No. 10/629,951, Jul. 29, 2003, now U.S. Pat. No. 7,208,583, which is a continuation of U.S. patent application Ser. No. 09/629,222, filed Jul. 31, 2000, now U.S. Pat. No. 6,599,700, which is a continuation-in-part of U.S. patent application Ser. No. 09/463,891, filed Jan. 28, 2000, now abandoned, which is the U.S. national phase application of PCT/US98/15828, filed Jul. 28, 1999. This application also claims priority under 35 USC §119(e) to U.S. Provisional Application 60/053,936, filed Jul. 28, 1997. The entire disclosure of all of the above-identified applications is incorporated by reference herein.

FIELD OF THE INVENTION

This invention relates to the field of DNA repair. Specifically, a novel human gene, its encoded enzyme and methods of use thereof are disclosed. The gene may be used beneficially as a marker for genetic screening, mutational analysis and for assessing drug resistance in transformed cells. The encoded enzyme may be used to advantage in glycosylase assays.

BACKGROUND OF THE INVENTION

Several publications are referenced in this application in order to more fully describe the state of the art to which this invention pertains. The disclosure of each of these publications is incorporated by reference herein.

Mismatch repair stabilizes the cellular genome by correcting DNA replication errors and by blocking recombination events between divergent DNA sequences. The mechanism responsible for strand-specific correction of mispaired bases has been highly conserved during evolution. Eukaryotic homologs of bacterial MutS and MutL, which are believed to play key roles in mismatch repair recognition and initiation of repair, have been identified in yeast and mammalian cells. Inactivation of genes encoding these activities results in large increases in spontaneous mutability, and in the case of humans and rodents, predisposition to tumor development.

Lynch syndrome or hereditary nonpolyposis colon cancer (HNPCC) is an autosomal dominant disease, which accounts for approximately 1-5% of all colorectal cancer cases. In this syndrome, colorectal tumors are frequently associated with extracolonic malignancies, such as cancers of the endometrium, stomach, ovary, brain, skin and urinary tract. Tumors from HNPCC patients harbor a genome-wide DNA replication/repair defect. Due to the lack of pathognomonic morphological or biomolecular markers, HNPCC has traditionally posed unique problems to clinicians and geneticists alike, both in terms of diagnosis and clinical management.

Recent breakthroughs in molecular biology have partially elucidated the pathogenic mechanism of this syndrome. Germline mutations in any one of five genes encoding proteins that participate in a specialized DNA mismatch repair system give rise to a predisposition for cancer development in HNPCC families. Patients affected by HNPCC carry these mutations in genes which are involved in DNA mismatch repair. The DNA mismatch repair mechanism contributes to mutational avoidance and genetic stability, thus performing a tumor suppressor function. Loss or inactivation of the wild type allele in somatic cells leads to a dramatic increase of the spontaneous mutation rate. This, in turn, results in the accumulation of mutations in other tumor suppressor genes and oncogenes, ultimately leading to neoplastic transformation.

Microsatellites are repeating sequences that are distributed throughout the human genome, most commonly (A)n/(T)n and (CA)n/(GT)n. Their function is unknown, but they are useful in genetic linkage studies because of their high degree of polymorphism and normally stable inheritance. Several of the genes responsible for HNPCC have been identified using analysis of mutation rate in DNA microsatellites. Mutations of mismatch repair genes can be detected in a subset of sporadic colonic and extracolonic cancers which exhibit variability in the length of microsatellite sequences. This variability is often referred to as microsatellite instability.

Investigators in the field (Peltomaki et al., (1993) *Science* 260:810-812) have discovered that most colorectal cancers from HNPCC patients show microsatellite instability. These studies revealed that the length of microsatellite DNA at different loci varies between tumor DNA and non-tumor DNA from the same patient. The phrase "replication error positive" (RER+) has been used to describe such tumors. It should be noted that only about 70% of HNPCC cases and only about 65% of sporadic tumors with microsatellite instability carry mutations in the known mismatch repair genes (hMSH2, hMLH1, hPMS2, hMSH6 and hPMS1) (Liu et al., (1996) *Nature Medicine* 2:169-174). The remaining 30-35% of the cases have an as yet unidentified mismatch repair genetic defect. Thus, there is a pressing need to identify the other active components in the DNA mismatch repair pathway, as mutations in these genes may result in an increased propensity for cancer.

The Fragile X or Martin Bell syndrome is the most common single recognized form of inherited mental retardation. Fifty percent of all X-linked mental retardation may be attributable to the Fragile X syndrome. The disorder is found in all ethnic groupings with a frequency of 0.3-1 per 1000 males and 0.2-0.6 per 1000 females. The full clinical syndrome, which is found in approximately 60% of affected males, consists of moderate mental retardation with an IQ typically in the range 35-50, elongated facies with large everted ears, and macroorchidism. This syndrome is unusual in that it is associated with the appearance of a fragile site on the long arm of the X chromosome at Xq27.3 (Sutherland, G. R., (1977) *Science* 197:256-266). This can be visualized cytogenetically in metaphase chromosomes prepared from lymphocytes of affected individuals which have been cultured under conditions of folate deficiency or thymidine stress. The study of the segregation of polymorphic markers within fragile X families has confirmed that the mutation lies in the same region of the X-chromosome as that exhibiting cytogenetic fragility.

There is an imbalance of penetrance of the phenotype associated with this syndrome in the different generations of kindreds in which the mutation is segregating. The likelihood of developing mental impairment depends on an individual's position in the pedigree. As the mutation progresses through the generations, the risk of mental impairment increases. These observations are not consistent with classical X linkage and are collectively known as the Sherman paradox. Hypotheses based on these observations have suggested that the mutation exists in two forms—a premutation and a full mutation form. Nonpenetrant individuals are said to carry a premutation chromosome, that is, a chromosome which has no abnormal phenotypic effect but which is capable of progressing to a fully penetrant mutation on passage through a female oogenesis.

Two alterations in the DNA at the fragile X site have been identified: abnormal amplification of a CpG-rich DNA sequence (a CpG island) and hypermethylation of such sequences. The molecular basis of the amplification is the expansion of a CGG triplet microsatellite into large arrays. In individuals expressing the full clinical phenotype, the DNA in this region becomes hypermethylated, leading to the transcriptional shut down of the gene FMR-1 (fragile X mental retardation 1) which is transcribed across this region. The clinical phenotype is likely caused by a loss of gene expression. It has been postulated that in Fragile X syndrome, expansion of the (CGG)n repeat from premutation to full mutation may be related to an aberrant (misdirected) DNA mismatch repair event. This may be favored by the transient lack of multiple methyl signals in the CGG repeat as well as in flanking single copy sequences during early stages of embryonal development. Similar to Fragile X syndrome, defective DNA mismatch repair may play a role in the expansion of triplet repeats associated with several disorders such as myotonic dystrophy, Huntington's disease, spino-cerebellar ataxias and Kennedy's disease.

The isolation of nucleic acids and proteins which, when mutated, give rise to these various disorders, enables the development of diagnostic and prognostic kits for assessing patients at risk. The biochemical characterization of the genes encoding the components of the DNA mismatch repair system may ultimately facilitate gene replacement therapies for use in the treatment of malignancy and other inherited genetic disorders.

SUMMARY OF THE INVENTION

This invention provides biological molecules useful for identification, detection, and/or regulation of components in the complex DNA damage recognition/repair pathway. According to one aspect of the invention, an isolated nucleic acid molecule is provided which includes a sequence encoding a methyl CpG binding protein of a size between about 60 and 75 kilodaltons. The encoded protein, referred to herein as MED1 (methyl-CpG binding endonuclease 1; also referred to in the literature as MBD4)) comprises a tripartite structure including an amino terminal methyl-CpG binding domain with significant homology to the rat protein, MeCP2 and the human protein, PCM1, a central region rich in positively charged amino acids which contains nuclear localization signals, and a carboxy terminal catalytic domain which shares homology with several bacterial endonucleases involved in DNA repair. The protein demonstrates significant binding affinity for hMLH1 and mMSH2. In a preferred embodiment of the invention, an isolated nucleic acid molecule is provided that includes a cDNA encoding a human MED1 protein. In a particularly preferred embodiment, the human MED1 protein has an amino acid sequence the same as Sequence I.D. No. 2. An exemplary nucleic acid molecule of the invention comprises Sequence I.D. No. 1.

According to another aspect of the present invention, an isolated nucleic acid molecule is provided, which has a sequence selected from the group consisting of: (1) Sequence I.D. No. 1; (2) a sequence specifically hybridizing with preselected portions or all of the complementary strand of Sequence I.D. No. 1; a sequence encoding preselected portions of Sequence I.D. No. 1, (3) a sequence encoding part or all of a polypeptide having amino acid Sequence I.D. No. 2. Such partial sequences are useful as probes to identify and isolate homologues of the MED1 gene of the invention. Accordingly, isolated nucleic acid sequences encoding natural allelic variants of Sequence I.D. No. 1 are also contemplated to be within the scope of the present invention. The term natural allelic variants will be defined hereinbelow.

In yet another embodiment of the invention, isolated genomic DNA molecules are provided which encode the Med-1 protein of the invention. These nucleic acids (SEQ ID NO: 21 and 22) may be used to advantage in screening assays which identify germline and somatic mutations in the DNA encoding Med-1.

The present invention also provides MED1 genomic nucleic acid of mouse or human origin having a sequence substantially the same as that contained in phage stocks as deposited on 28 Jul. 1998 at the American Type Culture Collection, 10801 University Blvd, Manassas, Va. 20110-2209 USA, under the terms of the Budapest Treaty with accession numbers: 203073 and 203074.

MED1 polypeptide may conveniently be obtained by introducing expression vectors into host cells in which the vector is functional, culturing the host cells so that the MED1 polypeptide is produced and recovering the MED1 polypeptide from the host cells or the surrounding medium. Vectors comprising nucleic acid according to the present invention and host cells comprising such vectors or nucleic acid form further aspects of the present invention.

According to another aspect of the present invention, an isolated human methyl CpG binding protein is provided which has a deduced molecular weight of between about 60 kDa and 75 kDa. The protein comprises an amino-terminal methyl-CpG binding domain with significant homology to the rat protein MeCP2 and the human protein PCM1, a central region rich in positively-charged amino acids which contains nuclear localization signals, and a carboxy terminal catalytic domain which shares homology with several bacterial endonucleases involved in DNA repair. In a preferred embodiment of the invention, the protein is of human origin, and has an amino acid sequence the same as Sequence I.D. No. 2. In a further embodiment the protein may be encoded by natural allelic variants of Sequence I.D. No. 1. Inasmuch as certain amino acid variations may be present in a MED1 protein encoded by a natural allelic variant, such proteins are also within the scope of the invention.

According to another aspect of the present invention, antibodies immunologically specific for the proteins described hereinabove are provided.

In yet a further aspect of the invention, assays are provided for assessing the glycosylase activity of MED1. Also provided are methods employing the MED1 protein to detect transition single-nucleotide polymorphisms at CpG sites. Also provided are methods wherein polymerase chain reaction/single strand conformation polymorphism are utilized to detect mutations in the MED1 gene. Methods employing loss of heterozygosity (LOH) analysis are also disclosed which may be used to advantage in mutational screening assays for possible MED1 mutations.

Various terms relating to the biological molecules of the present invention are used hereinabove and also throughout the specifications and claims. The terms "specifically hybridizing," "percent similarity" and "percent identity (identical)" are defined in detail in the description set forth below.

With reference to nucleic acids of the invention, the term "isolated nucleic acid" is sometimes used. This term, when applied to DNA, refers to a DNA molecule that is separated from sequences with which it is immediately contiguous (in the 5' and 3' directions) in the naturally occurring genome of the organism from which it originates. For example, the "isolated nucleic acid" may comprise a DNA or cDNA molecule inserted into a vector, such as a plasmid or virus vector, or integrated into the DNA of a prokaryote or eukaryote.

With respect to RNA molecules of the invention, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form (the term "substantially pure" is defined below).

With respect to protein, the term "isolated protein" or "isolated and purified protein" is sometimes used herein. This term refers primarily to a protein produced by expression of an isolated nucleic acid molecule of the invention.

Alternatively, this term may refer to a protein which has been sufficiently separated from other proteins with which it would naturally be associated, so as to exist in "substantially pure" form.

The term "substantially pure" refers to a preparation comprising at least 50-60% by weight the compound of interest (e.g., nucleic acid, oligonucleotide, protein, etc.). More preferably, the preparation comprises at least 75% by weight, and most preferably 90-99% by weight, the compound of interest. Purity is measured by methods appropriate for the compound of interest (e.g. chromatographic methods, agarose or polyacrylamide gel electrophoresis, HPLC analysis, and the like).

With respect to antibodies of the invention, the term "immunologically specific" refers to antibodies that bind to one or more epitopes of a protein of interest (e.g., MED1), but which do not substantially recognize and bind other molecules in a sample containing a mixed population of antigenic biological molecules.

With respect to oligonucleotides, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

The present invention also includes active portions, fragments, derivatives and functional mimetics of the MED1 polypeptide or protein of the invention.

An "active portion" of MED1 polypeptide means a peptide which is less than said full length MED1 polypeptide, but which retains its essential biological activity, e.g., methyl-CpG DNA binding and/or endonuclease activity and/or glycosylase activity.

A "fragment" of the MED1 polypeptide means a stretch of amino acid residues of at least about five to seven contiguous amino acids, often at least about seven to nine contiguous amino acids, typically at least about nine to thirteen contigous amino acids and, most preferably, at least about twenty to thirty or more contiguous amino acids. Fragments of the MED1 polypeptide sequence, antigenic determinants or epitopes are useful for raising antibodies to a portion of the MED1 amino acid sequence.

A "derivative" of the MED1 polypeptide or a fragment thereof means a polypeptide modified by varying the amino acid sequence of the protein, e.g. by manipulation of the nucleic acid encoding the protein or by altering the protein itself. Such derivatives of the natural amino acid sequence may involve insertion, addition, deletion or substitution of one or more amino acids, without fundamentally altering the essential activity of the wildtype MED1 polypeptide.

"Functional mimetic" means a substance which may not contain an active portion of the MED1 amino acid sequence, and probably is not a peptide at all, but which retains the essential biological activity of natural MED1 polypeptide.

The nucleic acids, proteins/polypeptides, peptides and antibodies of the present invention may be used to advantage as markers for diagnosis and prognosis of those at risk for colon and other cancers. The molecules may also be useful in the diagnosis and/or treatment of Fragile X syndrome and other diseases characterized by triplet repeat expansion. The MED1 molecules of the invention may also be used as research tools in DNA modification/DNA analysis technologies and will facilitate the elucidation of the mechanistic action of the novel genetic and protein interactions involved in the maintenance of DNA fidelity.

Thus, the present invention also provides nucleic acid molecules, polypeptides and/or antibodies as mentioned above for use in medical treatment.

Further, the present invention provides use of a nucleic acid molecule, polypeptide and/or antibody in the preparation of a medicament for treating cancer, in particular, colorectal cancer.

In a further aspect of the present invention, there is provided a kit for detecting mutations in the MED1 gene associated with cancer, or a susceptibility to cancer, the kit comprising one or more nucleic acid probes capable of binding and/or detecting a mutated MED1 nucleic acid. Alternatively, the kit may comprise one or more antibodies capable of specifically binding and/or detecting a mutated MED1 nucleic acid or amino acid sequence or a pair of oligonucleotide primers having sequences corresponding to, or complementary to a portion of the nucleic acid sequence set out in Sequence I. D. No. 1 or 5 for use in amplifying a MED1 nucleic acid sequence or mutant allele thereof.

In yet another aspect of the invention, transgenic animals are provided which are useful for elucidating the role of MED1 in growth and development. Isolation of the mouse genomic DNA also facilitates the production of MED1 knock-out mice.

Aspects and embodiments of the present invention will now be illustrated, by way of example, with reference to the accompanying figures. Further aspects and embodiments will be apparent to those skilled in the art. All documents mentioned in this text are incorporated herein by reference.

BRIEF DESCRIPTION OF THE DRAWINGS

FIG. 3 shows an alignment of the cDNA of Sequence I.D. No. 1 and its encoded MED1 protein, Sequence I.D. No. 2.

FIG. 4A depicts homology analysis of the deduced amino acid sequence of MED1 and several other endonucleases involved in DNA damage recognition and repair. FIG. 4C depicts homology analysis of the deduced amino acid sequence of MED1 and the methyl-CpG binding domain of the human protein, PCM1.

FIG. 9A is a Coomassie-stained SDS-PAGE showing IPTG induction of the bacterially-expressed 18-22-kD MED1 endonuclease domain (codons 455-580) (arrowhead, left panel). In a parallel SDS-PAGE nuclease activity gel (containing heat-denatured calf thymus DNA), the IPTG-induced 18-22-kD MED1 endonuclease domain is negatively stained with the DNA dye, toluidine blue (arrowhead, right panel). P, pellet of 10,000×g centrifugation; S, supernatant of 10,000×g centrifugation. FIG. 9B shows endonuclease activity of recombinant wild-type MED1. The entire wild-type MED1 and a deletion mutant lacking the endonuclease domain (Δendo) were expressed in bacteria, purified by nickel-agarose chromatography and stained with Coomassie following SDS-PAGE (left panel). Increasing amounts of the wild-type and Δendo mutant (22 to 175 ng) were incubated with 500 ng of the 3.9 kb supercoiled plasmid pCR2 (Invitrogen) at 37° C. for 30. Reaction products were separated on a 1% agarose gel buffered in 1×TAE and containing 0.25 μg/ml ethidium bromide (right panel). Wild-type MED1, but not Δendo, generated nicked and linearized DNA. M, lambda/HindIII digest size standards; I, input plasmid DNA, incubated with reaction buffer only.

FIG. 11A shows a band reacting with the anti-hMSH2 antibody. Comigration with hMSH2 is detected by western blotting in anti-FLAG immunoprecipitates from Flag-MED1/f5 transfected cells but not control cells. FIG. 11B is a western blot of a parallel gel with the anti-FLAG antibody confirming expression of the Flag-MED1/f5 construct in transfected 293 cells. Co-immunoprecipitation of MED1 and MLH1 from human cells is shown in FIG. 11C. A band reacting with the anti-MLH1 antibody and comigrating with MLH1 is detected by western blotting in anti-hemagglutinin immunoprecipitates from HT-MED1/CMV5-transfected HEK-293 cells and not from CMV5-transfected control cells (upper panel). Western blotting of a parallel gel with the anti-hemagglutinin antibody confirms expression of the HT-MED1 construct in transfected HEK-293 cells (lower panel). Lysis buffers contained 0.5% NP-40 (lanes 1-4), 0.2% NP-40 (lanes 5-6) or 1% Triton X-100 (lanes 7-8).

FIG. 12 shows a series of MED1 mutations which have been isolated from colon cancer patients.

FIG. 16 shows the nucleotide sequence (SEQ ID NO: 5) of the mouse cDNA MED1 sequence assembled by juxtaposition of seven exons derived from the genomic clone MED1 MGL #3. Amino Acid Sequence=SEQ ID NO:29.

FIG. 17 shows a comparison of the predicted mouse MED1 protein sequence with the human MED1 protein sequence. Upper sequence: mouse MED1; lower sequence: human MED1. Identical amino acids between the two sequences are indicated by a line, similar amino acids by one (low similarity) or two dots (high similarity).

FIG. 18 shows the intron and exon sequences of the mouse genomic clone encoding MED1. Exon sequences are shown in upper case; intron sequences are shown in lower case. The splice donor (gt) and acceptor (ga) sites are in bold.

FIG. 19 shows the intron and exon sequences of the human genomic clone encoding MED1. Exon sequences are shown in upper case; intron sequences are shown in lower case. The splice donor (gt) and acceptor (ga) sites are in bold.

FIG. 29 is an autoradiogram which shows that MED1 has 3, $N^4$-ethenocytosine glycosylase activity. 3, $N^4$-ethenocytosine (E) is an exocyclic adduct of cytosine formed by vinyl chloride and other carcinogenic compounds, such as ethyl carbamate. The structure of E in comparison to cytosine is shown on the left panel. On the right panel, incubation of MED1 with an oligonucleotide substrate, containing E paired with G, unveiled a weak E glycosylase activity. The G:T oligonucleotide substrate constitutes a positive control. Arrows mark the expected migration of the substrate and product bands. For this experiment, the standard MED1 glycosylase assay was modified in that incubation with NaOH was substituted by incubation with purified AP-site endonuclease (APE), which cleaves the sugar-phosphate backbone at AP sites. This was necessary since E-containing oligonucleotides are sensitive to NaOH cleavage even in the absence of an AP site.

FIG. 30 is a schematic diagram illustrating detection of transition single nucleotide polymorphisms at CpG sites (CT-SNPs) with recombinant MED1 protein. Two CT-SNP alleles, allele 1 (CpG) and allele 2 (CpA) can be distinguished by annealing to a CT-SNP probe followed by incubation with MED1, NaOH treatment and electrophoretic separation. Only the heteroduplex containing a G:T mismatch (corresponding to allele 1) will generate a cleavage product, unlike the homoduplex (corresponding to allele 2).

DETAILED DESCRIPTION OF THE INVENTION

Figure 1:
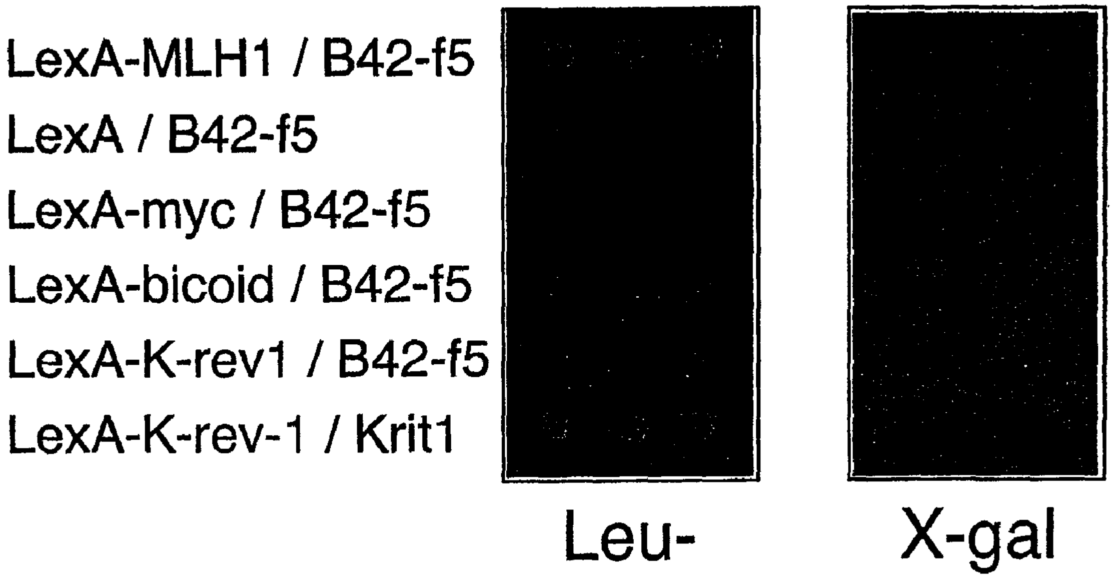
FIG. 1 depicts EGY191 yeast cells cotransformed with a combination of plasmids as indicated in the figure along with pSH18-34. The yeast so transformed were then selected on uracil-minus, histidine-minus tryptophan-minus glucose yeast medium to select for the presence of all plasmids. Individual transformants were replated either onto uracil-minus, histidine-minus, tryptophan-minus, leucine-minus galactose yeast medium to score activation of the LEU2 reporters (left panel) or onto uracil-minus, histidine-minus, tryptophan-minus galactose yeast medium containing 5-bromo-4-chloro-3-indolyl-β-D-galactopyranoside (X-gal) to score activation of the LacZ reporters (right panel). Growth on leucine-minus plates and blue-color formation on X-gal plates illustrate the specificity of the interaction between f5/MED1 and hMLH1. All interactions were galactose specific. The interaction shown between K-rev-1 and Krit1 represents a positive control.

Hereditary Non-Polyposis Colorectal Cancer (HNPCC), or Lynch Syndrome, is an autosomal dominant disorder characterized by early onset colorectal tumors. As noted above, tumors from HNPCC patients harbor a genome-wide DNA replication/repair defect, the hallmark of which is length instability of microsatellite repeat sequences. Patients affected by HNPCC carry a germline mutation in genes involved in DNA mismatch repair, a specialized system which handles base-base mismatches, short insertions/deletions and recombination-derived heteroduplexes (Kolodner, R. D., (1995) *Trends in Biochem. Sci.* 20:397-4053; Modrich and Lahue, (1996) *Annu. Rev. Biochem.* 65:101-133). The mismatch repair pathway contributes to mutational avoidance and genetic stability, thus performing a tumor suppressor function. Loss or inactivation of the wild type allele in somatic cells leads to a dramatic increase of the spontaneous mutation rate. This, in turn, results in the accumulation of mutations in other tumor suppressor genes and oncogenes, ultimately leading to neoplastic transformation (Bellacosa et al., (1996) *Am. J. of Med. Genetics* 62:353-364). Similarly to other genes involved in tumor suppression, mutations of mismatch repair genes can be detected in a subset of sporadic colonic and extracolonic cancers which exhibit microsatellite instability (Liu et al., 1996, supra).

Any one of five DNA mismatch repair genes (hMSH2, hMLH1, hPMS2, hMSH6 and hPMS1) is found to be mutated in the germline DNA of HNPCC patients (Liu et al., 1996, supra). These genes encode human homologues of the *E. coli* mismatch repair proteins MutS and MutL, which belong to the methyl-directed mismatch repair system (Kolodner, R. D., 1995, supra). Repair by this system involves 10 biochemical activities and is organized in 3 sequential steps of initiation, excision and resynthesis (Modrich, P., 1991) *Ann. Rev. Genet.* 25:229-253). During initiation, the mismatch is detected and a single-strand cut is made on the newly synthesized DNA strand which contains the mutation. Then, single-strand exonucleases (exo I, exo VII, RecJ) excise a span of about 1-2 kbp containing the mismatch and finally resynthesis by DNA polymerase III takes place. The products of the mutSLH genes mediate the initiation step. MutS detects and binds to the mismatch. Through an interaction with MutL, which likely functions as an interface with MutS, the single-strand endonuclease MutH is activated and cuts the DNA strand carrying the mutation (Modrich, P., 1991, supra).

A similar biochemical pathway has been identified in eukaryotic cells, and it is also characterized by strand-specificity and bidirectional excision capability (Fang and Modrich, (1993) *J. Biol. Chem.* 268:11838-11844). In the bacterial system, MutH has the pivotal role of identifying the newly synthesized strand, i.e. the strand carrying the mutation. Without this function there would be a 50% chance of initiating repair on the parental strand, thereby stabilizing the mutation. MutH identifies and cleaves the new strand by virtue of its transient lack of adenine methylation at d(GATC) sites (Modrich, P., 1991, supra). Despite its crucial function, homologues of MutH, i.e., eukaryotic mismatch repair endonucleases, have not been identified to date. Furthermore, the molecular determinants of strand discrimination in eukaryotic cells—which lack d(GATC) methylation—are not presently known (Kolodner, R. D., 1995, supra; Modrich and Lahue, 1996, supra). In order to gain insight into the mechanisms of strand recognition, it is essential to identify the eukaryotic functional homologue of the MutH endonuclease. Due to its proposed central role in mismatch repair, inactivation of this enzyme could be responsible for at least some cases of HNPCC.

As mentioned previously, aberrant DNA methylation may also play a role in Fragile X Syndrome. After semi-conservative replication of DNA, the mismatch repair system is able to use the conserved strand as a template to correct mismatches resulting from replication errors which are by definition in the newly synthesized strand. DNA replication results in a transient state of hemimethylation in which methylation occurs only on the template strand. In Fragile X Syndrome, the CGG repeats and subsequent expansion of these repeats may be triggered by undermethylation leading to misdirection of DNA mismatch repair. MED1 encoded proteins may play a pivotal role in this aberrant DNA replication/repair event. As mentioned earlier, this could also be the case for other diseases associated with repeat expansion, such as myotonic dystrophy, Huntington's disease, spino-cerebellar ataxias and Kennedy's disease.

The genomic and cDNA cloning of MED1, the DNA molecule of the invention, which encodes a protein bearing homology to bacterial endonucleases and glycosylases/lyases is described in detail below. Analysis of the predicted amino acid sequence of the MED1 protein suggests a putative mechanism of strand recognition based on cytosine methylation at CpG sites. Indeed as confirmed by the data presented herein, MED1 is a mismatch specific glycosylase. Like other DNA recognition and repair genes which are mutated in HNPCC as well as in sporadic cancers with microsatellite instability, MED1 is a candidate nucleic acid for cancer genetic testing, both in HNPCC families and in sporadic cancers with microsatellite instability. Aberrant MED1 activity may also be associated with Fragile X Syndrome and other diseases characterized by triplet repeat expansion.

MED1 possesses thymine and uracil glycosylase activity that specifically removes thymine and uracil from G:T and G:U mismatches, respectively. Thus MED1 has functions analogous to those of human thymine glycosylase TDG and its bacterial homolog, mismatch uracil glycosylase (MUG). Assays for assessing the glycosylase activity of MED1 isolated from patients are disclosed herein. Such assays may be used to assess for genetic mutations in MED1-encoding nucleic acids. Altered MED1 glycosylase activity may be associated with certain forms of cancer. Glycosylase assays based on MED1 may also be used to assess for genetic mutations/polymorphisms in nucleic acids as described further hereinbelow.

Based on its G:T mismatch-specific glycosylase activity at CpG sites, MED1 appears to counteract mutagenesis by spontaneous deamination of 5-methylcytosine to thymine, which indeed would give rise to a G:T mismatch. Deamination of 5-methylcytosine to thymine is a process known to occur spontaneously at measurable rates and constitutes a major mutagenic process. Indeed, CpG sites constitute mutational hot spots in many genes, including the tumor suppressor gene p53. Deamination of 5-methylcytosine, if not repaired, would lead to C>T and G>A transitions in the next round of DNA replcication. These transitions at CpG sites are the most frequent mutations in human cancer, including nearly 50% of all germline p53 mutations in Li-Fraumeni syndrome families and nearly 50% of all somatic p53 mutations in colorectal cancer. Thus, in another aspect, the invention provides methods for detection of transition single-nucleotide polymorphism at CpG sites (CT-SNPs) between known DNA sequences and those isolated from patients.

Determination of the sequence and chromosomal location of MED1 facilitates LOH analysis of patient DNA to assess for the presence or absence of MED1 encoding nucleic acids. As mentioned previously, loss of MED1 expression may abrogate repair of mismatched DNA which in turn, may ultimately give rise to neoplasia.

I. Preparation of MED1-Encoding Nucleic Acid Molecules, MED1 Proteins, and Antibodies Thereto A. Nucleic Acid Molecules Nucleic acid molecules encoding the MED1 protein of the invention may be prepared by two general methods: (1) Synthesis from appropriate nucleotide triphosphates, or (2) Isolation from biological sources. Both methods utilize protocols well known in the art.

The availability of nucleotide sequence information, such as the full length cDNA having Sequence I.D. No. 1, enables preparation of an isolated nucleic acid molecule of the invention by oligonucleotide synthesis. Synthetic oligonucleotides may be prepared by the phosphoramidite method employed in the Applied Biosystems 38A DNA Synthesizer or similar devices. The resultant construct may be purified according to methods known in the art, such as high performance liquid chromatography (HPLC). Long, double-stranded polynucleotides, such as a DNA molecule of the present invention, must be synthesized in stages, due to the size limitations inherent in current oligonucleotide synthetic methods. Thus, for example, a 2.4 kb double-stranded molecule may be synthesized as several smaller segments of appropriate complementarity. Complementary segments thus produced may be annealed such that each segment possesses appropriate cohesive termini for attachment of an adjacent segment. Adjacent segments may be ligated by annealing cohesive termini in the presence of DNA ligase to construct an entire 2.4 kb double-stranded molecule. A synthetic DNA molecule so constructed may then be cloned and amplified in an appropriate vector.

Nucleic acid sequences encoding MED1 may be isolated from appropriate biological sources using methods known in the art. In a preferred embodiment, a cDNA clone is isolated from a cDNA expression library of human origin. In an alternative embodiment, utilizing the sequence information provided by the cDNA sequence, genomic clones encoding MED1 may be isolated. Alternatively, cDNA or genomic clones having homology with MED1 may be isolated from other species, such as mouse, using oligonucleotide probes corresponding to predetermined sequences within the MED1 gene.

In accordance with the present invention, nucleic acids having the appropriate level of sequence homology with the protein coding region of Sequence I.D. No. 1 may be identified by using hybridization and washing conditions of appropriate stringency. For example, hybridizations may be performed, according to the method of Sambrook et al., (supra) using a hybridization solution comprising: 5×SSC, 5× Denhardt's reagent, 0.5-1.0% SDS, 100 μg/ml denatured, fragmented salmon sperm DNA, 0.05% sodium pyrophosphate and up to 50% formamide. Hybridization is carried out at 37-42° C. for at least six hours. Following hybridization, filters are washed as follows: (1) 5 minutes at room temperature in 2×SSC and 0.5-1% SDS; (2) 15 minutes at room temperature in 2×SSC and 0.1% SDS; (3) 30 minutes-1 hour at 37° C. in 1×SSC and 1% SDS; (4) 2 hours at 42-650 in 1×SSC and 1% SDS, changing the solution every 30 minutes.

One common formula for calculating the stringency conditions required to achieve hybridization between nucleic acid molecules of a specified sequence homology is (Sambrook et al., 1989):

$T_m$=81.5° C.+16.6 Log [Na+]+0.41 (% G+C)-0.63 (% formamide)−600/#bp in duplex

As an illustration of the above formula, using [Na+]=[0.368] and 50% formamide, with GC content of 42% and an average probe size of 200 bases, the $T_m$ is 57° C. The $T_m$ of a DNA duplex decreases by 1-1.5° C. with every 1% decrease in homology. Thus, targets with greater than about 75% sequence identity would be observed using a hybridization temperature of 42° C. Such a sequence would be considered substantially homologous to the nucleic acid sequence of the present invention.

Nucleic acids of the present invention may be maintained as DNA in any convenient cloning vector. In a preferred embodiment, clones are maintained in a plasmid cloning/expression vector, such as pBluescript (Stratagene, La Jolla, Calif.), which is propagated in a suitable *E. coli* host cell. Genomic clones of the invention encoding the human or mouse MED1 gene may be maintained in lambda phage FIX II (Stratagene).

MED1-encoding nucleic acid molecules of the invention include cDNA, genomic DNA, RNA, and fragments thereof which may be single- or double-stranded. Thus, this invention provides oligonucleotides (sense or antisense strands of DNA or RNA) having sequences capable of hybridizing with at least one sequence of a nucleic acid molecule of the present invention, such as selected segments of the cDNA having Sequence I.D. No. 1. Such oligonucleotides are useful as probes for detecting or isolating MED1 genes.

It will be appreciated by persons skilled in the art that variants (e.g., allelic variants) of these sequences exist in the human population, and must be taken into account when designing and/or utilizing oligos of the invention. Accordingly, it is within the scope of the present invention to encompass such variants, with respect to the MED1 sequences disclosed herein or the oligos targeted to specific locations on the respective genes or RNA transcripts. With respect to the inclusion of such variants, the term "natural allelic variants" is used herein to refer to various specific nucleotide sequences and variants thereof that would occur in a human population.

Genetic polymorphisms giving rise to conservative or neutral amino acid substitutions in the encoded protein are examples of such variants. Additionally, the term "substantially complementary" refers to oligo sequences that may not be perfectly matched to a target sequence, but the mismatches do not materially affect the ability of the oligo to hybridize with its target sequence under the conditions described.

Thus, the coding sequence may be that shown in Sequence I.D. No. 1, or it may be a mutant, variant, derivative or allele of this sequence. The sequence may differ from that shown by a change which is one or more of addition, insertion, deletion and substitution of one or more nucleotides of the sequence shown. Changes to a nucleotide sequence may result in an amino acid change at the protein level, or not, as determined by the genetic code.

Thus, nucleic acid according to the present invention may include a sequence different from the sequence shown in Sequence I.D. No. 1 yet encode a polypeptide with the same amino acid sequence.

On the other hand, the encoded polypeptide may comprise an amino acid sequence which differs by one or more amino acid residues from the amino acid sequence shown in Sequence I.D. No. 2. Nucleic acid encoding a polypeptide which is an amino acid sequence mutant, variant, derivative or allele of the sequence shown in Sequence I.D. No. 2 is further provided by the present invention. Nucleic acid encoding such a polypeptide may show greater than 60% homology with the coding sequence shown in Sequence I.D. No. 1, greater than about 70% homology, greater than about 80% homology, greater than about 90% homology or greater than about 95% homology.

Also within the scope of the invention are antisense oligonucleotide sequences based on the MED1 nucleic acid sequences described herein. Antisense oligonucleotides may be designed to hybridize to the complementary sequence of nucleic acid, pre-mRNA or mature mRNA, interfering with the production of polypeptides encoded by a given DNA sequence (e.g. either native MED1 polypeptide or a mutant form thereof), so that its expression is reduced or prevented altogether. In addition to the MED1 coding sequence, antisense techniques can be used to target control sequences of the MED1 gene, e.g. in the 5' flanking sequence of the MED1 coding sequence, whereby the antisense oligonucleotides can interfere with MED1 control sequences. The construction of antisense sequences and their use is described in Peyman and Ulman, Chemical Reviews, 90:543-584, (1990), Crooke, Ann. Rev. Pharmacol. Toxical., 32:329-376, (1992), and Zamecnik and Stephenson, Proc. Natl. Acad. Sci., 75:280-284, (1974).

The present invention provides a method of obtaining nucleic acid of interest, the method including hybridization of a probe having part or all of the sequence shown in Sequence I.D. No. 1 or a complementary sequence, to target nucleic acid. Hybridization is generally followed by identification of successful hybridization and isolation of nucleic acid which has hybridized to the probe, which may involve one or more steps of PCR.

Such oligonucleotide probes or primers, as well as the full-length sequence (and mutants, alleles, variants, and derivatives) are useful in screening a test sample containing nucleic acid for the presence of alleles, mutants or variants, especially those that confer susceptibility or predisposition to cancers, the probes hybridizing with a target sequence from a sample obtained from the individual being tested. The conditions of the hybridization can be controlled to minimize non-specific binding, and preferably stringent to moderately stringent hybridization conditions are used. The skilled person is readily able to design such probes, label them and devise suitable conditions for hybridization reactions, assisted by textbooks such as Sambrook et al (1989) and Ausubel et al (1992).

In some preferred embodiments, oligonucleotides according to the present invention that are fragments of the sequences shown in Sequence I.D. No. 1 or Sequence I.D. No. 5, or any allele associated with cancer susceptibility, are at least about 10 nucleotides in length, more preferably at least 15 nucleotides in length, more preferably at least about 20 nucleotides in length. Such fragments themselves individually represent aspects of the present invention. Fragments and other oligonucleotides may be used as primers or probes as discussed but may also be generated (e.g. by PCR) in methods concerned with determining the presence in a test sample of a sequence indicative of cancer susceptibility.

Methods involving use of nucleic acid in diagnostic and/or prognostic contexts, for instance in determining susceptibility to cancer, and other methods concerned with determining the presence of sequences indicative of cancer susceptibility are discussed below.

Nucleic acid according to the present invention may be used in methods of gene therapy, for instance in treatment of individuals with the aim of preventing or curing (wholly or partially) cancer. This too is discussed below.

B. Proteins

MED1 protein demonstrates methyl-CpG DNA binding and glycosylase activity. A full-length MED1 protein of the present invention may be prepared in a variety of ways, according to known methods. The protein may be purified from appropriate sources, e.g., transformed bacterial or animal cultured cells or tissues, by immunoaffinity purification. However, this is not a preferred method due to the low amount of protein likely to be present in a given cell type at any time. The availability of nucleic acid molecules encoding MED1 enables production of the protein using in vitro expression methods known in the art. For example, a cDNA or gene may be cloned into an appropriate in vitro transcription vector, such as pSP64 or pSP65 for in vitro transcription, followed by cell-free translation in a suitable cell-free translation system, such as wheat germ or rabbit reticulocyte lysates. In vitro transcription and translation systems are commercially available, e.g., from Promega Biotech, Madison, Wis. or BRL, Rockville, Md.

Alternatively, according to a preferred embodiment, larger quantities of MED1 may be produced by expression in a suitable prokaryotic or eukaryotic system. For example, part or all of a DNA molecule, such as the cDNA having Sequence I.D. No. 1, may be inserted into a plasmid vector adapted for expression in a bacterial cell, such as *E. coli*. Such vectors comprise the regulatory elements necessary for expression of the DNA in the host cell (e.g. *E. coli*) positioned in such a manner as to permit expression of the DNA in the host cell. Such regulatory elements required for expression include promoter sequences, transcription initiation sequences and, optionally, enhancer sequences.

The MED1 produced by gene expression in a recombinant prokaryotic or eukaryotic system may be purified according to methods known in the art. In a preferred embodiment, a commercially available expression/secretion system can be used, whereby the recombinant protein is expressed and thereafter secreted from the host cell, to be easily purified from the surrounding medium. If expression/secretion vectors are not used, an alternative approach involves purifying the recombinant protein by affinity separation, such as by immunological interaction with antibodies that bind specifically to the recombinant protein or nickel columns for isolation of recombinant proteins tagged with 6-8 histidine residues at their N-terminus or C-terminus. Alternative tags may comprise the FLAG epitope or the hemagglutinin epitope. Such methods are commonly used by skilled practitioners.

The MED1 proteins of the invention, prepared by the aforementioned methods, may be analyzed according to standard procedures. For example, such proteins may be subjected to amino acid sequence analysis, according to known methods.

As discussed above, a convenient way of producing a polypeptide according to the present invention is to express nucleic acid encoding it, by use of the nucleic acid in an expression system. The use of expression systems has reached an advanced degree of sophistication today.

Accordingly, the present invention also encompasses a method of making a polypeptide (as disclosed), the method including expression from nucleic acid encoding the polypeptide (generally nucleic acid according to the invention). This may conveniently be achieved by growing a host cell in culture, containing such a vector, under appropriate conditions which cause or allow production of the polypeptide. Polypeptides may also be produced in in vitro systems, such as reticulocyte lysate.

Polypeptides which are amino acid sequence variants, alleles, derivatives or mutants are also provided by the present invention. A polypeptide which is a variant, allele, derivative, or mutant may have an amino acid sequence that differs from that given in Sequence I.D. No. 2 by one or more of addition, substitution, deletion and insertion of one or more amino acids. Preferred such polypeptides have MED1 function, that is to say have one or more of the following properties: methyl-CpG DNA binding activity; glycosylase activity; binding to MLH1; immunological cross-reactivity with an antibody reactive with the polypeptide for which the sequence is given in Sequence I.D. No. 2; sharing an epitope with the polypeptide for which the sequence is given in Sequence I.D. No. 2 (as determined for example by immunological cross-reactivity between the two polypeptides.

A polypeptide which is an amino acid sequence variant, allele, derivative or mutant of the amino acid sequence shown in Sequence I.D. No. 2 may comprise an amino acid sequence which shares greater than about 35% sequence identity with the sequence shown, greater than about 40%, greater than about 50%, greater than about 60%, greater than about 70%, greater than about 80%, greater than about 90% or greater than about 95%. Particular amino acid sequence variants may differ from that shown in Sequence I.D. No. 2 by insertion, addition, substitution or deletion of 1 amino acid, 2, 3, 4, 5-10, 10-20, 20-30, 30-40, 40-50, 50-100, 100-150, or more than 150 amino acids.

A polypeptide according to the present invention may be used in screening for molecules which affect or modulate its activity or function. Such molecules may be useful in a therapeutic (possibly including prophylactic) context.

The present invention also provides antibodies capable of immunospecifically binding to proteins of the invention. Polyclonal antibodies directed toward MED1 may be prepared according to standard methods. In a preferred embodiment, monoclonal antibodies are prepared, which react immunospecifically with various epitopes of MED1. Monoclonal antibodies may be prepared according to general methods of Köhler and Milstein, following standard protocols. Polyclonal or monoclonal antibodies that immunospecifically interact with MED1 can be utilized for identifying and purifying such proteins. For example, antibodies may be utilized for affinity separation of proteins with which they immunospecifically interact. Antibodies may also be used to immunoprecipitate proteins from a sample containing a mixture of proteins and other biological molecules. Other uses of anti-MED1 antibodies are described below.

Antibodies according to the present invention may be modified in a number of ways. Indeed the term "antibody" should be construed as covering any binding substance having a binding domain with the required specificity. Thus, the invention covers antibody fragments, derivatives, functional equivalents and homologues of antibodies, including synthetic molecules and molecules whose shape mimics that of an antibody enabling it to bind an antigen or epitope.

Exemplary antibody fragments, capable of binding an antigen or other binding partner, are Fab fragment consisting of the VL, VH, C1 and CH1 domains; the Fd fragment consisting of the VH and CH1 domains; the Fv fragment consisting of the VL and VH domains of a single arm of an antibody; the dAb fragment which consists of a VH domain; isolated CDR regions and F(ab')2 fragments, a bivalent fragment including two Fab fragments linked by a disulphide bridge at the hinge region. Single chain Fv fragments are also included.

Humanized antibodies in which CDRs from a non-human source are grafted onto human framework regions, typically with alteration of some of the framework amino acid residues, to provide antibodies which are less immunogenic than the parent non-human antibodies, are also included within the present invention.

II. Uses of MED1-Encoding Nucleic Acids, MED1 Proteins and Antibodies Thereto

MED1 appears to be an important DNA repair enzyme which may play a role in mismatch repair. Mutations in MED1 are associated with certain forms of colon, pancreatic and endometrial cancer. The MED1 molecules of the invention may be used to advantage in genetic screening assays to identify those patients that may be at risk. Screening assays may also be developed which assess aberrant MED1 activity associated with Fragile X syndrome and other diseases characterized by triplet repeat expansion. Due to its methyl-CpG binding domain, MED1 might be useful in the analysis of genome methylation and of methylation-mediated DNA transcription, replication and repair (for instance, by binding to methylated and non-methylated DNA in a differential manner). Due to its endonuclease and/or glycosylase activity, MED1 is expected to be useful in the context of DNA manipulation technology. The employment of MED1 would be of particular interest in the area of mutation detection. Other endonucleases and glycosylases have been successfully used to detect mutations based on recognition of cleavage products of heteroduplex intermediates carrying mismatches (Mashal R. D., Koontz J. and Sklaar J. Nature Genet. 9: 177-183, 1995; Smith J. and Modrich P. Proc. Natl. Acad. Sci. USA 93: 4374-4379, 1996; Angelis et al., Electrophoresis 20:2133-2138, 1999; Bazar et al., Electrophoresis 20:1141-1148, 1999; Vaughan et al., Genet. Anal. 14:169-175, 1999).

Additionally, MED1 nucleic acids, proteins and antibodies thereto, according to this invention, may be used as a research tool to identify other proteins that are intimately involved in DNA recognition and repair reactions. Biochemical elucidation of the DNA recognition and repair capacity of MED1 will facilitate the development of these novel screening assays for assessing a patient's propensity for cancer and genetic disease.

A. MED1-Encoding Nucleic Acids

MED1-encoding nucleic acids may be used for a variety of purposes in accordance with the present invention. MED1-encoding DNA, RNA, or fragments thereof may be used as probes to detect the presence of and/or expression of genes encoding MED1 proteins. Methods in which MED1-encoding nucleic acids may be utilized as probes for such assays include, but are not limited to: (1) in situ hybridization; (2) Southern hybridization (3) northern hybridization; and (4) assorted amplification reactions such as polymerase chain reactions (PCR).

The MED1-encoding nucleic acids of the invention may also be utilized as probes to identify related genes from other animal species. As is well known in the art, hybridization stringencies may be adjusted to allow hybridization of nucleic acid probes with complementary sequences of varying degrees of homology. Thus, MED1-encoding nucleic acids may be used to advantage to identify and characterize other genes of varying degrees of relation to MED1, thereby enabling further characterization of the DNA repair system. Additionally, they may be used to identify genes encoding proteins that interact with MED1 (e.g., by the "interaction trap" technique), which should further accelerate identification of the components involved in DNA repair.

Nucleic acid molecules, or fragments thereof, encoding MED1 may also be utilized to control the production of MED1, thereby regulating the amount of protein available to participate in DNA repair reactions. Alterations in the physiological amount of MED1 protein may dramatically affect the activity of other protein factors involved in DNA repair.

The availability of MED1 encoding nucleic acids enables the production of strains of laboratory mice carrying part or all of the MED1 gene or mutated sequences thereof. Such mice may provide an in vivo model for cancer. Alternatively, the MED1 sequence information provided herein enables the production of knockout mice in which the endogenous gene encoding MED1 has been specifically inactivated. Methods of introducing transgenes in laboratory mice are known to those of skill in the art. Three common methods include: 1. integration of retroviral vectors encoding the foreign gene of interest into an early embryo; 2. injection of DNA into the pronucleus of a newly fertilized egg; and 3. the incorporation of genetically manipulated embryonic stem cells into an early embryo. Production of the transgenic mice described above will facilitate the molecular elucidation of the role MED1 plays in embryonic development and cancer.

A transgenic mouse carrying the human MED1 gene is generated by direct replacement of the mouse MED1 gene with the human gene. These transgenic animals are useful for drug screening studies as animal models for human diseases and for eventual treatment of disorders or diseases associated with biological activities modulated by MED1. A transgenic animal carrying a "knock out" of MED1 is useful for assessing the role of MED1 in maintaining DNA fidelity.

As a means to define the role that MED1 plays in mammalian systems, mice may be generated that cannot make MED1 protein because of a targeted mutational disruption of the MED1 gene.

The term "animal" is used herein to include all vertebrate animals, except humans. It also includes an individual animal in all stages of development, including embryonic and fetal stages. A "transgenic animal" is any animal containing one or more cells bearing genetic information altered or received, directly or indirectly, by deliberate genetic manipulation at the subcellular level, such as by targeted recombination or microinjection or infection with recombinant virus. The term "transgenic animal" is not meant to encompass classical cross-breeding or in vitro fertilization, but rather is meant to encompass animals in which one or more cells are altered by, or receive a recombinant DNA molecule. This molecule may be specifically targeted to a defined genetic locus, be randomly integrated within a chromosome, or it may be extra-chromosomally replicating DNA. The term "germ cell line transgenic animal" refers to a transgenic animal in which the genetic alteration or genetic information was introduced into a germ line cell, thereby conferring the ability to transfer the genetic information to offspring. If such offspring, in fact, possess some or all of that alteration or genetic information, then they, too, are transgenic animals.

The alteration or genetic information may be foreign to the species of animal to which the recipient belongs, or foreign only to the particular individual recipient, or may be genetic information already possessed by the recipient. In the last case, the altered or introduced gene may be expressed differently than the native gene.

The altered MED1 gene generally should not fully encode the same MED1 protein native to the host animal and its expression product should be altered to a minor or great degree, or absent altogether. However, it is conceivable that a more modestly modified MED1 gene will fall within the compass of the present invention if it is a specific alteration.

The DNA used for altering a target gene may be obtained by a wide variety of techniques that include, but are not limited to, isolation from genomic sources, preparation of cDNAs from isolated mRNA templates, direct synthesis, or a combination thereof.

A type of target cell for transgene introduction is the embryonal stem cell (ES). ES cells may be obtained from pre-implantation embryos cultured in vitro (Evans et al., (1981) Nature 292:154-156; Bradley et al., (1984) Nature 309:255-258; Gossler et al., (1986) Proc. Natl. Acad. Sci. 83:9065-9069). Transgenes can be efficiently introduced into the ES cells by standard techniques such as DNA transfection or by retrovirus-mediated transduction. The resultant transformed ES cells can thereafter be combined with blastocysts from a non-human animal. The introduced ES cells thereafter colonize the embryo and contribute to the germ line of the resulting chimeric animal.

One approach to the problem of determining the contributions of individual genes and their expression products is to use isolated MED1 genes to selectively inactivate the wild-type gene in totipotent ES cells (such as those described above) and then generate transgenic mice. The use of gene-targeted ES cells in the generation of gene-targeted transgenic mice was described, and is reviewed elsewhere (Frohman et al., (1989) Cell 56:145-147; Bradley et al., (1992) Bio/Technology 10:534-539).

Techniques are available to inactivate or alter any genetic region to a mutation desired by using targeted homologous recombination to insert specific changes into chromosomal alleles. However, in comparison with homologous extrachromosomal recombination, which occurs at a frequency approaching 100%, homologous plasmid-chromosome recombination was originally reported to only be detected at frequencies between $10^{-6}$ and $10^{-3}$. Nonhomologous plasmid-chromosome interactions are more frequent, occurring at levels $10^5$-fold to $10^2$-fold greater than comparable homologous insertion.

To overcome this low proportion of targeted recombination in murine ES cells, various strategies have been developed to detect or select rare homologous recombinants. One approach for detecting homologous alteration events uses the polymerase chain reaction (PCR) to screen pools of transformant cells for homologous insertion, followed by screening of individual clones. Alternatively, a positive genetic selection approach has been developed in which a marker gene is constructed which will only be active if homologous insertion occurs, allowing these recombinants to be selected directly. One of the most powerful approaches developed for selecting homologous recombinants is the positive-negative selection (PNS) method developed for genes for which no direct selection of the alteration exists. The PNS method is more efficient for targeting genes which are not expressed at high levels because the marker gene has its own promoter. Non-homologous recombinants are selected against by using the Herpes Simplex virus thymidine kinase (HSV-TK) gene and selecting against its nonhomologous insertion with effective herpes drugs such as gancyclovir (GANC) or (1-(2-deoxy-2-fluoro-B-D arabinofluranosyl)-5-iodouracil, (FIAU). By this counter selection, the number of homologous recombinants in the surviving transformants can be increased.

As used herein, a "targeted gene" or "knock-out" is a DNA sequence introduced into the germline or a non-human animal by way of human intervention, including but not limited to, the methods described herein. The targeted genes of the invention include DNA sequences which are designed to specifically alter cognate endogenous alleles.

Methods of use for the transgenic mice of the invention are also provided herein. Therapeutic agents for the treatment or prevention of cancer may be screened in studies using MED1 transgenic mice.

In another embodiment of the invention, MED1 knockout mice may be used to produce an array of monoclonal antibodies specific for MED1 protein.

As described above, MED1-encoding nucleic acids are also used to advantage to produce large quantities of substantially pure MED1 protein, or selected portions thereof.

B. MED1 Protein and Antibodies

Purified MED1, or fragments thereof, may be used to produce polyclonal or monoclonal antibodies which also may serve as sensitive detection reagents for the presence and accumulation of MED1 (or complexes containing MED1) in mammalian cells. Recombinant techniques enable expression of fusion proteins containing part or all of the MED1 protein. The full length protein or fragments of the protein may be used to advantage to generate an array of monoclonal antibodies specific for various epitopes of the protein, thereby providing even greater sensitivity for detection of the protein in cells.

Polyclonal or monoclonal antibodies immunologically specific for MED1 may be used in a variety of assays designed to detect and quantitate the protein. Such assays include, but are not limited to: (1) flow cytometric analysis; (2) immunochemical localization of MED1 in tumor cells; and (3) immunoblot analysis (e.g., dot blot, Western blot) of extracts from various cells. Additionally, as described above, anti-MED1 antibodies can be used for purification of MED1 (e.g., affinity column purification, immunoprecipitation).

From the foregoing discussion, it can be seen that MED1-encoding nucleic acids, MED1 expressing vectors, MED1 proteins and anti-MED1 antibodies of the invention can be used to detect MED1 gene expression and alter MED1 protein accumulation for purposes of assessing the genetic and protein interactions involved in the recognition and repair of DNA damage.

Exemplary approaches for detecting MED1 nucleic acid or polypeptides/proteins include:

a) comparing the sequence of nucleic acid in the sample with the MED1 nucleic acid sequence to determine whether the sample from the patient contains mutations; or b) determining the presence, in a sample from a patient, of the polypeptide encoded by the MED1 gene and, if present, determining whether the polypeptide is full length, and/or is mutated, and/or is expressed at the normal level; or c) using DNA restriction mapping to compare the restriction pattern produced when a restriction enzyme cuts a sample of nucleic acid from the patient with the restriction pattern obtained from normal MED1 gene or from known mutations thereof; or, d) using a specific binding member capable of binding to a MED1 nucleic acid sequence (either normal sequence or known mutated sequence), the specific binding member comprising nucleic acid hybridizable with the MED1 sequence, or substances comprising an antibody domain with specificity for a native or mutated MED1 nucleic acid sequence or the polypeptide encoded by it, the specific binding member being labelled so that binding of the specific binding member to its binding partner is detectable; or, e) using PCR involving one or more primers based on normal or mutated MED1 gene sequence to screen for normal or mutant MED1 gene in a sample from a patient.

A "specific binding pair" comprises a specific binding member (sbm) and a binding partner (bp) which have a particular specificity for each other and which in normal conditions bind to each other in preference to other molecules. Examples of specific binding pairs are antigens and antibodies, ligands and receptors and complementary nucleotide sequences. The skilled person is aware of many other examples and they do not need to be listed here. Further, the term "specific binding pair" is also applicable where either or both of the specific binding member and the binding partner comprise a part of a large molecule. In embodiments in which the specific binding pair comprises nucleic acid sequences, they will be of a length to hybridize to each other under conditions of the assay, preferably greater than 10 nucleotides long, more preferably greater than 15 or 20 nucleotides long.

In most embodiments for screening for cancer susceptibility alleles, the MED1 nucleic acid in the sample will initially be amplified, e.g. using PCR, to increase the amount of the analyte as compared to other sequences present in the sample. This allows the target sequences to be detected with a high degree of sensitivity if they are present in the sample. This initial step may be avoided by using highly sensitive array techniques that are becoming increasingly important in the art.

The identification of the MED1 gene and its association with cancer paves the way for aspects of the present invention to provide the use of materials and methods, such as are disclosed and discussed above, for establishing the presence or absence in a test sample of a variant form of the gene, in particular an allele or variant specifically associated with cancer, especially colorectal, pancreatic, or endometrial cancer. This may be for diagnosing a predisposition of an individual to cancer. It may be for diagnosing cancer of a patient with the disease as being associated with the gene.

This allows for planning of appropriate therapeutic and/or prophylactic measures, permitting stream-lining of treatment. The approach further stream-lines treatment by targeting those patients most likely to benefit.

According to another aspect of the invention, methods of screening drugs for cancer therapy to identify suitable drugs for restoring MED1 product functions are provided. A major problem in cancer treatment is the development of drug resistance or ionizing radiation resistance by the tumor cells which eventually leads to failure of therapy. Recent studies have revealed that inactivation of DNA mismatch repair is an important mechanism of resistance to many chemotherapeutic drugs used in the clinic (Fink D., Aebi S, and Howell S. B. (1998). Clinical Cancer Res. 4: 1-6). In fact, a functional mismatch repair system appears to be required for killing by many alkylating agents and platinum compounds. Resistance/tolerance to those agents is associated with loss of expression or function of mismatch repair genes: in the absence of a functional mismatch repair system, DNA damage accumulates but fails to trigger apoptosis (Fink D., Aebi S, and Howell S. B. (1998), supra). Defects in DNA mismatch repair genes (hMLH1, hPMS2, hMSH2 and hMSH6) have been found in cell lines and primary tumors resistant to those chemotherapeutic agents. Thus, loss of MED1 function/expression may be associated with changes in tumor drug sensitivity. Restoration of MED1 function by gene transfer or by pharmacological means would be expected to modulate resistance to treatment.

The MED1 polypeptide or fragment employed in drug screening assays may either be free in solution, affixed to a solid support or within a cell. One method of drug screening utilizes eukaryotic or prokaryotic host cells which are stably transformed with recombinant polynucleotides expressing the polypeptide or fragment, preferably in competitive binding assays. Such cells, either in viable or fixed form, can be used for standard binding assays. One may determine, for example, formation of complexes between a MED1 polypeptide or fragment and the agent being tested, or examine the degree to which the formation of a complex between a MED1 polypeptide or fragment and a known ligand is interfered with by the agent being tested.

Another technique for drug screening provides high throughput screening for compounds having suitable binding affinity to the MED1 polypeptides and is described in detail in Geysen, PCT published application WO 84/03564, published on Sep. 13, 1984. Briefly stated, large numbers of different, small peptide test compounds are synthesized on a solid substrate, such as plastic pins or some other surface. The peptide test compounds are reacted with MED1 polypeptide and washed. Bound MED1 polypeptide is then detected by methods well known in the art.

Purified MED1 can be coated directly onto plates for use in the aforementioned drug screening techniques. However, non-neutralizing antibodies to the polypeptide can be used as capture antibodies to immobilize the MED1 polypeptide on the solid phase.

This invention also contemplates the use of competitive drug screening assays in which neutralizing antibodies capable of specifically binding the MED1 polypeptide compete with a test compound for binding to the MED1 polypeptide or fragments thereof. In this manner, the antibodies can be used to detect the presence of any peptide which shares one or more antigenic determinants of the MED1 polypeptide.

A further technique for drug screening involves the use of host eukaryotic cell lines or cells (such as described above) which have a nonfunctional MED1 gene. These host cell lines or cells are defective at the MED1 polypeptide level. The host cell lines or cells are grown in the presence of drug compound. The rate of growth of the host cells is measured to determine if the compound is capable of regulating the growth of MED1 defective cells.

The goal of rational drug design is to produce structural analogs of biologically active polypeptides of interest or of small molecules with which they interact (e.g., agonists, antagonists, inhibitors) in order to fashion drugs which are, for example, more active or stable forms of the polypeptide, or which, e.g., enhance or interfere with the function of a polypeptide in vivo. See, e.g., Hodgson, (1991) Bio/Technology 9:19-21. In one approach, one first determines the three-dimensional structure of a protein of interest (e.g., MED1 polypeptide) or, for example, of the MED1-DNA complex, by x-ray crystallography, by nuclear magnetic resonance, by computer modeling or most typically, by a combination of approaches. Less often, useful information regarding the structure of a polypeptide may be gained by modeling based on the structure of homologous proteins. An example of rational drug design is the development of HIV protease inhibitors (Erickson et al., (1990) Science 249:527-533). In addition, peptides (e.g., MED1 polypeptide) may be analyzed by an alanine scan (Wells, (1991) Meth. Enzym. 202:390-411). In this technique, an amino acid residue is replaced by Ala, and its effect on the peptide's activity is determined. Each of the amino acid residues of the peptide is analyzed in this manner to determine the important regions of the peptide.

It is also possible to isolate a target-specific antibody, selected by a functional assay, and then to solve its crystal structure. In principle, this approach yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original molecule. The anti-id could then be used to identify and isolate peptides from banks of chemically or biologically produced banks of peptides. Selected peptides would then act as the pharmacore.

Thus, one may design drugs which have, e.g., improved MED1 polypeptide activity or stability or which act as inhibitors, agonists, antagonists, etc. of MED1 polypeptide activity. By virtue of the availability of cloned MED1 sequences, sufficient amounts of the MED1 polypeptide may be made available to perform such analytical studies as x-ray crystallography. In addition, the knowledge of the MED1 protein sequence provided herein will guide those employing computer modeling techniques in place of, or in addition to x-ray crystallography and nuclear magnetic resonance (NMR) spectroscopy.

III Therapeutics

A. Pharmaceuticals and Peptide Therapies

The MED1 polypeptides/proteins, antibodies, peptides and nucleic acids of the invention can be formulated in pharmaceutical compositions. These compositions may comprise, in addition to one of the above substances, a pharmaceutically acceptable excipient, carrier, buffer, stabilizer or other materials well known to those skilled in the art. Such materials should be non-toxic and should not interfere with the efficacy of the active ingredient. The precise nature of the carrier or other material may depend on the route of administration, e.g. oral, intravenous, cutaneous or subcutaneous, nasal, intramuscular, intraperitoneal routes.

Whether it is a polypeptide, antibody, peptide, nucleic acid molecule, small molecule or other pharmaceutically useful compound according to the present invention that is to be given to an individual, administration is preferably in a "prophylactically effective amount" or a "therapeutically effective amount" (as the case may be, although prophylaxis may be considered therapy), this being sufficient to show benefit to the individual.

B. Methods of Gene Therapy

As a further alternative, the nucleic acid encoding the authentic biologically active MED1 polypeptide could be used in a method of gene therapy, to treat a patient who is unable to synthesize the active "normal" polypeptide or unable to synthesize it at the normal level, thereby providing the effect elicited by wild-type MED1 and suppressing the occurrence of "abnormal" MED1 lacking the ability to perform or effect DNA repair.

Vectors such as viral vectors have been used in the prior art to introduce genes into a wide variety of different target cells. Typically the vectors are exposed to the target cells so that transformation can take place in a sufficient proportion of the cells to provide a useful therapeutic or prophylactic effect from the expression of the desired polypeptide. The transfected nucleic acid may be permanently incorporated into the genome of each of the targeted tumor cells, providing long lasting effect, or alternatively the treatment may have to be repeated periodically.

A variety of vectors, both viral vectors and plasmid vectors are known in the art, see U.S. Pat. No. 5,252,479 and WO 93/07282. In particular, a number of viruses have been used as gene transfer vectors, including papovaviruses, such as SV40, vaccinia virus, herpes viruses including HSV and EBV, and retroviruses. Many gene therapy protocols in the prior art have employed disabled murine retroviruses.

Gene transfer techniques which selectively target the MED1 nucleic acid to colorectal tissues are preferred. Examples of this include receptor-mediated gene transfer, in which the nucleic acid is linked to a protein ligand via polylysine, with the ligand being specific for a receptor present on the surface of the target cells.

The following examples are provided to illustrate certain embodiments of the invention. They are not intended to limit the invention in any way.

EXAMPLE I

The methods described below have been used to advantage to isolate the MED1 encoding nucleic acids of the invention.

A. Interaction Trap Screen, cDNA and Genomic DNA Isolation.

Yeast interaction trap screening (Gyuris et al., (1993) *Cell* 75:791-803; Golemis et al., (1996) Yeast Interaction Trap/Two Hybrid Systems to Identify Interacting Proteins, Unit 20.1.1-20.1.28 in *Current Protocols in Molecular Biology*, eds. Ausubel, F. M. et al., John Wiley & Sons, NY) was used to isolate cDNAs encoding proteins able to interact with hMLH1. The hMLH1 open reading frame was inserted into the polylinker of the pEG202 vector (Golemis et al., 1996, supra). The resulting "bait" construct pEG202-t-hMLH1 expresses the hMLH1 protein (amino acids 1-756) as a carboxyterminal fusion to the LexA DNA binding protein. *Saccharomyces cerevisiae* strain EGY191 (Estojak et al., (1995) *Mol. Cell. Bio.* 15:5820-5829) was transformed with the bait construct and with the LacZ reporter plasmid pSH18-34 (Golemis et al., 1996, supra).

The EGY191/pSH18-34/pEG202-t-hMLH1 cells were supertransformed with a human fetal brain cDNA library constructed in the vector pJG4-5. This vector directs the synthesis of proteins fused to the B42 transcriptional activator domain (Ruden et al., (1991) *Nature* 350:25-252) and the expression is controlled by the galactose-inducible GAL1 promoter. Approximately $4\times10^5$ independent transformants were obtained in yeast and used for screening. For selection of the positive interactors, the supertransformed cells were cultured on leucine-minus/galactose solid medium. Colonies growing on this medium after 3-5 days incubation were subcultured on leucine-minus or X-Gal media containing either glucose or galactose as a carbon source. Twenty-two colonies growing on leucine-minus/galactose but not leucine-minus/glucose medium and turning blue on X-Gal/galactose but not X-Gal/glucose plates were further characterized.

Plasmid DNA encoding putative hMLH1 interactors was isolated from these colonies (clones f1 through f22), transferred first to KC8 and then to XL-1 blue *E. coli* strains, and sequenced. These and subsequent sequencing reactions were performed on double stranded DNA with the ABI automated sequencer 377 using dye terminator chemistry (Perkin Elmer). Sequence assembling and analysis was performed with the Genetics Computer Group software (Genetics Computer Group, 1994). Since the f5 clone (later named MED1) was shorter (0.8 kb 3' of B42) than the mRNA transcript detected in human tissues by Northern blot analysis (approximately 2.4 kb), a f5-derived probe was used to screen three additional cDNA lambda libraries. The libraries, derived from human fetal brain (Stratagene and Clontech) and from the ovarian cancer cell line C200 (gift of Drs. A. Godwin and G. Kruh), were screened following standard procedures as previously described (Bellacosa et al., 1994, supra).

Figure 13:
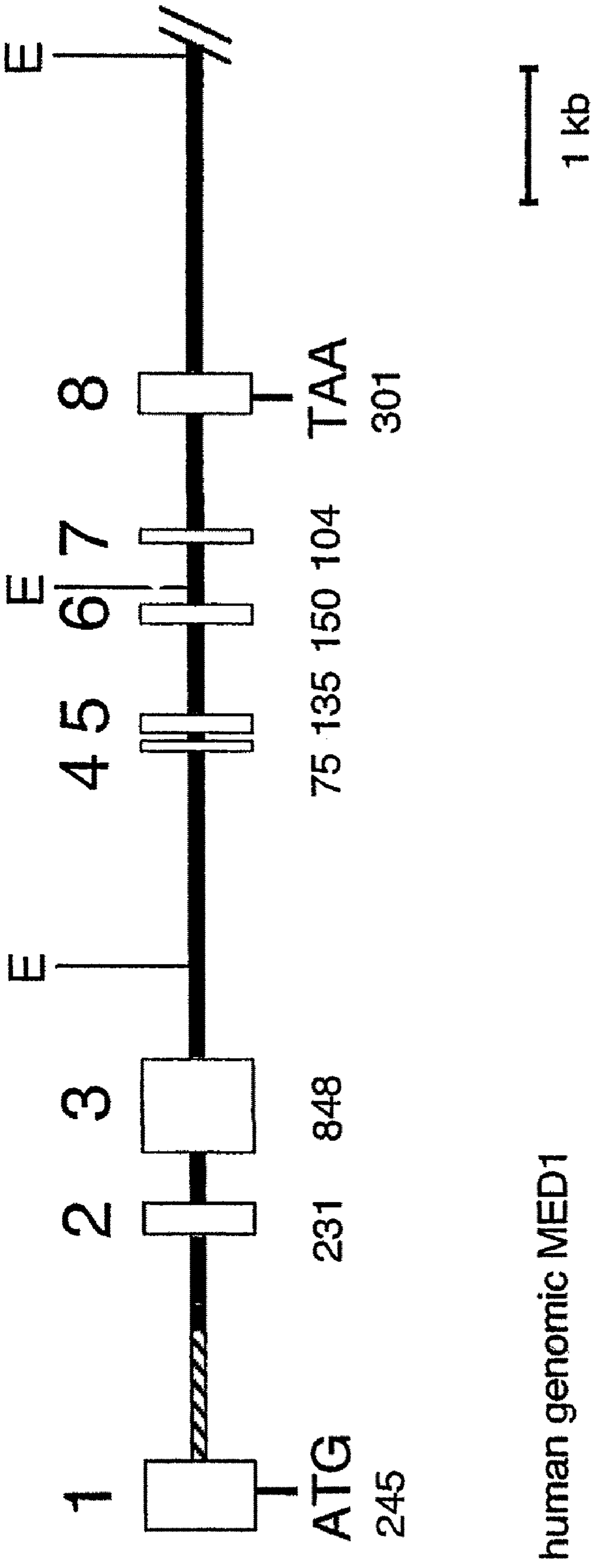
FIG. 13 is a schematic diagram of the genomic structure of the human MED1 gene (lambda clone MED1 HGL #16). The position of the eight exons is indicated. Numbers above the exon boxes refer to exon number; numbers below the exon boxes refer to the size of the exons in base pairs. Exon 1 and part of the intervening intron between exon 1 and exon 2 was cloned by PCR (indicated by the hatched line). The start (ATG) and stop (TAA) codons are marked. E: restriction site for the enzyme EcoRI.

Screening of a human genomic DNA library prepared in the lambda phage FIX II (Stratagene) with the f5/MED1 cDNA probe yielded six clones. One of these clones (# 16) was further characterized and subcloned in plasmid vectors. Sequence analysis of the subclones and comparison to the MED1 cDNA sequence allowed mapping of seven MED1 exons (exons 2 through 8, FIG. 13). The remaining exon (exon 1) and the intervening intron between exon 1 and exon 2 was cloned by PCR utilizing human genomic DNA as template and the primers of Sequence I.D. No. 6 and 20. SEQ ID NO: 20 is CAAATCTTCCTGCTGTCTTCC which maps within exon 2. Table I provides suitable primer sets for amplifying exons of the MED1 gene.

This human genomic clone has been deposited with the American Type Culture Collection, 10801 University Blvd., Manassas, Va. 20110-2209 on Jul. 28, 1998 under the terms of the Budapest Treaty, Accession Number: 203074. The sequence of the human genomic clone is shown in FIG. 19, SEQ ID NO:22.

TABLE I

OLIGONUCLEOTIDE PRIMERS FOR MED1

| | 5' primer | 3' primer |
|---|---|---|
| exon 1 | GTCTGGGGCGCTTTCGCAA (SEQ ID NO: 6) | CCACACACTGTCCACTCTCCCG (SEQ ID NO: 7) |
| exon 2 | ACTCCCATAGCACAAGACTGG (SEQ ID NO: 8) | GCTATGCTCCCACTACCTGC (SEQ ID NO: 9) |
| exon 3 | CCCTTCTATTTACTAGCAGTA (SEQ ID NO: 10) | GATGCAGCATATAAATTTCTC (SEQ ID NO: 11) |
| exons 4 and 5 | TGCATCCCTCAATATTGCTTT (SEQ ID NO: 12) | TCAATTCAGTGCTTTCTCCCT (SEQ ID NO: 13) |
| exon 6 | AGCCCACCTGGAGTCTTGTAA (SEQ ID NO: 14) | AAAGTTTAAGGTGTGGCTCTC (SEQ ID NO: 15) |
| exon 7 | GAAGCTGACCTGATAATGTGG (SEQ ID NO: 16) | CTTATTTTGCCTCAGAGACCA (SEQ ID NO: 17) |
| exon 8 | TATCGTAATGTACTGTCCCCC (SEQ ID NO: 18) | GCTTTAGCAAGGCTGATAGAA (SEQ ID NO: 19) |

Figure 15:
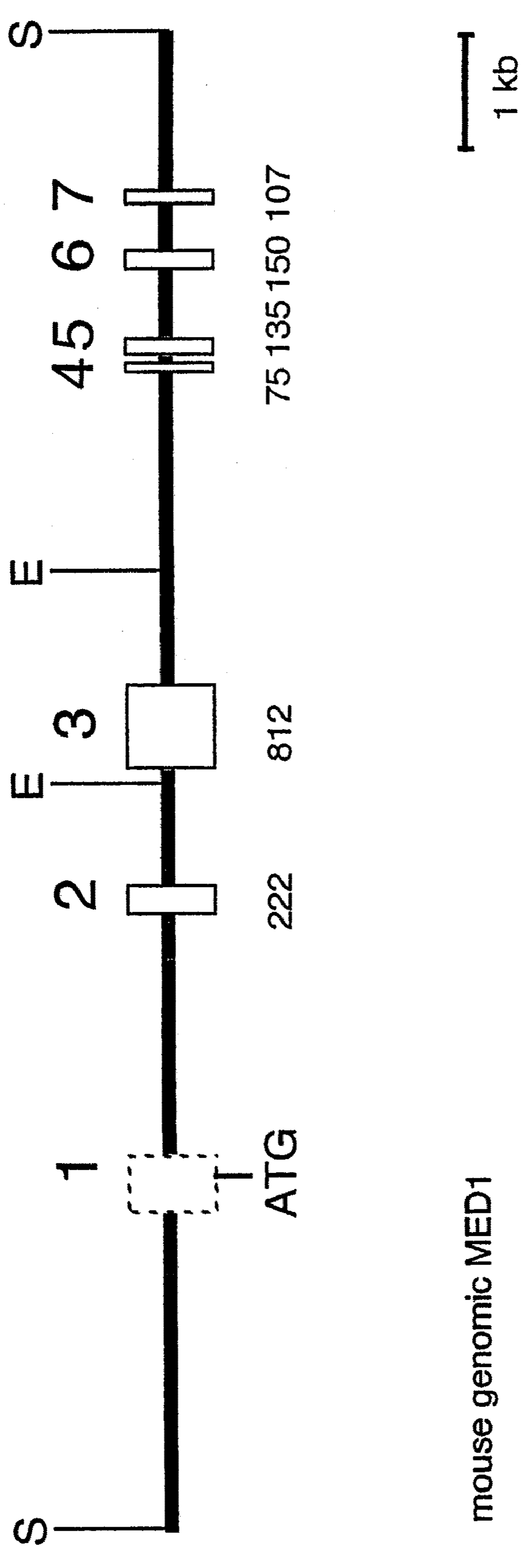
FIG. 15 shows a schematic of the genomic structure of the mouse MED1 gene (lambda clone MED1 MGL #3). The position of seven exons is indicated. Numbers above the exon boxes refer to exon number; numbers below the exon boxes refer to the size of the exons in base pairs. The size and position of the exon 1 are not well defined (as indicated by the dotted line). The start (ATG) codon is marked. The stop codon is presumably located in exon 8 which is not contained in this lambda clone. E: restriction site for the enzyme EcoRI; S: restriction site for the enzyme SalI.

Screening at low stringency of a mouse 129/SVJ strain genomic DNA library prepared in the lambda phage FIX II (Stratagene) with the same HindIII-HindIII fragment derived from the human MED1 cDNA probe (from nucleotide 1513-1935 of SEQ ID NO: 1) yielded one clone. This clone (#3) was further characterized and subcloned in plasmid vectors. Sequence analysis of the subclones and comparison to the human MED1 cDNA and genomic sequence allowed mapping of seven mouse MED1 exons (exons 1 through 7. FIG. 15). Assembling of the mouse MED1 exons allowed the derivation of a partial sequence of the mouse MED1 cDNA (FIGS. 16A and 16B). From the latter sequence a partial predicted amino acid sequence of the mouse MED1 protein was derived and it was shown to be highly conserved by comparison to the human MED1 protein sequence (FIG. 17). This mouse genomic clone has been deposited with the American Type Culture Collection, University Blvd., Manassas, Va. 20110-2209 on Jul. 28, 1998 under the terms of the Budapest Treaty, Accession Number: 203073. The sequence of the mouse genomic clone is shown in FIG. 18, SEQ ID NO:21.

B. Northern and Southern Blot Analysis.

A multiple tissue northern blot of poly-A selected RNA (Clontech) was hybridized under high-stringency conditions to a $^{32}$P-labeled 0.8 kb f5 probe. The blot was washed to a final stringency of 0.1×SSC/0.1% SDS (1×SSC is 0.15 M NaCl/0.015 M sodium citrate) at 65° C. for 40 minutes, and then exposed to X-ray film (Kodak X-Omat AR) at −70° C.

For the "Zoo" blot experiment, genomic DNA prepared from vertebrate species was digested with the restriction enzyme HindIII (New England Biolabs), separated on a 0.8% agarose gel and transferred to a nylon membrane. The membrane was hybridized to a $^{32}$P_labelled human MED1 cDNA probe (HindIII-HindIII fragment from nucleotide 1513 to nucleotide 1935 of the Sequence I.D. No. 1). Hybridization was performed in a solution containing 35% formamide, 6×SSC, 5×Denhardt's solution, 20 mM sodium phosphate pH 6.5, 20 micrograms/ml of sheared *E. coli* genomic DNA and 0.5% sodium dodecyl sulfate (SDS). The filter was washed twice at room temperature and twice at 65° C. in a solution containing 4×SSC and 0.1% SDS. Hybridization signals were revealed by autoradiography.

Figure 14A:
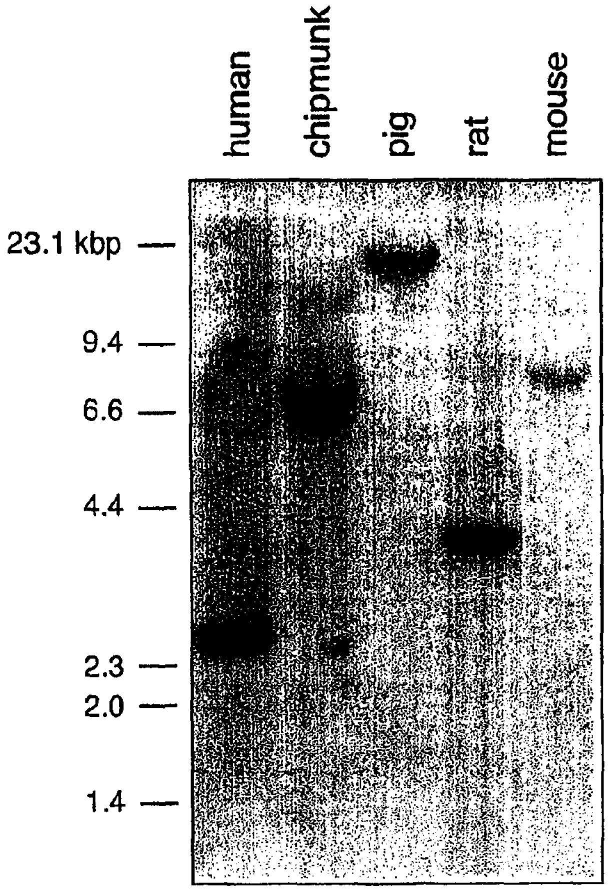
FIG. 14 is a blot showing the conservation of the MED1 gene ("Zooblot"). A low stringency Southern blot of genomic DNA from indicated vertebrate species reveals bands cross-hybridizing with a human MED1 cDNA probe in mammals (panel A) and non-mammalian vertebrates (panel B). The migration and size (in kilobase pairs) of the DNA standards are indicated.
Figure 14B:
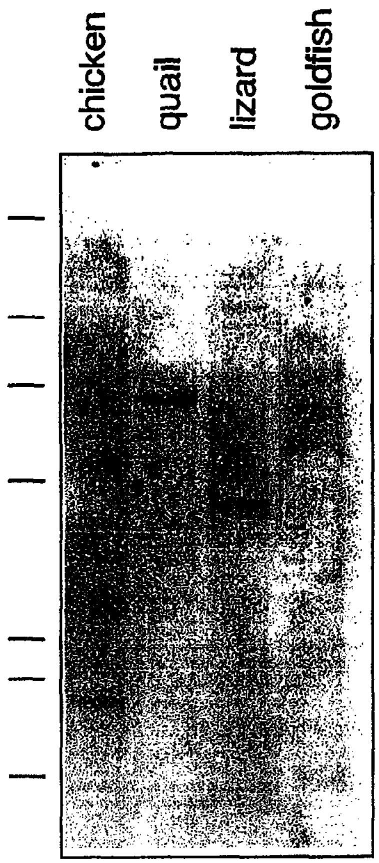

Hybridization of the HindIII-HindIII fragment probe (from nucleotide 1513 to nucleotide 1935 of the Sequence I.D. No. 1) at low stringency to a "zoo" blot revealed conservation of the MED1 gene among vertebrates. See FIG. 14.

C. In Vitro Transcription and Translation.

Coupled in vitro transcription and translation was conducted with a rabbit reticulocyte lysate- and T7 RNA polymerase-based kit (Promega), following the manufacturer's recommendations and employing $^{35}$S-methionine (Amersham).

D. Cell Culture, Expression Constructs, and Transfections.

NIH 3T3 cells were cultured in Dulbecco's modified Eagle's medium supplemented with 10% calf serum, penicillin (50 units/ml), streptomycin (50 g/ml), and kanamycin (100 μg/ml). The expression constructs of MED1 were generated in the CMV promoter-based CMV5 vector, a derivative of CMV4 (Andersson et al., (1989) *J. Biol. Chem.* 264:8222-8229). For construction of the hemagglutinin epitope carboxy-terminally tagged MED1 plasmid, the MED1 cDNA was inserted in place of the Gfi-1 ZN mutant construct open reading frame (Grimes et al. (1996) *Mol. Cell. Bio.* 16:6263-6272), a gift of Dr. Leighton Grimes. For construction of the hemagglutinin epitope amino terminally-tagged MED1 plasmids M1 and M2, a XbaI site was inserted by polymerase chain reaction immediately upstream of the ATG codons at nucleotide positions 142 and 262, respectively. Then the MED1 open reading frame, excised with XbaI and NsiI (blunted), was inserted in place of the Akt gene in the CMV5 hemagglutinin tag-Akt construct (Datta et al., (1996) *J. Biol. Chem.* 271:30835-30839).

Transient transfections of NIH 3T3 cells seeded in 6-well plates at 0.15×10$^6$ cells/well were carried out using 1.5 μg of DNA and 6 μl of lipofectamine (Life Technologies, Inc.), following the manufacturer's protocol. Forty-eight hours after transfection, cells were washed twice with Dulbecco's phosphate buffered saline and then lysed with RIPA buffer (10 mM sodium phosphate pH 7.0, 150 mM NaCl, 1% w/v sodium deoxycholate, 1% v/v Nonidet P-40, 0.1% w/v sodium dodecylsulfate, 1 mM phenylmethylsulfonyl-fluoride, 2 μg/ml aprotinin, 2 μg/ml leupeptin, 50 mM NaF, 1 mM sodium pyrophosphate, 1 mM sodium orthovanadate, 1 mM dithiothreitol, and 2 mM EDTA).

E. Western Blotting.

Cell lysates were separated by sodium dodecylsulfate-polyacrylamide gel electrophoresis (SDS-PAGE) in 8.5% gels and transferred to Immobilon P membranes (Millipore) by electroblotting with a Genie apparatus (Idea Scientific Co.) in a buffer containing 25 mM Tris-HCl pH 8, 190 mM glycine and 20% v/v methanol. Following overnight incubation in 5% dry milk in Tris-buffered saline (TBS: 0.9% w/v NaCl, 10 mM Tris-HCl pH 7.4, 0.05% w/v $MgCl_2$), the membrane was incubated for 1 hour at room temperature with the anti-hemagglutinin tag monoclonal antibody 12CA5 (Boehringer) in 2% dry milk in TBS. After three 10-minute washes in TBS supplemented with 0.1% v/v Tween-20, the membrane was incubated for 40 minutes at room temperature with an anti-mouse secondary antibody conjugated to horseradish peroxidase (Amersham). Following washing, the bound secondary antibody was detected by enhanced chemiluminescence (Amersham).

F. Fluorescence In Situ Hybridization.

Metaphase spreads from normal human lymphocytes were prepared according to published methods (Fan et al. (1990) *Proc. Natl. Acad. Sci.* 87:6223-6227). Nick translation was used to label a MED1 genomic DNA subclone with biotin-16-dUTP. Three hundred ng of the probe were then mixed with 150 μg of human Cot-1 DNA (Life Technologies Inc.) and 50 μg salmon sperm DNA to block repetitive elements. The DNA was denatured at 75° C. for 5 minutes and then reannealed for 1 hour at 37° C. prior to hybridization to metaphase spreads overnight at 37° C. The MED1 signal was detected with fluorescein isothiocyanate-labeled avidin (Oncor), whereas the chromosomes were counterstained with propidium iodide (Oncor). Metaphase spreads were observed using a Zeiss Axiophot microscope and images were captured by a cooled CCD camera (Photometrics) connected to a computer workstation. To identify the precise chromosomal location of the probe, the separate digitized images of FITC and propidium iodide were merged using Oncor version 1.6 software.

G. Electromobility Shift Analysis

Transient transfections of 293 cells seeded in 10-cm dishes were carried out using 12 μg of DNA and 48 μl lipofectamine (Life Technologies, Inc.), following the manufacturer's protocol. Seventy-two hours after transfections, cells were washed twice with Dulbecco's phosphate buffered saline and then lysed with NP-40 lysis buffer (0.5% Nonidet P-40, 10% glycerol, 137 mM NaCl, 20 mM Tris-HCl, pH 7.4) containing 1 mM phenylmethylsulfonylfluoride, 2 μg/ml aprotinin, 2 μg/ml leupeptin, 1 mM NaF, 1 mM sodium pyrophosphate, 1 mM sodium orthovanadate, and 1 mM dithiothreitol. Nuclei were disrupted by sonication with a sonic dismembrator (Fisher). Flag-MED1 was immunoprecipitated from the cell lysates with an anti-Flag antibody coupled to agarose beads (Kodak) and then eluted in a 50 μl volume with a solution containing a molar excess of Flag-peptide (Kodak) in electromobility shift analysis (EMSA) buffer (10 mM Tris-HCl, pH 7.5, 50 mM NaCl, 0.5 mM EDTA, 5% glycerol). A double stranded oligonucleotide containing five fully methylated CpG sites was generated by annealing the following oligonucleotides (M=5-methylcytosine):

```
Sequence I. D. No. 3:
5'-GCGAATTCMGTGCGAMGAAGCMGGACGATMGACCAGMGCTCGAGCA-3'

Sequence I. D. No. 4:
5'-GTGCTCGAGMGCTGGTMGATCGTCMGGCTTMGTCGCAMGGAATTCG-3'
```

The double-stranded oligonucleotide was labeled with $^{32}P$-α-dCTP and Klenow enzyme. EMSA was conducted as described previously (Durand et al., (1988) *Mol. Cell. Biol.* 8:1715-1724). Briefly, binding of MED1 to labeled oligonucleotides was carried out by incubating 1 μl out of 50 μl of the MED1 eluate, $7\times10^4$ cpm of labeled oligonucleotides and 4 μg of poly (dI-dC) in EMSA buffer (final volume of 20 μl) at room temperature. Competition was carried out in the presence of 100 ng (100-fold excess) of the cold oligonucleotide. Binding reactions were separated on a 6% non-denaturing polyacrylamide gel and visualized by autoradiography of the dried gel.

For the electromobility shift assay employing the purified methyl-CpG binding domain (MBD) of MED1, the methylated probe was assembled by annealing the two complementary oligonucleotides of Sequence I.D. No. 3 and Sequence I.D. No. 4. containing 5-methylcytosine. See FIG. 10B. The unmethylated probe was assembled with two complementary oligonucleotides of identical sequence to the oligonucleotides of Sequence I.D. No. 3 and Sequence I.D. No 4, except that cytosine replaced 5-methylcytosine. Labeling of the probes was conducted as above. DNA binding reactions were carried out in 10 mM Tris-HCl pH 7.5, 50 mM NaCl, 5% glycerol, 0.5 mM EDTA, 0.5 mM DTT, in the presence of 0.5 μg of polydA/polydT (ICN) as non-specific competitor DNA [S. Buratowski and L.A. Chodosh, In *Current Protocols in Molecular Biology*, eds. F. M. Ausubel, et al., John Wiley & Sons, New York (1996)]. Bacterially expressed and purified MBD (20 ng) was incubated with the $^{32}P$-labeled double-strand oligonucleotides (20,000 cpm, 0.2 ng) on ice for 30 min. For competition, the MBD was pre-incubated on ice for 20 min with a 100-fold excess of the cold oligonucleotide (20 ng) prior to addition of the probe. Binding reactions were loaded on a 10% acrylamide gel and run at 4° C. in 0.5×TBE. Dried gels were exposed to autoradiography.

H. Co-Immunoprecipitation Analysis

To analyze the interaction of MED1 with hMSH2, following transient transfection of 293 cells with the constructs of the invention (Flag-tagged MED1), and lysis of cells after a 72 hour period, proteins were immunoprecipitated with anti-Flag antibody as described above. Immunoprecipitates were resuspended in Laemmli buffer, boiled for 10 minutes, separated on 8.5% SDS-PAGE and transferred to Immobilon P membranes. Western blotting was carried out as described above, using an antibody against hMSH2.

For analysis of the interaction of MED1 with hMLH1, HEK-293 cells were cultured at 37° C. and 7.5% $CO_2$ in Dulbecco's modified Eagle's minimum essential medium (DMEM) supplemented with 10% fetal calf serum, penicillin (50 units/ml), streptomycin (50 μg/ml), and kanamycin (100 μg/ml). Cells seeded in 100-mm Petri dishes were transfected with the construct of the invention, hemagglutinin-tagged MED1, using LipofectAMINE (Life Technologies, Inc.) according to the manufacturer's protocol. Seventy-two hours later, cells were lysed on ice in one of three lysis buffers, containing 0.5% Nonidet P-40 (NP-40)[K. Datta et al., *Mol. Cell. Biol.* 15: 2304-2310 (1995)], 0.2% NP-40 [W. Gu, K. Bhatia, I. T. Magrath, C. V. Dang, R. Dalla-Favera, *Science* 264: 251-254 (1994)], or 1% Triton X-100 [S. F. Law et al., *Mol. Cell. Biol.* 16: 3327-3337 (1996)]; NP-40 lysates were mildly sonicated using a sonic dismembrator (Fisher). Immunoprecipitations were carried out with the anti-hemagglutinin tag antibody HA.11 coupled to beads (Berkeley Antibody Company). Immune complexes were washed with lysis buffer, and the proteins were resolved by 8.5% SDS-polyacrylamide gel electrophoresis (SDS-PAGE) and transferred to PVDF membranes (Immobilon P, Millipore) with an X-genie electroblotter (Idea Scientific). Membranes were probed with an anti-MLH1 antibody (Pharmingen) and as a control for expression of the construct, with the HA.11 antibody (Berkeley Antibody Company). Detection of antigen-bound antibody was carried out using enhanced chemiluminescence (ECL, Amersham), according to the manufacturer's protocol. See FIG. 11C.

I. Expression of the MED1 Catalytic Domain in *E. coli*

The nucleic acid sequence encoding the catalytic domain of MED1 was cloned in the vector pET28b (Novagen) as a carboxyterminal fusion to a 6×His tag for expression in *E. coli*. This construct was transferred to the *E. coli* strain BL21 (DE3)pLysS. Overnight cultures were diluted 1:15 in fresh medium and incubated for one-hour in a 37° C. incubator. Expression of the construct was induced by addition of 1 mM IPTG for an additional 3 hours at 37° C. Cells were then collected by centrifugation and lysed in Laemmli buffer. Lysates were boiled for 10 minutes and separated on 12% SDS-PAGE. Proteins were visualized by Coomassie blue staining.

J. Activity Staining of the MED1-Catalytic Domain after Sodium Dodecyl Sulfate-Polyacrylamide Gel Electrophoresis Activity staining of MED1 was performed essentially as described by Blank et al. (Blank et al. (1982) Analytical Biochemistry 120: 267-275). Briefly, bacterial lysates expressing the MED1 catalytic domain were separated in SDS-polyacrylamide gels (12%) containing 0.15 mg/ml heat-denatured calf thymus DNA. Following electrophoresis, the gel was incubated in a buffer containing 10 mM Tris-HCl pH 7.4 and 25% isopropanol for one hour at room temperature with one change of buffer every twenty minutes. After the first hour, the gel was immersed in a buffer containing 10 mM Tris-HCl pH 7.4 for an additional hour with buffer changes every twenty minutes. The gel was then immersed in a buffer containing 10 mM Tris-HCl, pH 7.4, 10 mM $MgCl_2$, 5 mM $CaCl_2$, 2 μM $ZnCl_2$ for 16 hours at room temperature to allow digestion of DNA. DNA was visualized by staining the gel with 0.2% toluidine blue 0 in 10 mM Tris-HCl pH 7.4, followed by destaining in 10 mM Tris-HCl pH 7.4 for one hour at room temperature with one change of buffer every 20 minutes. Deoxyribonuclease activity results in a zone of clearing indicating reduced DNA staining (Blank et al., (1982) supra).

K. Endonuclease Activity of Recombinant Wild-Type MED1.

The entire wild-type MED1 (codons 1-580, wt) and a deletion mutant lacking the endonuclease domain (codons 1-454, Δendo) were expressed in bacteria and purified by nickel-agarose chromatography. For bacterial expression, PCR-generated fragments corresponding to the entire MED1 open reading frame or to isolated domains were propagated in *E. coli* strain XL-1 Blue (Stratagene) and transferred into pET28 (b) (Novagen). Constructs were sequenced with an automated DNA sequencer (ABI) to verify that unwanted mutations were not inadvertently introduced; and they were transferred into *E. coli* strain BL21(DE3)pLysS. These cells were grown to O.D.600=0.4 and then induced with 1 mM IPTG at 37° C. for 3 hours. Bacterial lysates were purified over a nickel-agarose column ($Ni^{2}$+-NTA agarose, Qiagen). Increasing amounts of the wild-type and Δendo mutant (22, 44, 87.5 and 175 ng) were incubated with 500 ng of the 3.9 kb supercoiled plasmid pCR2 (Invitrogen) at 37° C. for 30 min in a buffer containing 20 mM Tris-HCl pH 7.5, 25 mM KCl and 10 mM $MgCl_2$. Reaction products were separated on a 1% agarose gel buffered in 1×TAE and containing 0.25 μg/ml ethidium bromide.

Identification and Characterization of MED1

To facilitate efforts to identify eukaryotic functional homologues of the *E. coli* MutH endonuclease, the yeast interaction trap assay, a cloning strategy which screens for protein-protein interactions in the yeast *S. cerevisiae* (Golemis et al., 1996, supra) was employed. This strategy was based on the rationale that the human mismatch repair endonuclease would interact with hMLH1, the human MutL homologue, in a comparable way to what is observed in bacteria where the endonuclease MutH interacts with MutL. The complete coding sequence of hMLH1 (amino acids 1-756) was fused to the carboxy terminus of the DNA binding domain of LexA. This construct ("bait") was introduced along with the appropriate reporter plasmid in the yeast strain EGY191. EGY191, which harbors only two LexA operators directing transcription of the chromosomal LEU2 gene, was used because in initial experiments, employing the standard EGY48 strain, the bait protein had constitutive transcriptional activity (data not shown). Western blot analysis with an anti-LexA antibody showed that pEG202-t-hMLH1 directs the synthesis of the expected size product for a LexA-hMLH1 bait protein in EGY191. In control experiments, performed following standard procedures, this protein was transported to the nucleus and did not activate transcription of the chromosomal LEU2 gene and of the episomal LacZ gene (data not shown). The EGY191/pSH18-34/pEG202-t-hMLH1 yeast cells were supertransformed with a human fetal brain cDNA library (approximately $4\times10^5$ recombinants) fused to the B42 portable activation domain, and colonies growing on selective leucine-minus plates in the presence of galactose but not glucose as carbon source were isolated. Twenty-two clones (f1 to f22) were selected encoding putative hMLH1 interactors. One clone, designated f5, (later named MED1) was identified which strongly interacted with hMLH1, based on the early appearance of colonies on selective leucine-minus/galactose plates and on the intensity of color formation of colonies grown on indicator X-Gal/galactose plates. The specificity of the f5-hMLH1 interaction was assayed by supertransforming virgin EGY191/pSH18-34/pEG202-t-hMLH1 cells with f5 plasmid DNA. As a control, EGY191/pSH18-34 cells transformed with bait constructs of pEG202-bicoid, -MYC, -K-rev, and empty pEG202 vector, were also supertransformed with f5 DNA. Cells transformed with the combination of f5 and pEG202-t-hMLH1 grew on leucine-minus/galactose but not leucine-minus/glucose medium and turned blue on X-Gal/galactose but not X-Gal/glucose plates. Control cells failed to grow on leucine-minus/galactose and to turn blue on X-Gal/galactose plates, confirming specificity of the interaction between f5 and hMLH1 as shown in FIG. 1.

Figure 2:
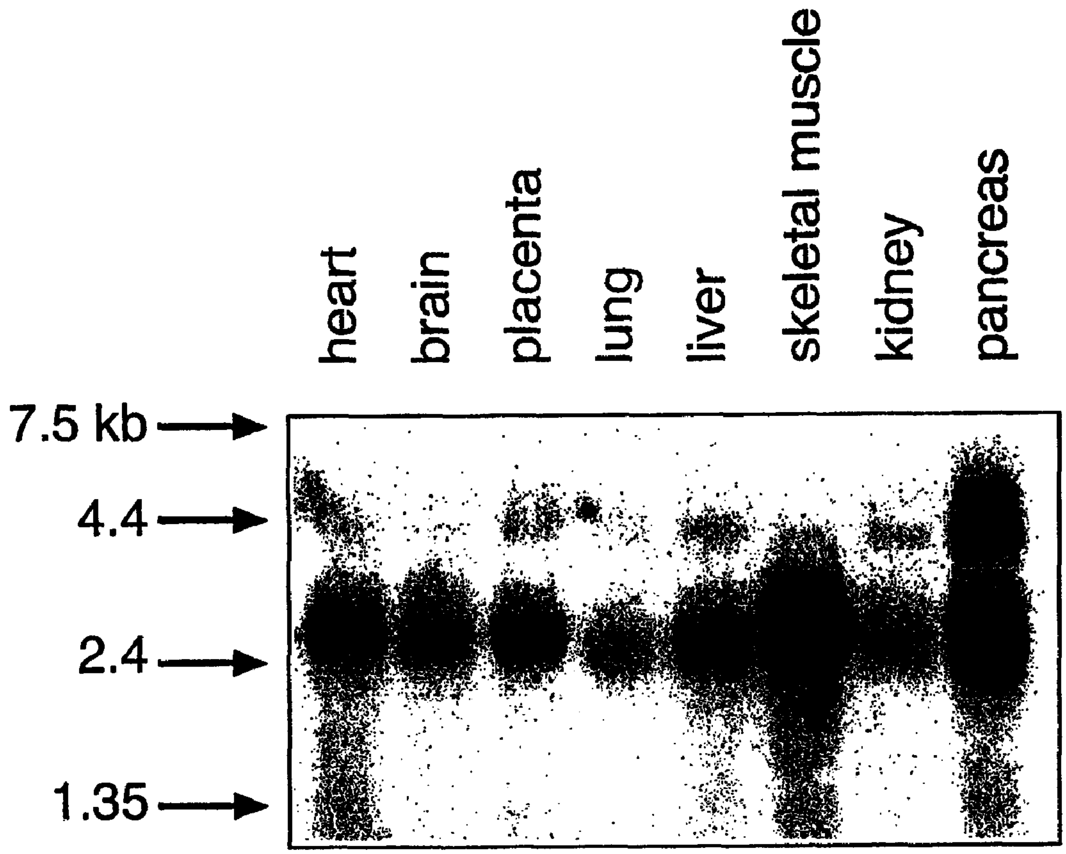
FIG. 2 depicts a Northern blot showing the localization of MED1 mRNA in all tested tissues. A 2.4 kb transcript is observed and high levels of mRNA expression is detected in heart, skeletal muscle and pancreas. The size of the molecular weight standards is indicated in kb.

Initial sequence analysis revealed that f5, which was represented only once in this group of 22 putative interactors, codes for a protein sharing homology with several bacterial endonucleases involved in DNA repair. Since the f5-encoded protein is a putative DNA repair enzyme, its expression is expected to be ubiquitous. A Northern blot containing mRNA from multiple tissues was probed with the entire 0.8 kb insert of the f5 clone. This analysis revealed that, consistent with a putative housekeeping role in DNA repair, the f5 gene is expressed in all normal tissues tested with a transcript of approximately 2.4 kb. See FIG. 2.

In order to clone the remaining portion of the gene, a f5-derived probe was used to screen four additional cDNA libraries, three from fetal brain and one from the ovarian cancer cell line C200. Six clones were isolated from the fetal brain libraries and 11 from the C200 library. These clones were sequenced. Overlapping sequences were aligned until the nearly complete sequence of the gene was determined (2.1 kb). See FIG. 3. The MED1 transcript contains an open reading frame of 1740 bases, preceded by an in-frame stop codon, which predicts a protein of about 580 amino acids encoded by the sequence of Sequence I.D. No. 2. Slight sequence variations were observed between the cDNA clones analyzed. These are set forth below:

Sequence Variations

1) Nucleotides 1325-1342: 18 nucleotides—GTGAGAAAATATTTCAAG—are either present (as in Sequence I.D. No. 1) or absent (as in Sequence I. D. No. 23) from the cDNA, therefore the 6 amino acids encoded by those nucleotides (GEKIFQ) are either present (as in Sequence I. D. No. 2) or absent (as in Sequence I. D. No. 24) in the predicted protein. This variation appears to originate from alternative usage of a splice donor site. In the genomic DNA sequence:

. . . GACTTCACTGGTGAGAAAATATTTCAAGGT . . .

If the second splice donor site (bold) is used, then the 18 nucleotides GTGAGAAAATATTTCAAG are incorporated in the mRNA; if the first splice donor site (underlined) is used, then the same 18 nucleotides are spliced out and are not incorporated in the mRNA.

2) Nucleotide 1876: T (as in Sequence I.D. No. 1) or C (as in Sequence I. D. No. 25), therefore codon 579 is either TTA or CTA (no amino acid variation, since both code for leucine).

3) Nucleotide 2042: C (as in Sequence I.D. No. 1) or T (as in Sequence I. No. 26), (no amino acid variation, since this change is in the 3' untranslated region).

4) Poly-A tail: Added after nucleotide 2106 (as in Sequence I.D. No. 1) or approximately 150-200 bases downstream (precise site not determined): this variation probably originates from an alternative polyadenylation signal.

5) Nucleotide 1214=T (as in Sequence I.D. No. 1) or C (as in Sequence I. D. No. 27), therefore codon 358 is either ATC or ACC, coding for isoleucine or threonine, respectively. This sequence variation is described in more detail in relation to Example II.

Figure 4B:
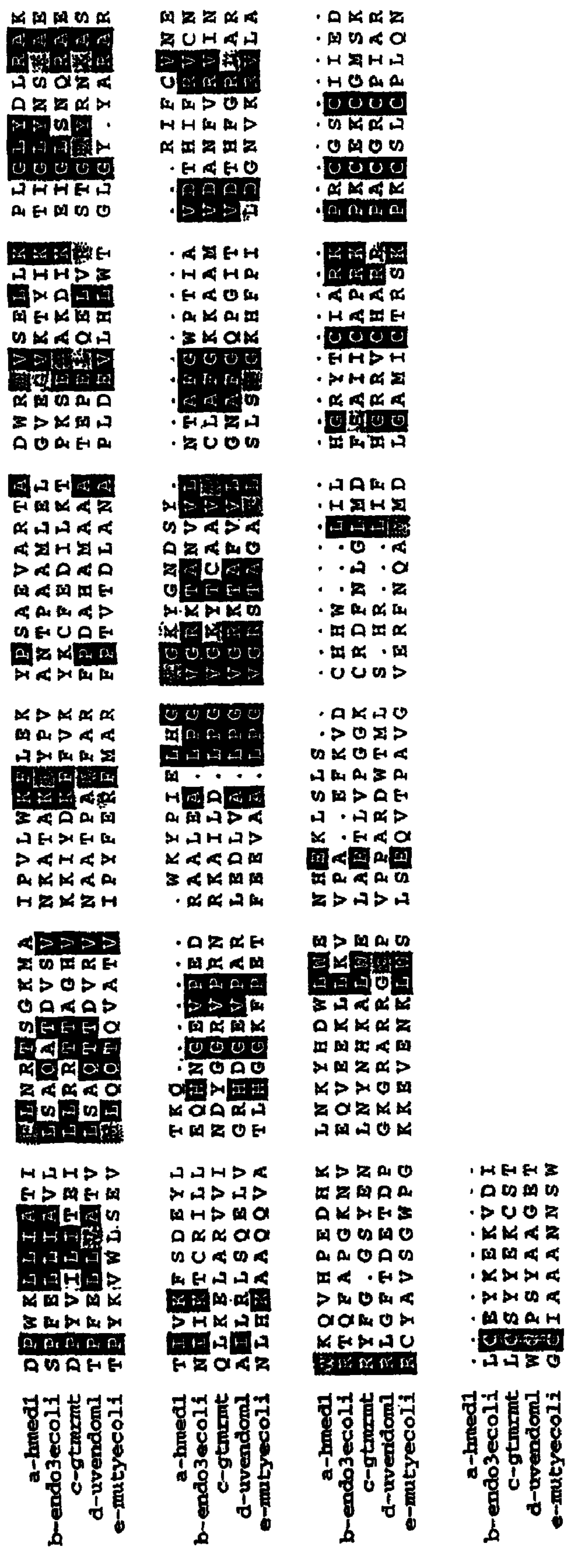
FIG. 4B depicts homology analysis of the deduced amino acid sequence of MED1 and the methyl-CpG binding domain of the rat protein, MeCP2.
Figure 5:
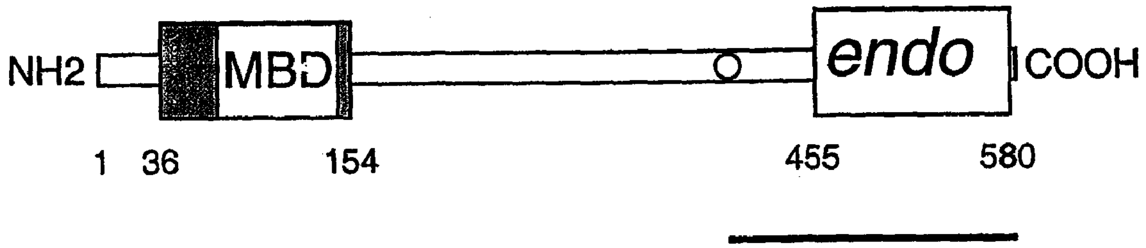
FIG. 5 is a schematic diagram illustrating the domain organization of MED1 protein. The methyl-CpG binding domain (MBD) and the endonuclease domain (endo) are highlighted. Numbers indicate amino acid position. The bar below the schematic diagram indicates the portion of the protein encoded by the original f5 clone.

Analysis of the predicted MED1 protein sequence reveals a tripartite structure. At the amino terminus, MED1 contains a region of homology to the methyl-CpG binding domain (MBD) of MeCP2, a chromosomal protein which binds CpG-methylated DNA and may mediate the effects of DNA methylation on chromatin structure and transcription (Lewis et al., (1990) *Cell* 69:905-914; Nan et al., (1993) *Nucleic Acids Res.* 21:4886-4892). The same region of MED1 is also homologous to the MBD of the human protein PCM1, a component of the transcriptional repressor MeCP1 (Cross et al., (1997) Nat. Genet. 16:256-259). The central portion of MED1 does not display a recognizable domain structure, but it appears to be rich in positively-charged amino acids, often arranged in short clusters which might represent nuclear localization signals (Boulikas, T., (1993) *Critical Rev. in Eukaryotic Gene Expression* 3:193-227). Finally, at the carboxy terminus, MED1 contains a putative catalytic domain sharing homology with several bacterial endonucleases of the glycosylase/lyase type involved in DNA repair, including MutY and endonuclease III from *E. coli*, ultraviolet endonuclease from *Micrococcus luteus*, and the putative endonuclease encoded by the ORF10 of the thermophilic archaeon *Methanobacterium thermoformicicum*. See FIGS. 4A, 4B and 4C. A schematic of the domain organization of MED1 is shown in FIG. 5.

Figure 6:
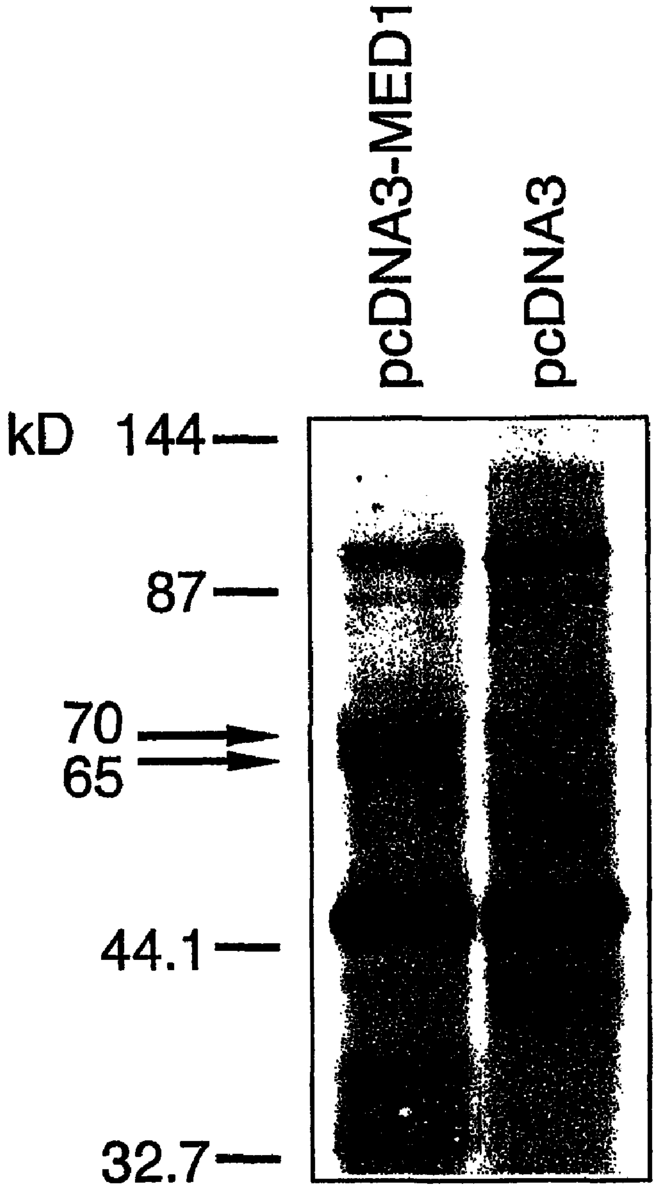
FIG. 6 is an autoradiograph showing the results of coupled in vitro transcription and translation of the MED1 open reading frame. Two polypeptides of 70 and 65 kD are synthesized by pcDNA3-MED1 constructs. In control reactions, lacking the MED1 cDNA, these polypeptides are not synthesized.
Figure 7A:
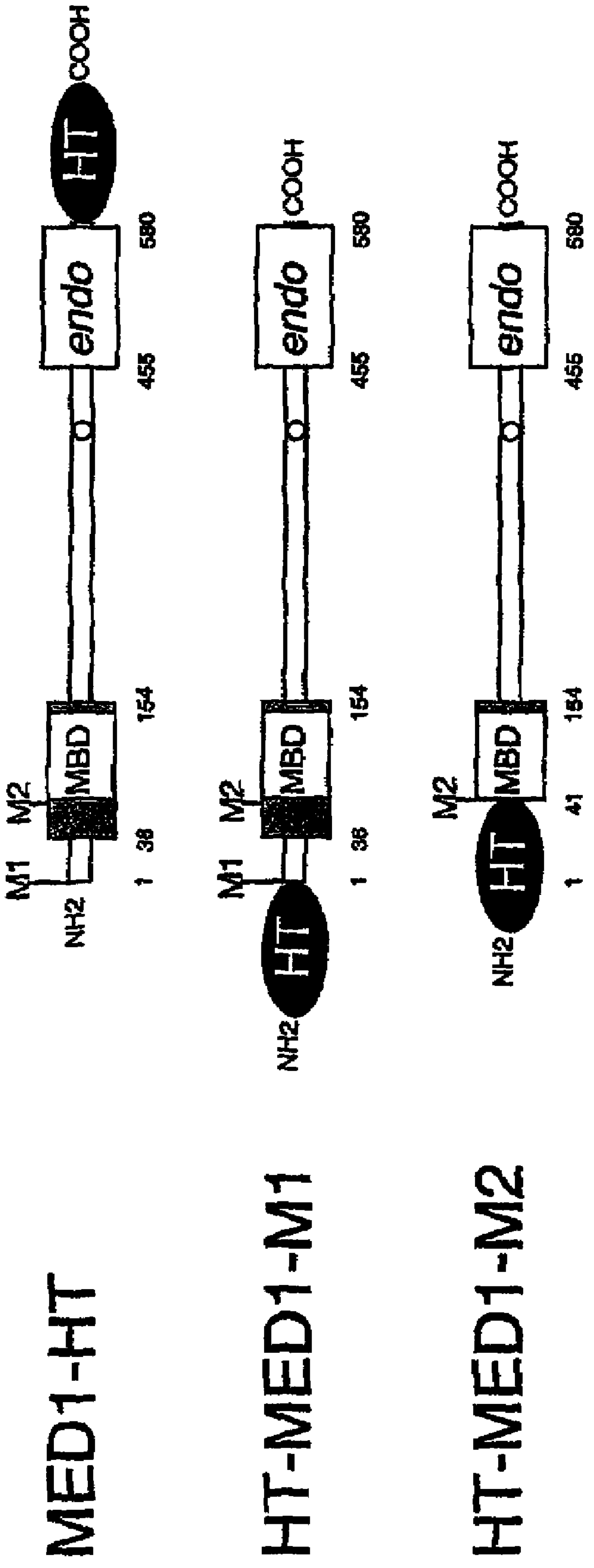
FIGS. 7A and 7B show a schematic diagram (FIG. 7A) of carboxy- and amino-terminal hemagglutinin-tagged (HT) MED1 proteins and a Western Blot (FIG. 7B) showing protein expression following transfection of the constructs into NIH 3T3 cells. A band of approximately 72 kD is present in cells transfected with the carboxyterminally tagged MED1-HT. This band co-migrates with the one present in HT-MED1-M1 transfectants, indicating that the first ATG at nucleotide position 142 is the initiation codon in vivo.
Figure 7B:
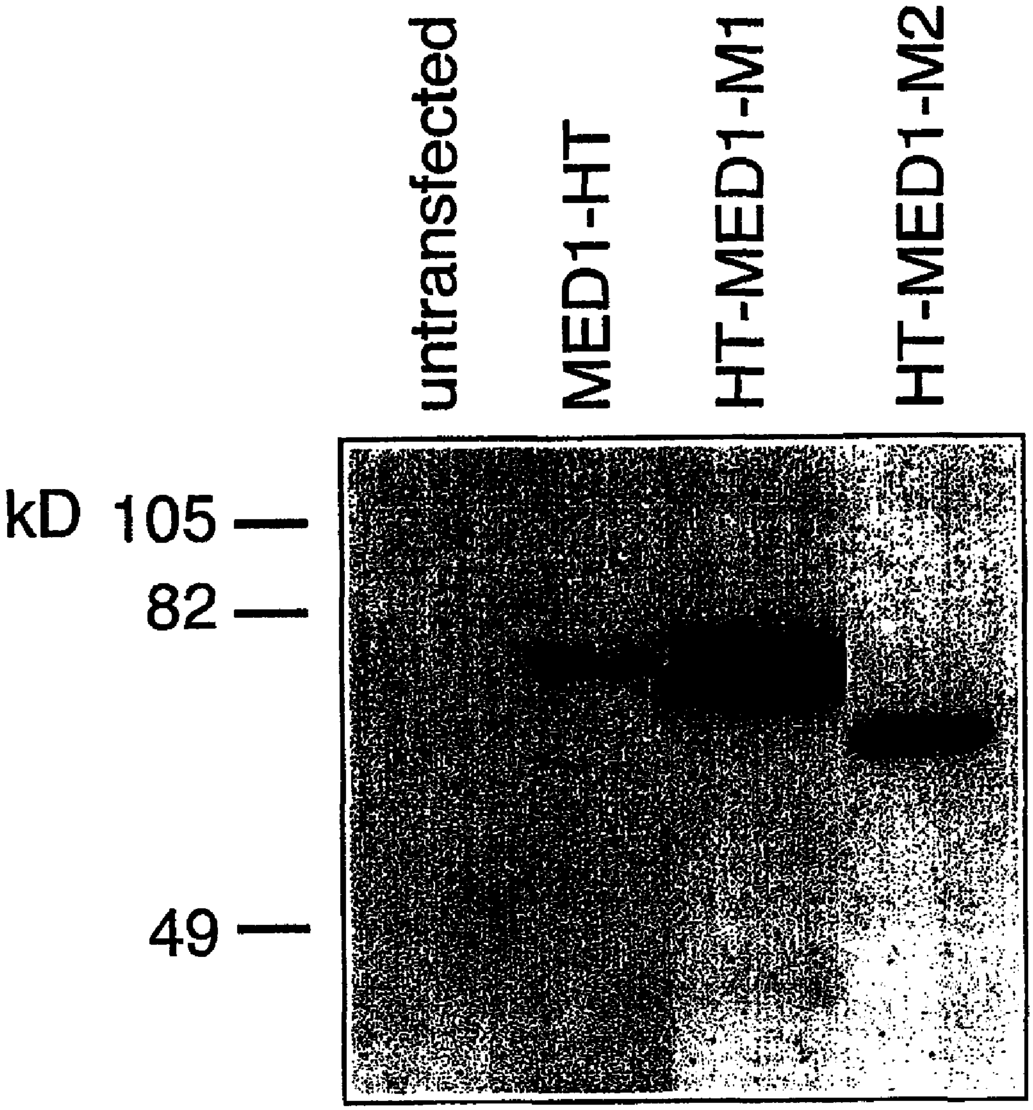

In order to confirm that the MED1 open reading frame is capable of directing the synthesis of a protein product, a construct of MED1 in the vector pcDNA3 was employed in an in vitro coupled transcription and translation assay. The result indicated that the MED1 open reading frame drives the translation of two polypeptides of 70 and 65 kD, shown in FIG. 6, in good agreement with the molecular weight predicted from the amino acid sequence. The synthesis of these two polypeptides might be the result of initiation from the two close ATG codons, at nucleotide position 142 and 262, respectively. Such a possibility is known to occur as a result of “leaky” ribosome scanning and is increased by a suboptimal Kozak’s context (Kozak, M., (1995) *Proc. Natl. Acad. Sci.* 92:2662-2666). The difference in molecular weight (5 kD) would be compatible with the distance between the two ATG codons (40 a.a.). To determine if two MED1 proteins are also synthesized in vivo, a hemagglutinin epitope was fused at the carboxyterminal end of the MED1 open reading frame, generating the construct MED1-HT. Constructs were also generated which fused a hemagglutinin tag immediately before each of the two putative initiation codons (HT-MED1-M1 and HT-MED1-M2). These constructs were transiently transfected in NIH-3T3 cells and lysates of the transfectants were prepared and separated by SDS-PAGE. Western analysis with an anti-hemagglutinin tag antibody revealed the presence of a band of approximately 72 kD in cells transfected with the carboxyterminally tagged MED1-HT. This band comigrates with the one present in HT-MED1-M1 transfectants, indicating that the first ATG at nucleotide position 142 is the initiation codon in vivo. See FIG. 7. Since the expression level of HT-MED1-M1 which uses the hemagglutinin tag ATG codon is much higher than MED1-HT which uses the autologous ATG codon, it is possible that the expression of the MED1 protein is under a tight translational control.

Figure 8:
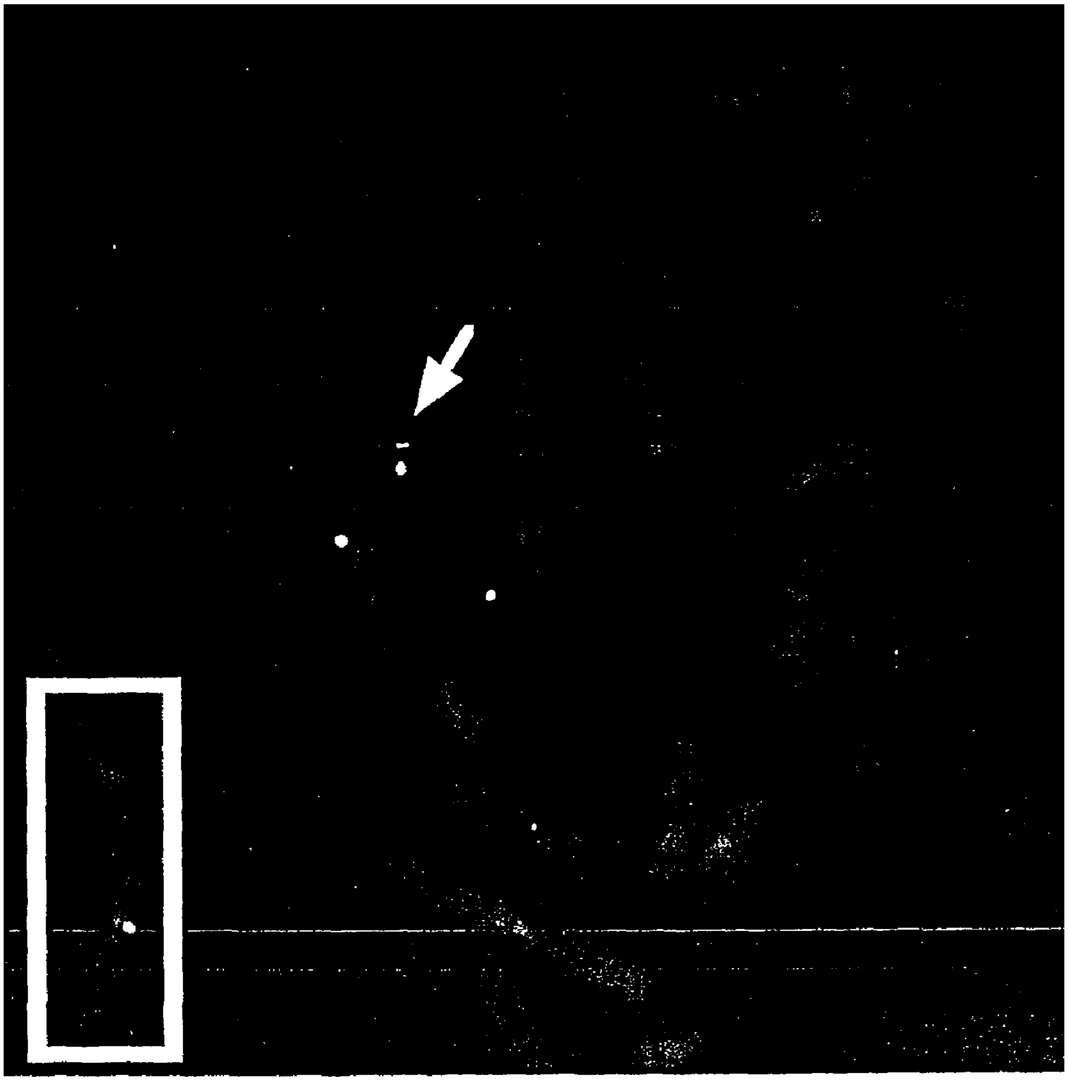
FIG. 8 is a partial metaphase spread of human chromosomes showing the chromosomal localization of MED1 by FISH. Hybridization is detected on chromosome 3q21 (arrow). An elongated chromosome 3 is shown in the inset.

Finally, the MED1 gene was mapped with fluorescence in situ hybridization to human chromosome 3q21-22. See FIG. 8.

Figure 9A:
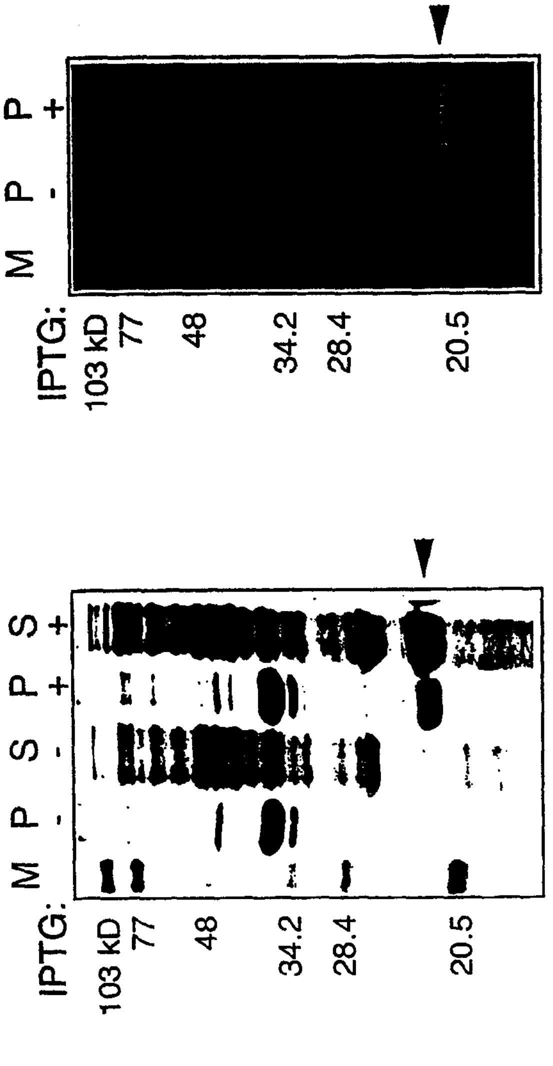
FIGS. 9A and 9B are gels and blots demonstrating the nuclease activity of the recombinant endonuclease domain.

In order to determine whether MED1 has endonuclease activity, the catalytic (endonuclease) domain was expressed in *E. coli* as a carboxyterminal fusion to a 6×His tag. High levels of expression of the domain as a polypeptide of approximately 18-22 kD were achieved. See FIG. 9A, left panel. Bacterial lysates expressing the catalytic domain were separated in an activity polyacrylamide gel containing denatured calf thymus DNA. Following electrophoresis, the gel was incubated in a Tris-buffered solution containing 25% isopropanol and then in Tris buffer alone to allow digestion of DNA. DNA was visualized by staining the gel with toluidine blue O. Results revealed a zone of clearing, indicative of DNA digestion, migrating at approximately 18-22 kD in *E. coli* lysates expressing the endonuclease domain but not in control lysates. See FIG. 9A, right panel. This experiment indicates that the recombinant catalytic domain of MED1 displays deoxyribonuclease activity.

Figure 9B:
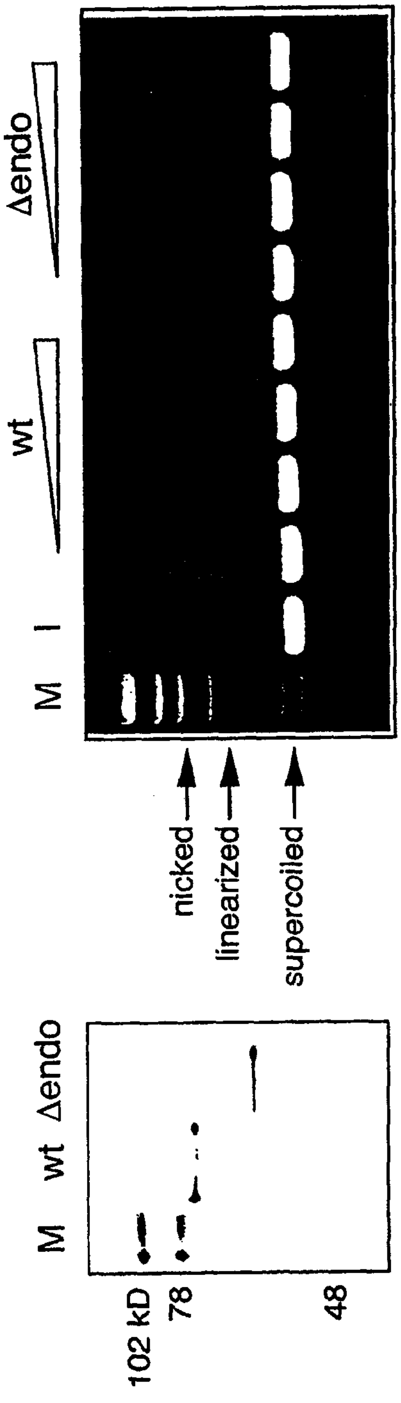

To better define its nuclease properties, the entire MED1 protein was expressed in *E. coli* as a carboxyterminal fusion to a six-histidine tag and purified on a nickel-agarose column to approximately 95% homogeneity. See FIG. 9B, left panel. Endonuclease activity was assayed by evaluating the conversion of a supercoiled plasmid into open circles (nicked) and linear molecules. Increasing amounts of the purified MED1 protein were incubated with supercoiled plasmid DNA at 37° C. for 30 min, and the products of the reactions, separated on a 1% agarose gel, were visualized by ethidium bromide staining. Incubation with MED1 resulted in a dose-dependent appearance of nicked and linearized molecules (FIG. 9B, right panel). In order to rule out the possibility that a bacterial endonuclease activity copurifying with MED1 is responsible for the observed effects, a deletion mutant lacking the putative endonuclease domain was also purified. This mutant failed to produce nicked and linearized DNA molecules (FIG. 9B, right panel). These results indicate that MED1 has single- and double-strand endonuclease activity on a supercoiled plasmid substrate. Additional studies of the catalytic activity of MED1 are presented in Example V.

Digestion of the MED1-linearized plasmid with the restriction enzyme EcoRI, which performs two closely spaced cuts on this plasmid, resulted in the appearance of a smear, indicating that MED1 does not have preferential cutting sites on this substrate. The production of linear molecules by MED1 in the above assay is intriguing. The kinetics suggest rapid counter-nicking of the second strand across from a site where the first nick is formed. It will be interesting to determine whether the MED1 nicks occur in CpG-rich regions and whether cytosine methylation modulates the second nicking event.

Figure 10A:
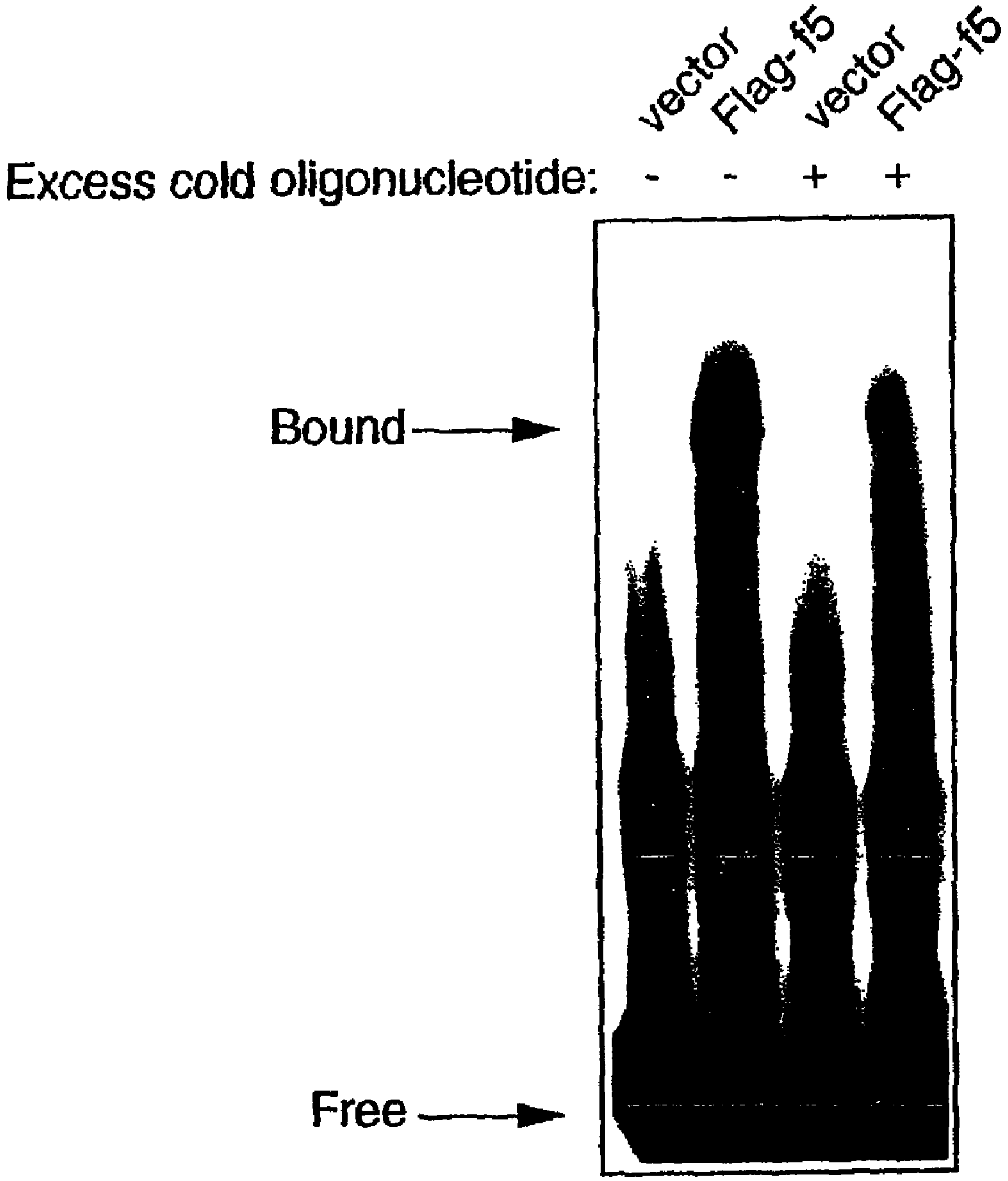
FIG. 10A is an autoradiograph showing the results of a mobility shift assay of 293 cell lysates expressing the fusion protein Flag-MED1/f5. Flag-peptide eluates from anti-Flag immunoprecipitations of Flag-MED1/f5-expressing 293 cells demonstrate binding activity when incubated with a $^{32}P$-labeled double-stranded oligonucleotide containing five fully methylated CpG sites. A mobility shift assay of recombinant MED1 MBD (codons 1-154) with methylated and unmethylated DNA probes is shown in FIG. 10B. The purified MED1 MBD demonstrates binding activity when incubated with a $^{32}P$-labeled double-stranded oligonucleotide containing five methylated CpG sites (lane 2). Binding is abolished by pre-incubation with a 100-fold excess of the cold methylated oligonucleotide (lane 3), but not of the cold unmethylated oligonucleotide (lane 4). No binding is detected when the unmethylated probe is used (lanes 5-8)

To assess whether the MED1 methyl-CpG binding domain (MBD) is able to bind methylated DNA, a FLAG epitope was fused at the amino terminal end of the MED1 open reading frame, generating the construct FT-MED1/f5, and this construct was transfected into the human kidney line 293. Cells were also transfected with the empty expression vector. Seventy-two hours after transfection, cells were lysed and the lysates were immunoprecipitated with an anti-Flag antibody coupled to agarose beads. Bound protein was eluted from the beads following incubation with a FLAG peptide. The FT-MED1/f5 and control eluates were incubated with a $^{32}P$-labeled double-stranded oligonucleotide containing a total of five fully methylated CpG sites, in the presence or absence of a 100-fold excess of the unlabeled or “cold” oligonucleotide. The binding reactions were separated on a non-denaturing polyacrylamide gel and detected by autoradiography of the dried gel. A slowly migrating band was detected in the FT-MED1/f5 eluate lanes, but not in the control lane. This band was abolished by competition with excess cold oligonucleotide. This experiment indicated that the MBD of MED1 functions as a specific methylated DNA binding domain in vivo. See FIG. 10A.

Figure 10B:
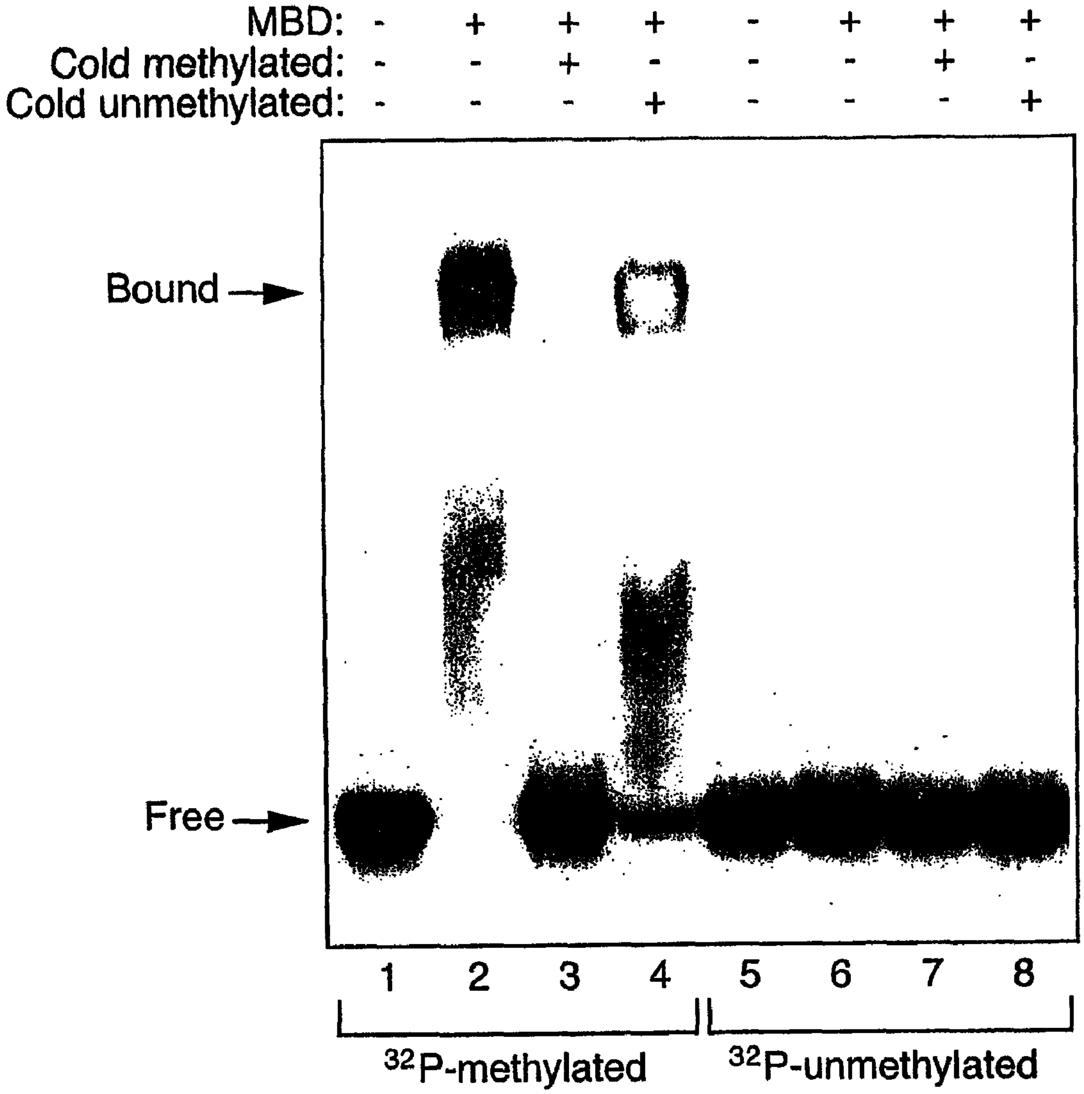

To further characterize the DNA binding properties of MED1, its putative methyl-CpG binding domain (MBD) was expressed in *E. coli* as a carboxyterminal fusion to a six-histidine tag, and it was purified by metal-chelating affinity chromatography followed by ion-exchange chromatography on SP Sepharose (Pharmacia). The purity of the MED1 MBD was estimated at >98% by SDS-PAGE followed by Coomassie staining. The purified MBD was incubated with a $^{32}$P-labeled double-strand oligonucleotide of arbitrary sequence containing five symmetrical methyl-CpG sites. As a control, MBD was incubated with a $^{32}$P-labeled double-strand oligonucleotide of identical sequence in which cytosines replaced 5-methyl-cytosines. EMSA analysis of the complexes indicated that the MED1 MBD binds to methylated DNA and fails to bind to unmethylated DNA (FIG. 10B, lanes 2 and 6). Binding to the methylated probe was competed by preincubation with a 100-fold excess of cold methylated oligonucleotide (lane 3). Little competition was observed following preincubation with the unmethylated oligonucleotide (FIG. 10B, lane 4). This experiment provides further evidence of the methyl-CpG binding specificity of the MED1 MBD.

Figure 11A:
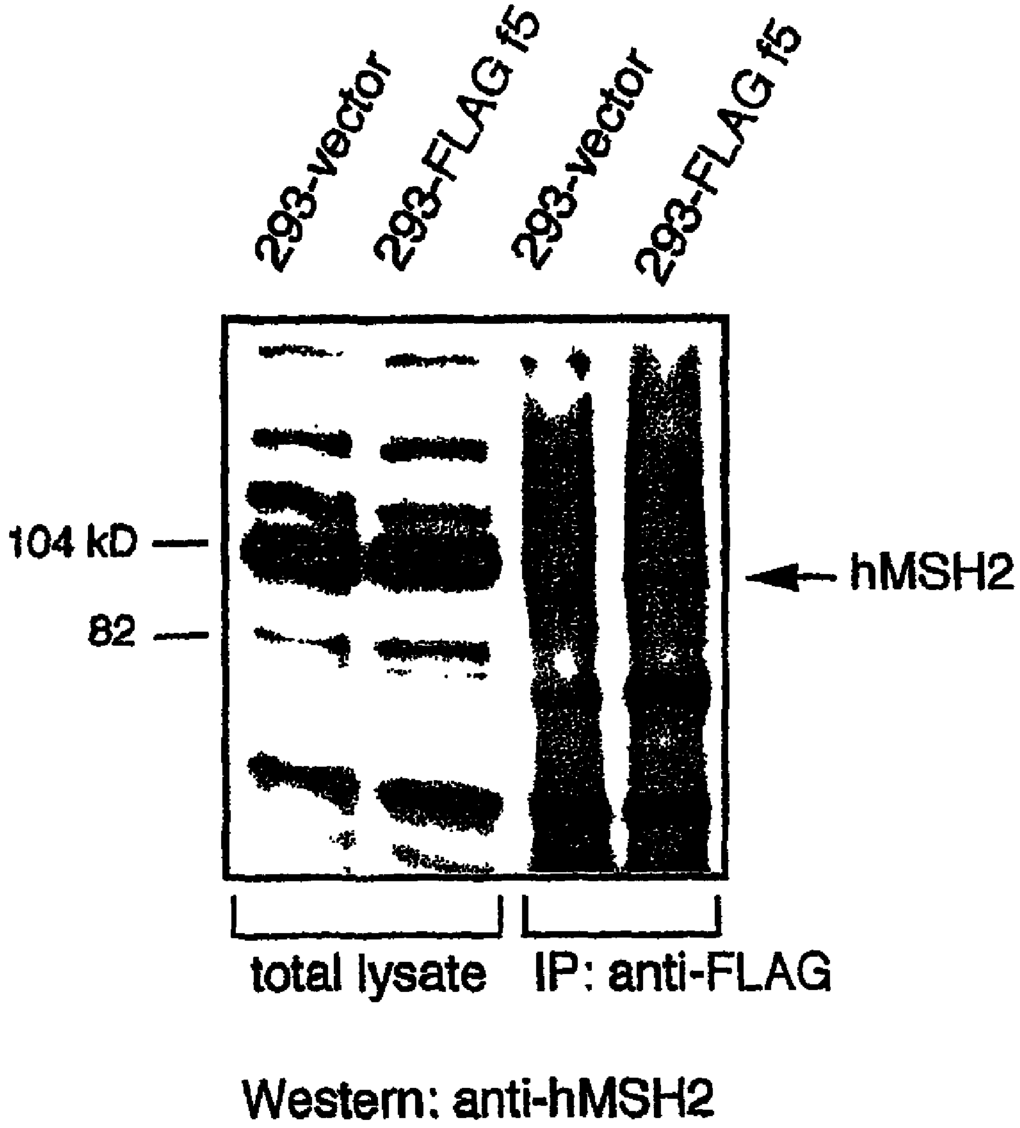
FIGS. 11A and 11B are autoradiographs showing the coimmunoprecipitation of hMSH2 with Flag-MED1/f5.
Figure 11B:
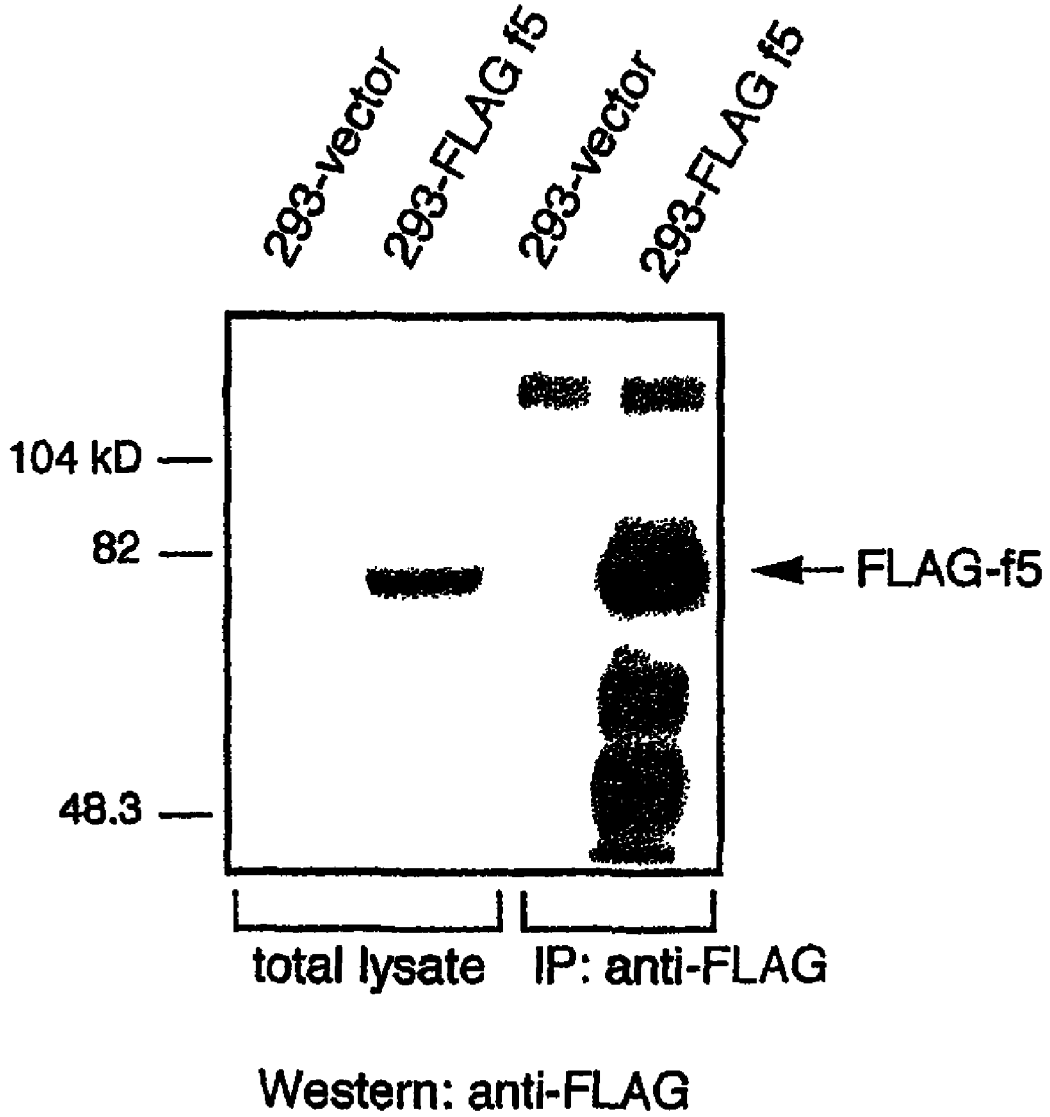

The physical association of NED1 with other DNA repair proteins was assessed as follows. 293 cells were transfected with the construct FT-MED1/f5 or with an empty expression vector. Seventy-two hours after transfection, cell lysates were prepared and immunoprecipitations carried out with anti-FLAG antibodies coupled to agarose beads. Immunoprecipitated proteins were separated by SDS-PAGE, transferred to membrane and probed with anti-hMSH2 antibody. The antibody detected a band of approximately 103 kD comigrating with hMSH2 in the anti-FLAG immunoprecipitate from FT-MED1/f5 tranfected 293 cells but not from control cells. See FIGS. 11A and 11B. This experiment demonstrates the physical association of MED1 in a complex with hMSH2.

Figure 11C:
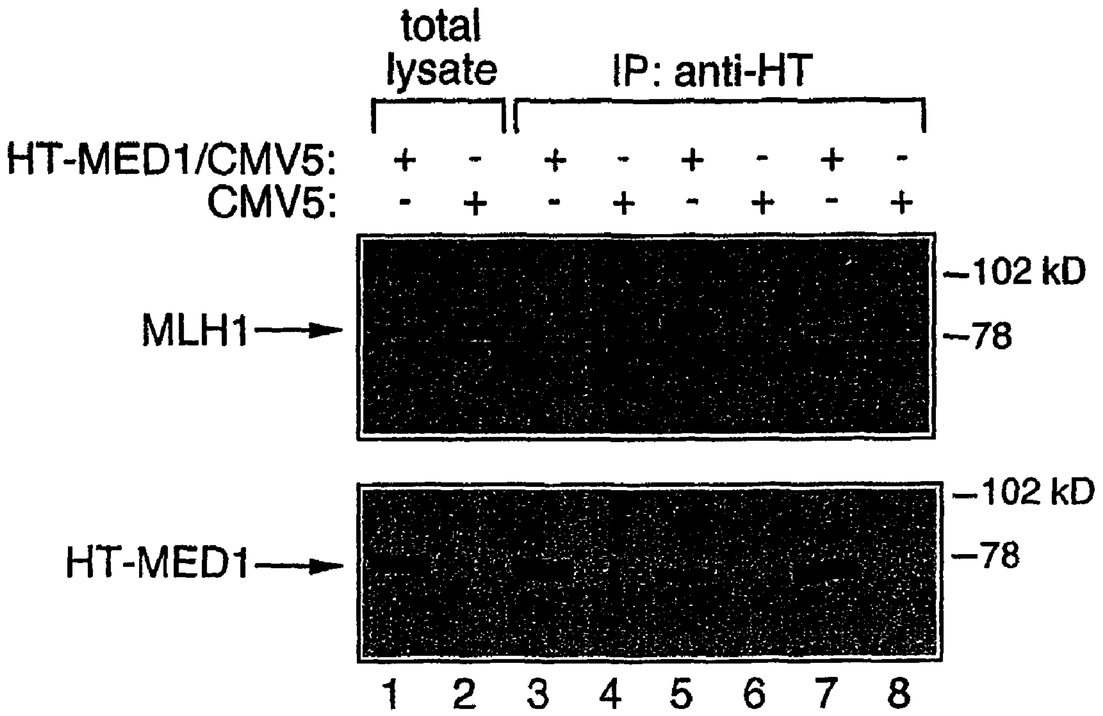

In order to confirm that the hMLH1/MED1 interaction detected in yeast also occurs in human cells, co-immunoprecipitation experiments were performed. Human kidney HEK-293 cells were transfected with a hemagglutinin-tagged construct of MED1 (HT-MED1) or with an empty expression vector. Seventy-two hours after transfection, cell lysates were prepared and immunoprecipitations were carried out with an antibody directed against the hemagglutinin tag. Immunoprecipitated proteins were separated by SDS-PAGE, transferred to a membrane and probed with an anti-MLH1 monoclonal antibody. The antibody detected a band of approximately 82 kD co-migrating with MLH1 in the anti-hemagglutinin immunoprecipitate from HT-MED1-transfected HEK-293 cells but not from control cells (FIG. 11C). This experiment suggests that MED1 is present in a complex with MLH1.

EXAMPLE II

Identification of Mutations in MED1 in HNPCC Patients

Mutational screening of the MED1 gene has been performed in ten HNPCC patients. Earlier studies on these patients revealed that they were negative for hMSH2 and hMLH1 mutations (Viel et al., (1997) Genes Chromosom Cancer 18:8-18). Polymerase chain reaction (PCR) amplification of MED1 fragments with MED1-specific primer oligonucleotides (provided in Table I), has been performed followed by direct sequencing of PCR products. A sequence variant which converts isoleucine 358 to threonine (1358T) has been identified in the germ-line of a female patient affected by two independent synchronous colon cancers. Analysis of one of the cancers revealed the loss of a normal allele. This finding is in agreement with a possible tumor suppressor role of MED1. The 1358T variant is presently being searched in other affected and unaffected individuals of the family to determine if it cosegregates with the disease. Thus, the I358T variant is present at a frequency of 1 out of 10 HNPCC patients (10%). This variant is also present in the general population at a lower frequency of approximately 3 out of 69 individuals (4.3%). Taken together these findings suggest that the I358T variant of MED1 may be associated with an increased risk for colon cancer. Additional MED1 sequence variants are being analyzed in families predisposed to cancer.

EXAMPLE III

Screening Cancer Patient DNA Samples for Mutations in MED1

A panel of 14 sporadic colorectal cancers with microsatellite instability but with no detectable defect in the two major mismatch repair genes, hMSH2 and hMLH1 (Y. Wu et al *Genes Chromosomes and Cancer* 18, 269: 1997) were screened for mutations by PCR amplification of all the MED1 exons from genomic DNA, followed by direct sequencing of PCR products with an automated DNA sequencer (ABI), using the primers shown in Table I. Some of these cancers exhibited loss of expression of MLH1.

Figure 12B:
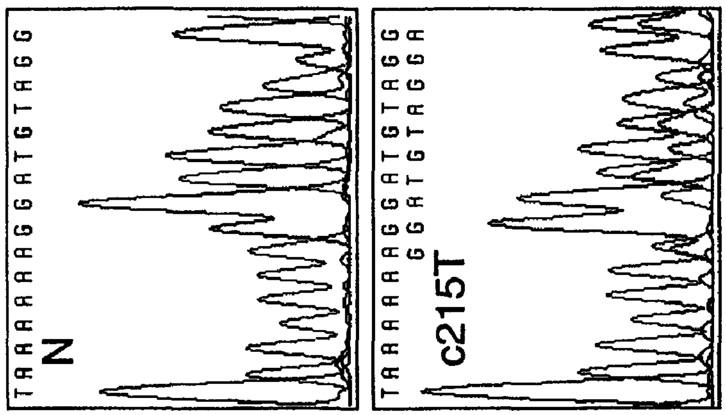
FIGS. 12A and 12B and show MED1 sequencing electropherograms (ABI) of three colon tumor DNAs and a normal control DNA. Tumors c220T and c226T harbor an apparently heterozygous adenine deletion at the (A)10 track (codons 310-313) with predicted frameshift and stop at codon 317 (FIG. 12A). The same mutation was also found in tumor c18T. Tumor c215T harbors an apparently heterozygous adenine deletion at the (A)6 track (codons 280-282) with predicted frameshift and stop at codon 302 (FIG. 12B).
Figure 12C:
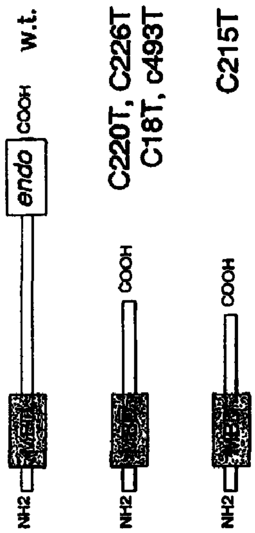
FIG. 12C shows a schematic diagram of the truncated products predicted to be encoded by the mutant MED1 alleles in the indicated tumors.
Figure 12A:
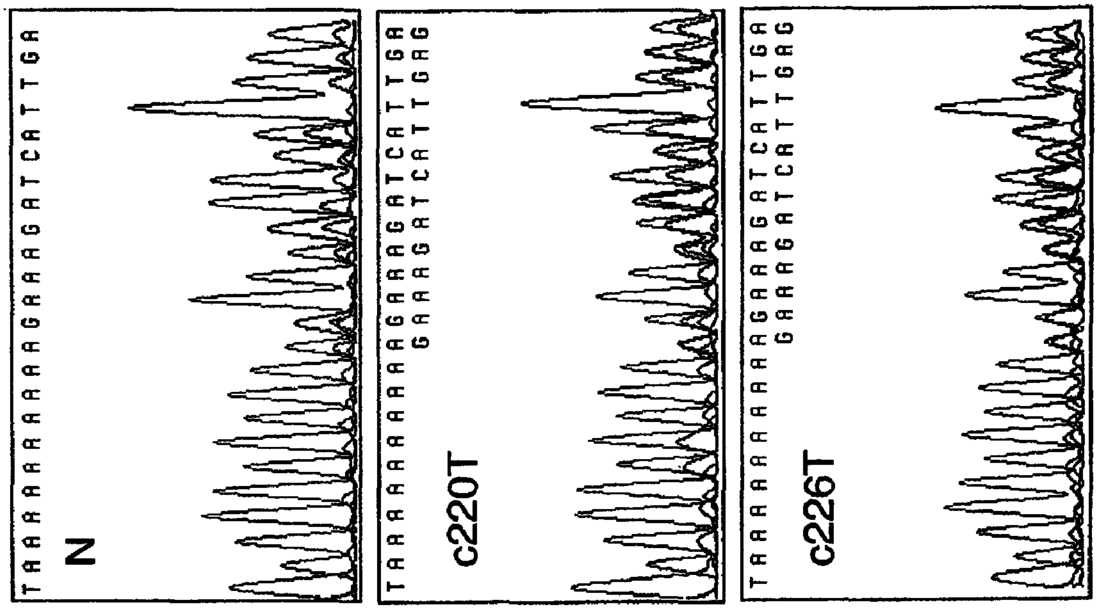

Sequence analysis revealed MED1 mutations in 4 of 14 (28.6%) tumors. In all four of these tumors, a one-base deletion occurred in one of two mononucleotide repeats [(A)6 and (A)10] located in the coding region of MED1 (FIGS. 12A and 12B) (Mutations were confirmed by sequencing at least three independent PCR products on both strands); the mutations were somatic, as they were not detected in the corresponding peripheral blood DNA. The one-base deletions cause frameshifts and predict the synthesis of truncated proteins (FIG. 12C). These alterations resemble the frameshift mutations described in the (A)8 and (C)8 tracks present in the coding region of the mismatch repair genes MSH3 and MSH6, respectively (S. Malkhosyan et al *Nature* 382:499, 1996). Furthermore, these alterations appear to be selected for in tumor cells, as similar (A)n mononucleotide repeats, including the (A)8 stretch in the coding region of PMS2, are not altered in this tumor panel. Similarly, preliminary screening experiments of 26 endometrial cancer patients led to the identification of a mutation in MED1.

TABLE II

| Patient | Sex | Tumor Site | Age at Diagnosis | MED1 Mutation | MED1 Codon | Result |
|---|---|---|---|---|---|---|
| c18T | F | caecum | 83 | (A)10 to (A)9 | 310-313 | frameshift and stop at codon 317 |
| c220T | M | traverse colon | 79 | (A)10 to (A)9 | 310-313 | same as above |
| c226T | F | ascending colon | 70 | (A)10 to (A)9 | 310-313 | same as above |

TABLE II-continued

| Patient | Sex | Tumor Site | Age at Diagnosis | MED1 Mutation | MED1 Codon | Result |
|---|---|---|---|---|---|---|
| c215T | F | caecum | 66 | (A)6 to (A)5 | 280-282 | frameshift and stop at codon 317 |
| UPN252T | F | endometrium | N/A | (A)10 to (A)9 | 310-313 | frameshift and stop at codon 317 |

Discussion

Two long-standing and closely related issues in eukaryotic mismatch DNA repair are identifying the endonuclease activity responsible for incising the DNA strand carrying the mutation, and defining the nature of the strand-targeting signal. In *E. coli*, MutH performs this function through the recognition of hemimethylated d(GATC) sites. However, eukaryotic functional homologues of MutH are not currently known. Due to the lack of information on the molecular determinants of strandedness, it was hypothesized that a reasonable approach towards the cloning of eukaryotic MutH functional homologues would be to identify hMLH1 interactors. By analogy with the MutL-MutH interaction in the bacterial system, the eukaryotic mismatch repair endonuclease is expected to be a hMLH1 interactor.

Accordingly, the "interaction cloning" of MED1, a gene encoding a viable candidate for a mismatch repair protein is described in the previous examples. The MED1 protein has several features compatible with such a role. MED1 specifically interacts with hMLH1 in the yeast system and mammalian cells, and with hMSH2 in a mammalian cell system. Whether MED1 interacts with other components of the mismatch repair complex, such as hMSH3, hMSH6/GTBP and hPMS2 has yet to be determined. MED1 has a catalytic domain showing homology to several bacterial DNA repair endonucleases, and based on this homology, it is predicted that MED1 would have N-glycosylase and possibly apurinic or apyrimidinic (AP) lyase activities. As shown in the following examples, MED-1 is a mismatch specific glycosylase, yet does not appear to possess lyase activity. Among the MED1 homologues, both the *E. coli* MutY and endonuclease III, and the *M. luteus* UV-repair endonuclease have DNA N-glycosylase and AP lyase activities. Interestingly, MutY is active on A.C, A.G and A.8-oxoG mismatches, whereas endonuclease III is active on mismatches containing some damaged derivatives of thymidine and cytosine. The homology between MED1 and the ORF10-encoded protein of *M. thermoformicicum* (Nolling et al., (1992) *Nucleic Acids Res.* 20:6501-6507) is particularly intriguing. It has been proposed that this open reading frame encodes a mismatch DNA repair enzyme, functionally associated with the methylase of the *M. thermoformicicum* restriction/modification system. ORF10 would be active on G/T mismatches originated by deamination of 5-methyl-cytosine, a product of the methylase, to thymidine under thermophilic conditions. Spontaneous deamination of 5-methyl-cytosine in CpG dinucleotides to thymidine (G.m5C→G.T) is a source of endogenous mutations in the human genome (Rideout et al., (1990) *Science* 249:1288-1290). Almost 50% of the p53 point mutations in colorectal cancer are transitions at CpG dinucleotides (Greenblatt et al., (1994) *Cancer Res.* 54:4855-4878). Conservation of MED1-related sequences involved in mismatch repair in organisms belonging to two distant phyla (Eubacteria and Archeobacteria) suggests that human MED1 is an enzyme active on DNA mispairs.

A common feature of the MED1-related endonucleases is the presence of a Cys-X6-Cys-X2-Cys-X5-Cys sequence at their carboxy terminus. This sequence, as shown in endonuclease III, ligates the [4Fe-4S] iron-sulfur cluster and defines a novel DNA binding motif (named the FCL motif), which provides the correct alignment of the enzyme along the DNA (Thayer et al., (1995) Embo J. 14:4108-4120). MED1 lacks a FCL motif at its carboxy terminus, but contains a methyl-CpG DNA binding domain at the amino terminus.

The interpretation of the MED1 mutational data requires some caution. Although it is presently unclear whether MED1 mutations promote or are the consequence of microsatellite instability, their apparent selection in tumors suggest that they may contribute to the unfolding of tumor genomic instability, as has been proposed for the MSH3 and MSH6 coding microsatellite mutations (M. Perucho, *Nature Med* 2: 630-631, 1996). Due to the variable amount of contaminating normal cells in primary tumor specimens, it is difficult to determine the homozygous or heterozygous nature of the MED1 mutations. Sequence analysis (FIG. 12) shows apparent retention in the tumors of the wild-type MED1 allele, however more extensive studies have revealed a loss of heterozygosity in this region. This may indicate that the products of the mutant alleles, which lack the catalytic domain (FIG. 12C), act in a dominant negative fashion, perhaps competing for methyl-CpG DNA binding. Alternatively, the heterozygous mutations may reduce the total amount of functional molecules (haploinsufficiency).

Like other mismatch repair genes which are mutated in HNPCC as well as in sporadic cancers with microsatellite instability, MED1 is a candidate gene for cancer genetic testing, both in HNPCC families and in sporadic cancers with microsatellite instability. It should be noted that only about 70% of HNPCC cases and only about 65% of sporadic tumors with microsatellite instability carry mutations in the known mismatch repair genes hMSH2, hMLH1, hMSH6, hPMS2 and hPMS1. The remainder 30-35% of the cases have an as yet unidentified mismatch repair defect and a fraction may therefore harbor mutations or loss of expression of MED1. Indeed, frameshift MED1 mutations were detected in both colorectal and endometrial cancers. See FIG. 12 and Table II.

EXAMPLE IV

Single-Strand Conformation Polymorphism (SSCP) Analysis of MED1 Mutations and LOH Analysis at the MED1 Locus.

As mentioned in the previous examples, mutations in MED1 encoding nucleic acids have been identified in patient tumor samples. The present example describes two approaches for identifying and characterizing MED1 mutations in patient DNA.

SSCP analysis was performed by PCR amplification of two MED1 segments encompassing the coding microsatellite repeat regions poly$(A)_{10}$ and poly$(A)_6$. In particular, PCR reactions were carried out with the MED1 primers 5'-CTCGTTGTGTTCTGAGCTTTTGGC-3'(SEQ ID NO: 30) and 5'-CAGTGTGACCAGTGAAGAAAA-3' (SEQ ID NO: 31) for analysis of the $(A)_{10}$ repeat at codons 310-313; and 5'-TGAAAGGAATCCCAATTAAG-3' (SEQ ID NO: 32) and 5'-GACAGTTCTATCAAGCTGAC-3' (SEQ ID NO: 33) for analysis of the $(A)_6$ repeat at codons 247-248.

PCR reactions were carried out in a volume of 20 μl containing: 50 ng of genomic DNA, 1.5 mM $MgCl_2$, 50 mM KCl, 10 mM Tris-HCl pH 8.3, 200 μM each of DATP, dGTP, dTTP, 40 μM dCTP, 0.1 μCi of $\alpha$-$^{32}$P dCTP (NEN-DUPONT), 1 μM each primer and 0.5 U of Taq Polymerase (Perkin Elmer/Cetus). Amplification was conducted in a MJ Research PTC 200 thermocycler for 35 cycles. Each cycle consisted of 1 min at 94° C., 1 min at 58° C. and 1 min at 72° C., followed by a 5-min extension at 72° C. After the PCR reaction, a 2 μl aliquot of the product was diluted into 20 μl of denaturing loading buffer (98% formamide, 10 mM EDTA, pH 8.0, 0.25% xylene cyanol FF, and 25% bromophenol blue), heated at 95° C. for 5 min and cooled on ice for 5 min. 3 μl of this solution were loaded on SSCP gels for electrophoretic separation.

SSCP gels consisted of 0.6×MDE solution (FMC BioProducts, Rockland, Me., USA) and 0.6×TBE buffer and were run in 0.6×TBE buffer at 6 W for 12-14 hrs at room temperature. Following electrophoresis, gels were dried and exposed to autoradiography film (X-OMAT, Kodak) overnight at room temperature.

PCR conditions for loss of heterozygosity (LOH) analysis of markers (Research Genetics) were identical to those for SSCP. PCR products were analyzed on 6% polyacrylamide gels and visualized by auto-radiography.

Results

A common theme in tumors with microsatellite instability (MSI) is the presence of frameshift mutations in microsatellites located in the coding region of target genes. Thus, the transforming growth factor β type II receptor gene (TGFBR2) is frequently inactivated in MSI-positive colorectal and gastric carcinomas, due to deletions or insertions in a coding $(A)_{10}$ track. The insulin-like growth factor II receptor gene (IGF2R) and the proapoptotic gene BAX are inactivated by mutations in coding $(G)_8$ tracks. Additional target genes in tumors with MSI, are the β2-microglobulin gene (B2M) and the tumor suppressor gene, PTEN. Interestingly, two DNA mismatch repair (MMR) genes, MSH3 and MSH6, are often somatically mutated in MSI tumors at coding $(A)_8$ and $(C)_8$ tracks, respectively. In the latter case, it has been proposed that the genomic instability develops gradually, as an initial mutation in a primary MMR gene (MSH2 or MLH1) leads to secondary MMR gene mutations, further impairing MMR functions.

Inspection of the MED1 coding sequence highlighted four potential hypermutable tracks: one $(A)_{10}$ track at codons 310-313 and three $(A)_6$ sequences at codons 247-248, 280-282, and 327-329. We screened a panel of both MSI and microsatellite-stable (MSS) primary tumors and cell lines for mutations in these polyadenine tracks by polymerase chain reaction (PCR), followed by single-strand conformational polymorphism (SSCP) analysis and direct sequencing. In addition, we cloned PCR products and obtained the sequence of multiple clones, thus allowing biochemical characterization of the mutations.

Figure 20A:
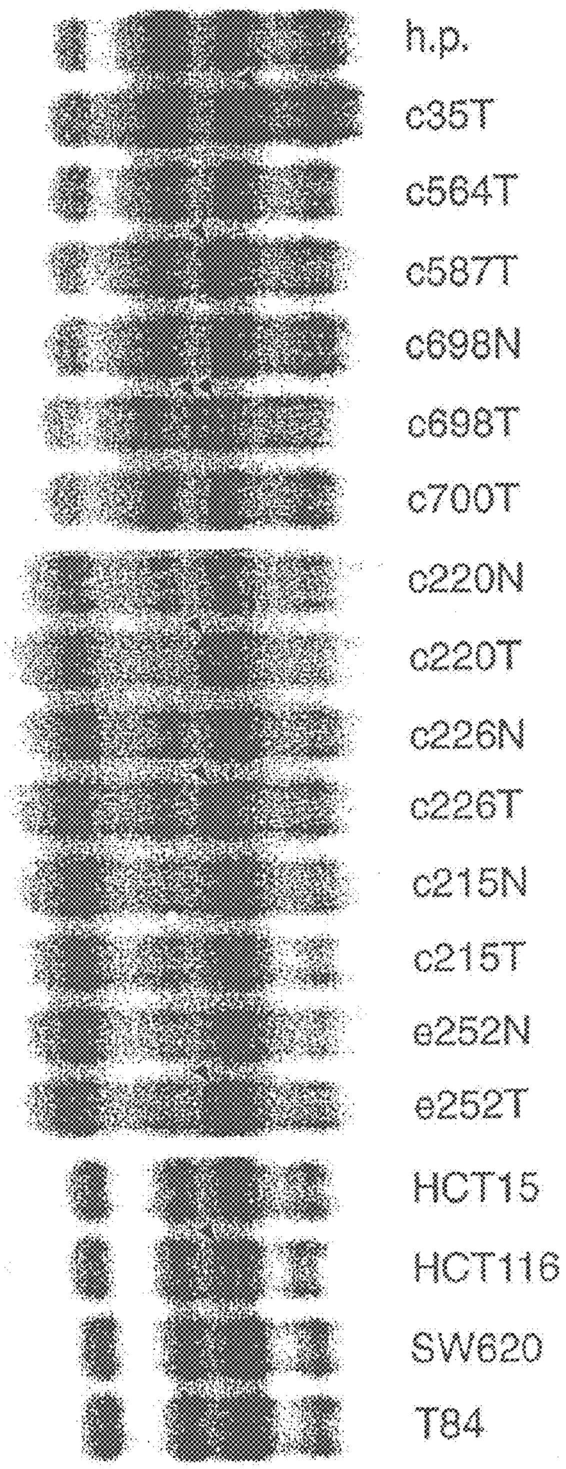
FIGS. 20 A-D show the results of genetic characterization of MED1, mutational analysis and loss of heterozygosity (LOH) studies. Mutations of MED1 at coding $(A)_{10}$ (FIG. 20A) and $(A)_6$ (FIG. 20B) tracks in microsatellite instability (MSI) carcinomas and cell lines. Single stranded conformational polymorphism (SSCP) analysis is shown for normal and tumor DNA pairs, MSI (HCT15, HCT116) and microsatellite stable (MSS) (SW620, T84) cell lines, and control normal human placental DNA (h.p.). Arrowheads indicate prominent abnormally migrating bands. HCT116 carries a one-basepair deletion at the $(A)_{10}$ track. Additional cell lines negative for mutations at this track include RK0, LS180, DU145, CaOV-3, SkOV-3, Colo205, Colo320, WiDr, SW403 and SW948.
FIG. 20C shows representative autoradiographs of LOH analysis. Case numbers are shown at the top with normal (N) and tumor (T) DNA. Dots mark the positions of alleles. Black and white arrowheads indicate allelic losses and MSI, respectively. PCR products were analyzed on 6% polyacrylamide gels and visualized by auto-radiography.
FIG. 20D shows the summary of LOH analysis at 11 LDB microsatellite markers. *Tumor c698T carries a double mutation of the MED1 $(A)_{10}$ track, as shown by SSCP and DNA sequencing.
Figure 20B:
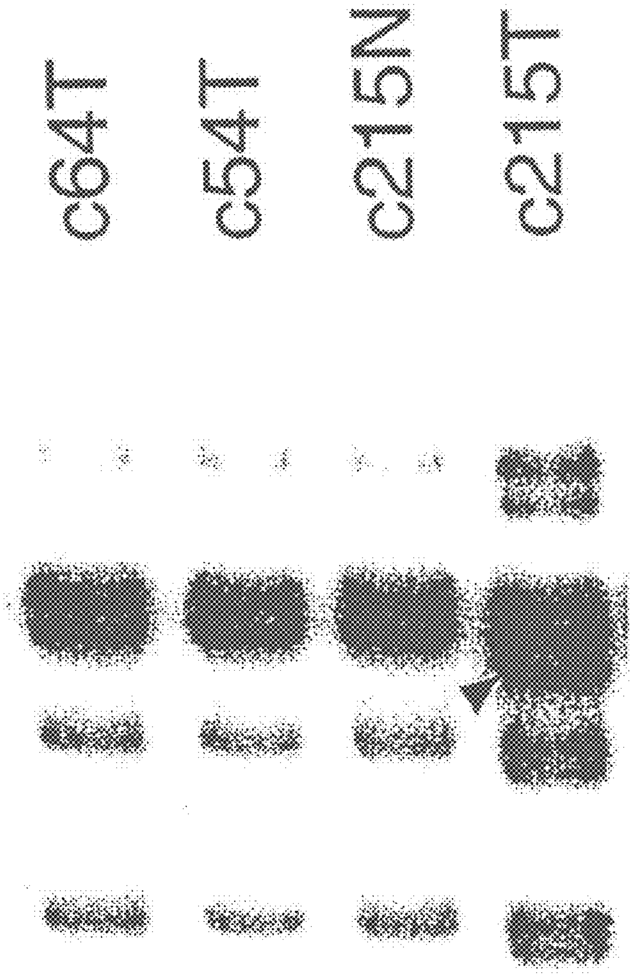

We detected MED1 mutations in 14 of 56 (25%) primary MSI tumors. Specifically, mutations were demonstrated in 11 of 42 (26.2%) colorectal carcinomas, 2 of 9 (22.2%) endometrial carcinomas and 1 of 5 (20%) pancreatic tumors (FIGS. 20A, 20B). Analysis of the corresponding normal DNAs indicated that the mutations are somatic (FIGS. 20A, 20B). None of 116 MSS tumors (39 colorectal, 36 endometrial and 41 pancreatic tumors) contained MED1 mutations at these coding polyadenine tracks, suggesting that mutations at these tracks are restricted to MSI tumors ($P<5\times10^{-6}$, Fisher's exact test). Similarly, we detected a MED1 mutation in 1 of 6 MSI cell lines (HCT116, FIG. 20A) and in none of 8 MSS cell lines (FIG. 20A). All of the mutations identified, with one exception, targeted the $(A)_{10}$ track; the exception was a mutation targeting the $(A)_6$ track at codons 247-248 (Table III). This result indicates that the $(A)_{10}$ track is a mutational hotspot in MED1. All the mutations consisted of one- or two-basepair deletions or one-basepair insertion, thus causing frameshifts and premature stop codons. The resulting truncated proteins are predicted to be non-functional, as they would lack the carboxyterminal catalytic domain, located at codons 455-580. The frameshift mutations in MED1 appear to be selected for in MSI tumor cells, as similar coding polyadenine repeats in other tested genes are rarely altered in this panel of 56 primary MSI tumors; specifically, we detected no mutation in the $(A)_8$ track of the PMS2 MMR gene, and found only two mutations in the $(A)_9$ track of the DNA helicase genes, BLM and RECQL (P=0.00122, 0.00183 and 0.00418, respectively; McNemar's test).

Figure 20C:
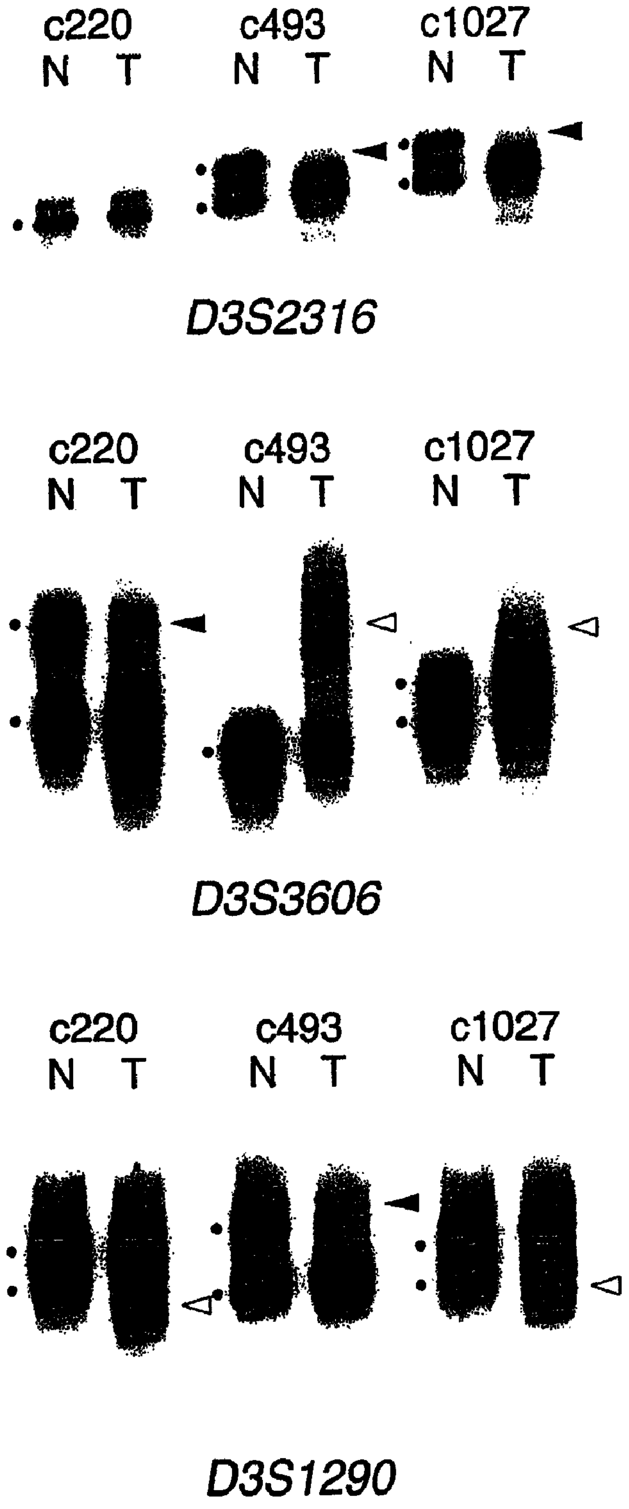
Figure 20D:
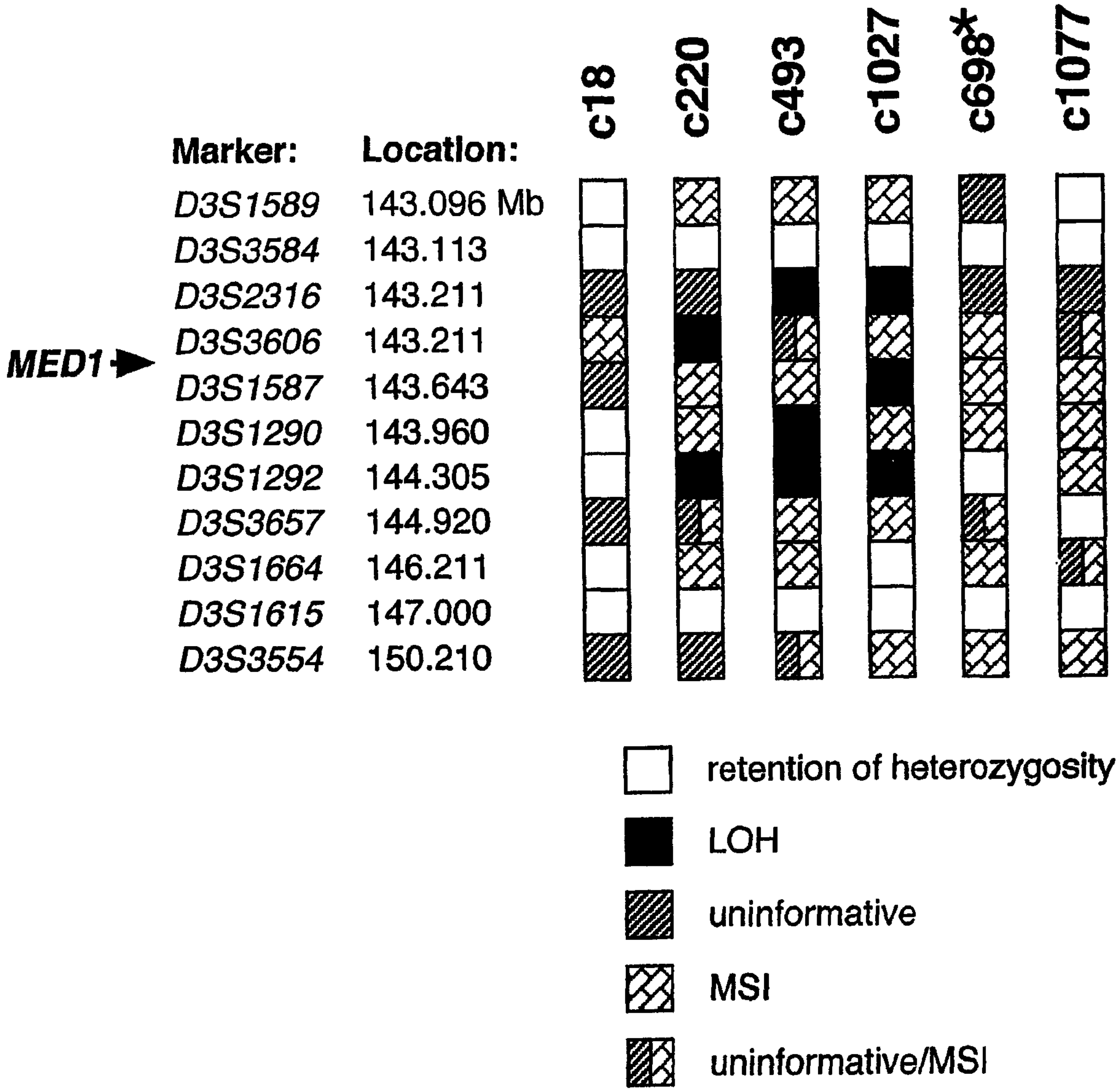

The presence of normal cells in primary tumor specimens (Table III) makes it difficult to determine the homozygous or heterozygous nature of MED1 mutations by SSCP and DNA sequencing. For this reason, we conducted loss of heterozygosity (LOH) studies on 6 of the 11 colorectal carcinomas with MED1 mutations for which sufficient amounts of matched normal and tumor DNAs were available. First, by screening the GeneMap database, we localized MED1 to a 0.4-Mb interval defined by markers D3S3606 and D3S1587. This map position confirmed our FISH data localizing MED1 to 3q21-22. See FIG. 8. We then performed LOH analysis using these two microsatellite markers and 9 other closely linked polymorphic markers derived from the Genetic Location Database (LDB) map. Thus, the following markers were used: D3S1589, D3S3584, D3S2316, D3S3606, D3S1587, D3S1290, D3S1292, D3S3657, D3S1664, D3S1615, D3S3554. Three tumors exhibited interstitial losses involving 3q21.3-22.1. The borders of the interstitial deletions were defined by the markers D3S3584 and D3S1664 (FIGS. 20C and 20D). Two dozen genes map to this 3.1-Mb region, with MED1 being the only obvious gene proposed to be involved in oncogenesis. Colorectal tumor c698T displayed no evidence of LOH, in agreement with its unique SSCP pattern (FIG. 20A) and DNA sequencing analysis, which indicated two different somatic mutations, an $(A)_9$ and an $(A)_8$ sequence at codons 310-313 (Table III). Thus, 4 of these 6 colorectal tumors had evidence of biallelic inactivation of MED1. These studies indicate that LOH analysis with the above-mentioned markers (D3S1589, D3S3584, D3S2316, D3S3606, D3S1587, D3S1290, D3S1292, D3S3657, D3S1664, D3S1615, D3S3554) provides a means to initially screen tumors for mutations in MED1. It is possible that cancer specimens without MED1 genetic mutation might exhibit loss of MED1 protein expression by other mechanisms, including promoter hypermethylation.

In colorectal tumors, the frequency of MED1 mutations was similar in HNPCC tumors associated with a known MSH2/MLH1 germline mutation (6 of 21, 28.6%) and in sporadic tumors lacking MSH2/MLH1 mutation but displaying loss of MLH1 or MSH2 expression by immunohistochemistry (5 of 21, 23.8%) (Table III). This indicates that MED1 is a frequent target of the genomic instability in MSI colorectal carcinomas regardless of their hereditary or sporadic origin. With regard to its proposed role in regulating genomic stability, MED1 alterations may represent "mutator's mutations" that contribute to the progressive unfolding of genomic instability in these tumors, as has been suggested for MSH3 and MSH6 frameshift mutations.

The following methods are provided to facilitate the practice of Example V.

Preparation of the Oligonucleotide Substrates.

The enzymatic activity of the entire MED1 protein and the catalytic domain was analyzed using as substrate 64- or 37-mer double-strand oligonucleotides set forth immediately below, containing several mismatches including insertions and a deletion The oligos were synthesized on an Applied Biosystems DNA synthesizer and purified by denaturing 15-20% PAGE-8.3M urea gel followed by DNA electroelution from the gel slices using an Amicon 57005 electroeluter.

The annealed oligonucleotides were obtained by mixing equal amounts of single-strand oligonucleotides in 10 mM Tris pH 7,5, 10 mM $MgCl_2$, 1 mM DTT, 50 mM NaCl, heating the mix at 80° C. for 15 min and then allowing the mix to slowly cool to room temperature. The labeling consisted of a fill-in reaction with the DNA polymerase enzyme Prime-It (Stratagene) at the 3' end of the bottom strand using $\alpha^{32}$P-dGTP in the same annealing buffer.

TABLE III

Pathological and molecular features of MSI tumors carrying MED1 mutations

| Sample | Tissue Type | MLH1/MSH2 Mutation | Histopathological Grade | Clinical Stage | % Tumor Cells | Codon |
|---|---|---|---|---|---|---|
| c18 | sporadic colon | none[a] | 3 | I | 90 | 310-31 |
| c215 | sporadic colon | none[a] | 2 | III | 95 | 247-24 |
| c220 | sporadic colon | none[b] | 2 | II | 15 | 310-31 |
| c226 | sporadic colon | none[a] | 3 | III | 90 | 310-31 |
| c493 | sporadic colon | none[a] | 1 | II | 75 | 310-31 |
| c35 | HNPCC | MLH1 exon 16 | 1 | III | 60 | 310-31 |
| c219 | HNPCC | MLH1 exon 17 | 3 | II | 90 | 310-31 |
| c587 | HNPCC | MLH1 exons 3-5 | 2 | II | 65 | 310-31 |
| c698 | HNPCC | MLH1 exon 16 | 2 | I | 70 | 310-31 |
| | | | | | | 310-31 |
| c1027 | HNPCC | MLH1 exon 16 | 2 | II | 65 | 310-31 |
| c1077 | HNPCC | MLH1 exon 16 | 2 | II | 65 | 310-31 |
| e4 | sporadic endometrial | ND | 3 | NA | 50 | 310-31 |
| e252 | sporadic endometrial | ND | NA | NA | NA | 310-31 |
| p108 | sporadic pancreas | ND | 2 | II | 70 | 310-31 |

[a]Loss of MLH1 and
[b]loss of MSH2 expression by immunohistochemistry.
Grade 1: well differentiated; 2: moderately differentiated; 3: poorly differentiated.
Staging of colorectal and pancreatic carcinomas is according to TNM staging system.
Percent tumour cells in specimens was estimated by light microscopy of paraffin-embedded sections.
Del: deletion;
ins: insertion.
ND: not done;
NA: not available.

EXAMPLE V

G:T Mismatch Specific Glycoslyase Activity of MED1

The enzymatic activities of MED1 have been further characterized. In accordance with the present invention, it has been determined that MED1 is a G:T mismatch specific glycoslyase.

```
5' CCGTCATGCTAGTTCACTTTATGCTTCCGGCTCXCGTCATGTGTGGAATTGTGATTAAAATCG  3'

3'  GCAGTACGATCAAGTGAAATACGAAGGCCGAGYGCAGTACACACCTTAACACTAATTTTAGCG 5'
X = A, G, C, T
Y = A, G, C, T, U, E

5' CCGTCATGCTAGTTCACTTTATGCTTCCGGCTZGCGTCATGTGTGGAATTGTGATTAAAATCG  3'

3'  GCAGTACGATCAAGTGAAATACGAAGGCCGAWJGCAGTACACACCTTAACACTAATTTTAGCG 5'
Z:W = A:T, G:C, C:G, T:A
J = T, U

                                          K
5' CCGTCATGCTAGTTCACTTTATGCTTCCGGCTCG^CGTCATGTGTGGAATTGTGATTAAAATCG  3'

3'  GCAGTACGATCAAGTGAAATACGAAGGCCGAGC.GCAGTACACACCTTAACACTAATTTTAGCG 5'
```

-continued

K = Ins A, G, C, T, GT, GTA, GTAC, GTACT, GGGGG; del C

5' CAATCCTAGCTGACACGATGTGGCCAATGGCATGACT 3'

3' TTAGGATCGACTGTGGTACACCGGTTACCGTACTGAG 5'

Figure 21:
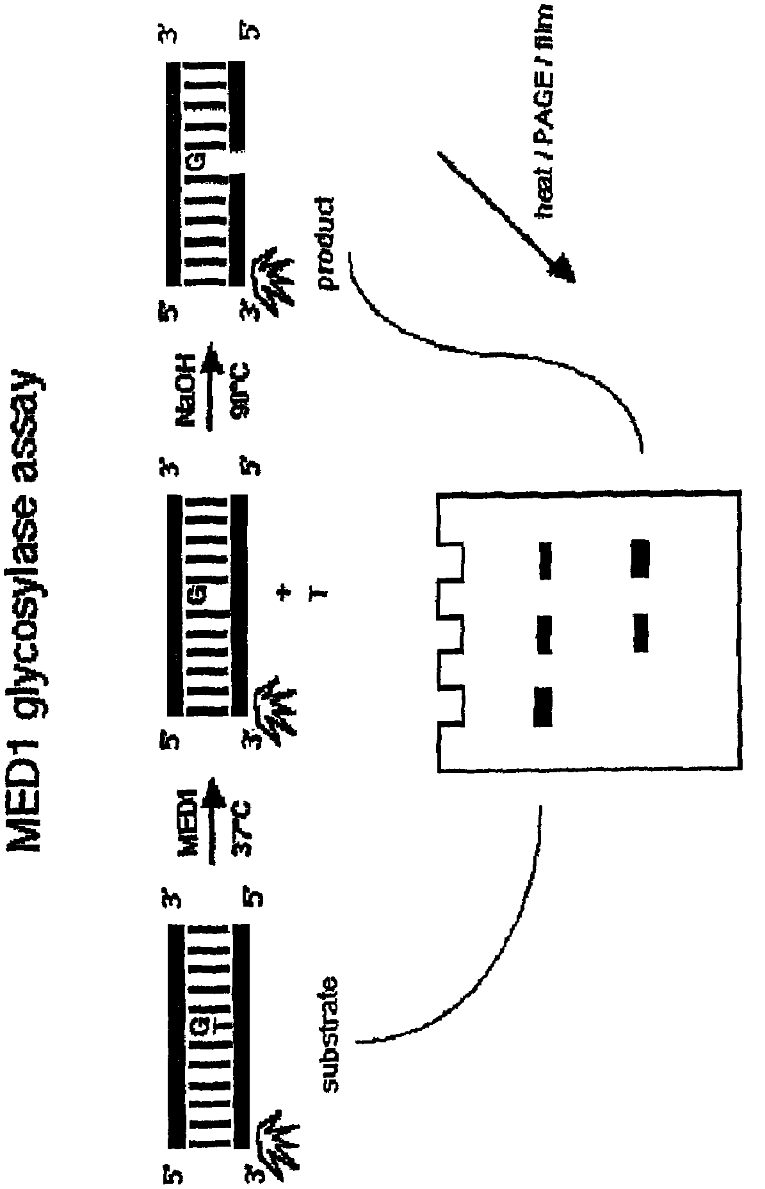
FIG. 21 depicts a schematic of a MED1 DNA N-glycosylase assay. A double-stranded oligonucleotides bearing a mismatch and $^{32}P$-labeled at the 3' end of the bottom strand is incubated with purified recombinant MED1 protein at 37° C. for 60 min, generating an abasic (AP) site. The reaction is then treated with 100 mM NaOH at 90° C. for 30 min, in order to cleave the sugar-phosphate backbone at the AP site. The resulting reaction product is separated from the longer substrate by electrophoresis on denaturing (sequencing) polyacrylamide gels. The signal is detected by autoradiography.

G = C, T, U, E
G = Guanine, C = Cytosine, T = Thymine, A = Adenine, U = Uracyl,
E = etheno Cytosine Glycosylase Assay For the glycosylase assay, a 15 μl reaction containing 5 nM of 3' end labeled oligo and 5 nM of recombinant MED1 was incubated at 37° C. for 1 hour in 20 mM Hepes, pH 7.5, 1 mM EDTA pH 8, 1 mM DTT, 0.1 mg/ml bovine serum albumin. Fifty percent of the reaction was treated with 100 mM NaOH at 90° C. for 30 min. Formamide loading buffer (95% formamide, 0.04% bromophenol blue and xylene cyanol, 20 mM EDTA and 10 mM NaOH) was added to the NaOH-treated samples and the reactions were loaded on a 15% PAGE—8.3M Urea gel in order to separate the product from the substrate. Gels were exposed to autoradiography. A schematic of this assay is shown in FIG. 21.

Results

Glycosylase Activity of MED1

As mentioned previously, the catalytic domain of MED1 bears distant homology to several bacterial DNA repair glycosylases/lyases, including MutY and endonuclease III from *E. coli*, Mig.Mth or (previously referred to as ORF10) from *M. thermoautotrophicum*, and UV endonuclease from *M. luteus*. See FIG. 4B. Whereas endonuclease III and the closely related UV endonuclease have both N-glycosylase and apurinic-apyrimidinic (AP)-lyase activity, and are active on thymine residues damaged by ring saturation, fragmentation or contraction, MutY and Mig. Mth are mismatch specific N-glycosylases. MutY is an adenine glycosylase, and possibly AP-lyase, active on A:C and A:G mismatches as well as on adenine paired with 8-oxo-guanine. Mig.Mth from the thermophilic archeon *M. thermoautotrophicum* is a thymine glycosylase active on G:T mismatches; the enzyme is equally active on G:U and to a less degree on G:G, A:G, T:C and U:C mismatches.

Figure 22:
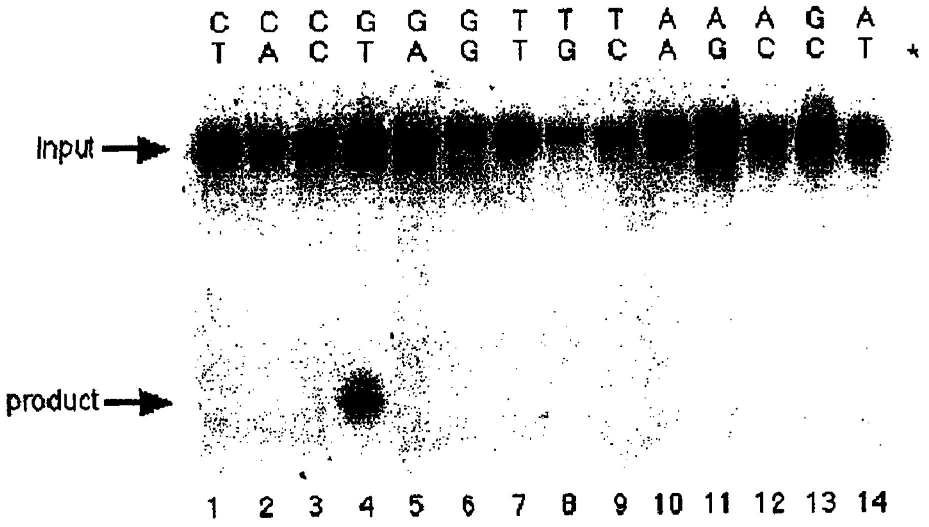
FIG. 22 is an autoradiogram showing that MED1 has a G:T mismatch-specific thymine glycosylase activity. The indicated double-stranded oligonucleotides bearing all possible mismatches and $^{32}P$-labeled on the bottom strand (marked by the asterisk) were treated with purified recombinant MED1 protein at 37° C. for 60 min. The reactions were then treated with 100 mM NaOH at 90° C. for 30 min, in order to cleave the sugar-phosphate backbone at the AP site. A band representing a cleavage product was detected for the G:T-containing oligonucleotide substrate labeled on the thymine-containing strand (lane 4). This result indicates that MED1 has thymine glycosylase activity specific for G:T mismatches. Arrows mark the expected migration of the substrate and product bands.

Based on the observed homology with these enzymes, MED1 was assayed for glycosylase activity on mismatched bases. A schematic of the glycosylase assay is shown in FIG. 21. Purified recombinant MED1 protein was incubated with $^{32}$P-labelled oligonucleotide substrates carrying all the 8 possible mismatches of the normal DNA bases. The products of the reaction were treated with strong alkali to cleave at AP sites and then were separated by electrophoresis on denaturing polyacrylamide gels. As shown in FIG. 22, a cleavage product was detected on the $^{32}$P-labeled, thymine-containing strand of a G:T substrate. A sequencing ladder indicated that the migration of the cleavage product corresponds to the site of the mismatched thymine (data not shown). No cleavage was detected on C:T or T:T mismatches (FIG. 22). In addition, no cleavage product was detected when MED1 was incubated with matched oligonucleotide substrates (FIG. 21) or with substrates containing 1 to 5 extrahelical bases. These results indicate that MED1 has thymine glycosylase activity specific for G:T mismatches.

MED1 Lacks a Detectable Lyase Activity

Figure 23:
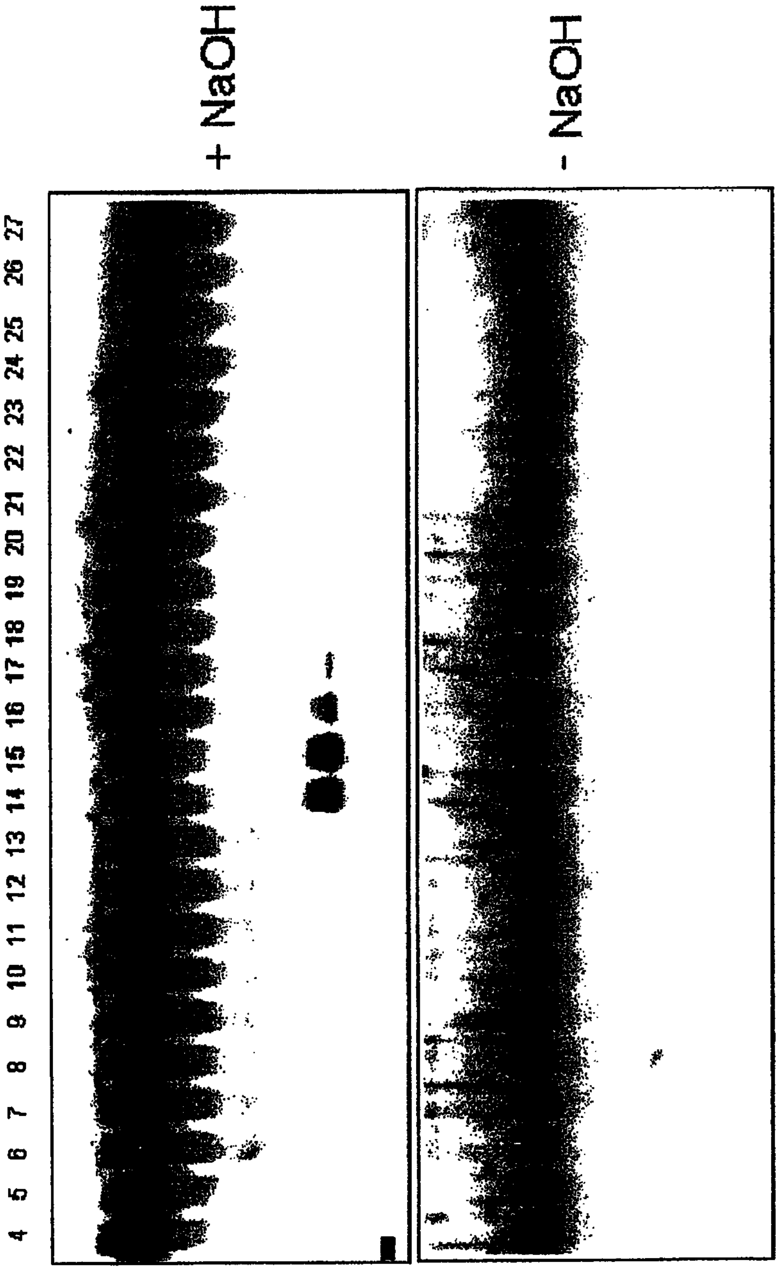
FIG. 23 is an autoradiogram showing that MED1 is a monofunctional glycosylase lacking lyase activity. The indicated fractions from a gel-filtration purification of recombinant MED1 were incubated with the $^{32}P$-labelled, G:T-containing double-strand oligonucleotide substrate. Following incubation, an aliquot of the reaction was processed with NaOH before electrophoresis (upper panel), whereas the remaining portion was subjected to electrophoresis (lower panel). A product band was detected for fractions 14 through 18 after incubation with alkali; no cleavage product was detected for these fractions when the incubation with alkali was omitted. This indicates that MED1 is a monofunctional glycosylase that lacks a detectable associated lyase activity.

In addition to the glycosylase activity, endonuclease III and UV-endonuclease perform a β-elimination reaction of the AP site with their associated AP lyase activity (bifunctional glycosylases/lyases). In order to determine whether MED1 has AP lyase activity, fractions from the last step of purification of recombinant MED1 (gel filtration) were incubated with the $^{32}$P-labeled G:T substrate. Following incubation with MED1, an aliquot of the reaction was processed with NaOH before electrophoresis, whereas the remaining directly underwent electrophoresis. As shown in FIG. 23, no cleavage was detected when the incubation of the MED1 reaction products with alkali was omitted. This indicates that MED1 is a monofunctional glycosylase that lacks a detectable lyase activity.

Figure 24:
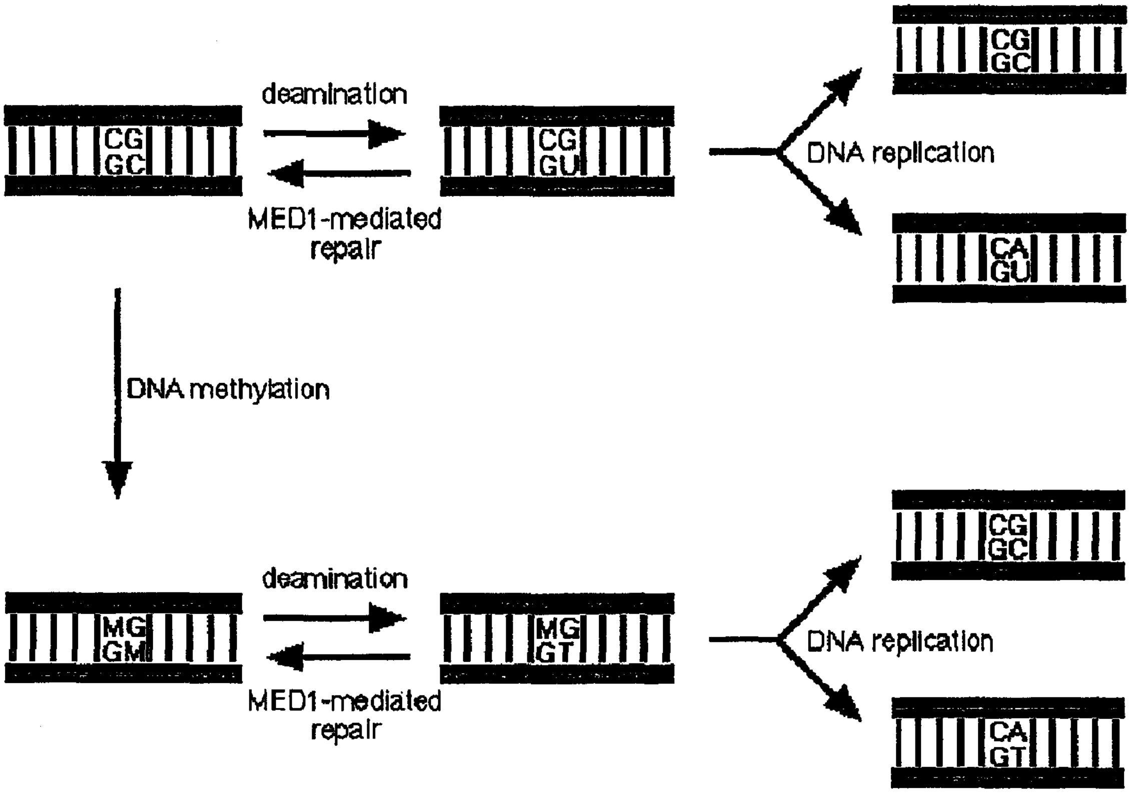
FIG. 24 is a schematic diagram depicting the mechanism by which MED1 counteracts mutagenesis by deamination of 5-methylcytosine to thymine, and of cytosine to uracil. Deamination of 5-methylcytosine (M) to thymine (T) at CpG sites generates a G:T mismatch (lower panel), whereas deamination of cytosine (C) to uracil (U) generates a G:U mismatch (upper panel). MED1 thymine and uracil glycosylase activity is the first step in the repair of these mismatches. Failure of MED1-initiated DNA repair leads to G>A (or C>T) mutation after a round of DNA replication.
Figure 25:
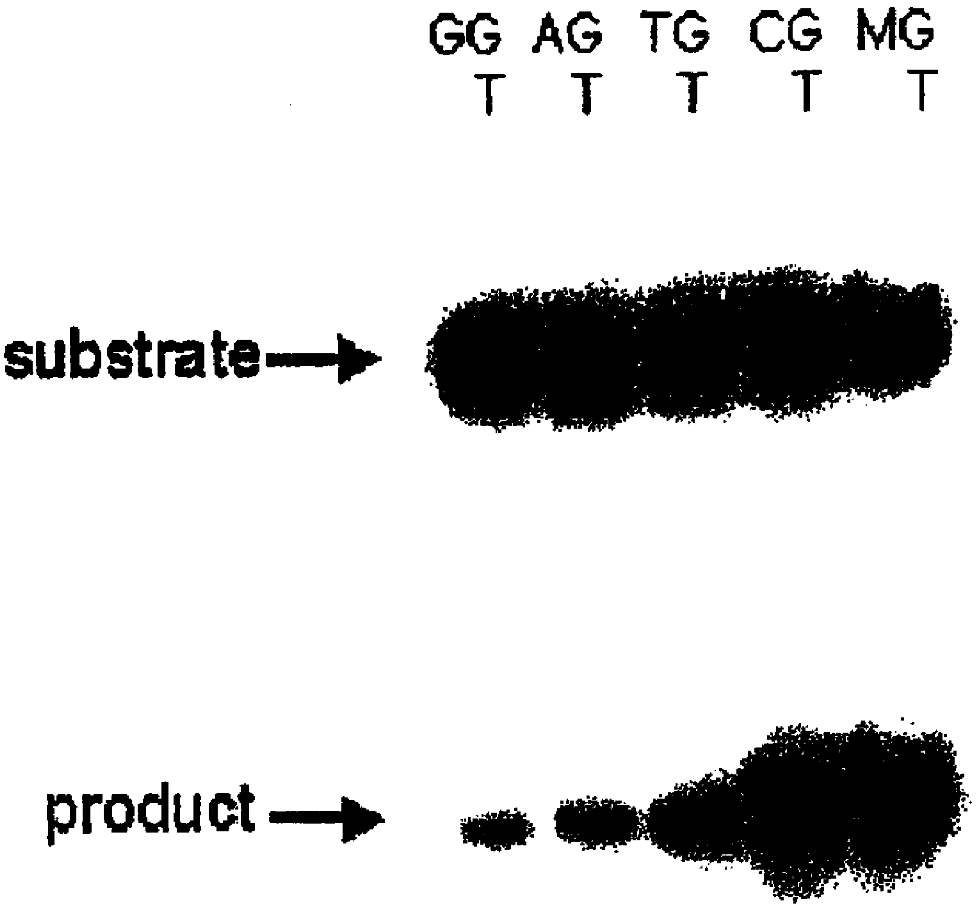
FIG. 25 shows the sequence context of MED1 G:T mismatch-specific thymine glycosylase activity: preference for CpG sites. MED1 was incubated with the indicated G:T containing oligonucleotide substrates, in which the mismatched G followed A, C, G, T or 5-methylcytosine (M). Highest thymine glycosylase activity was detected with CpG/TpG and MpG/TpG substrates, which contained a G:T mismatch in the context of a methylated or unmethylated CpG site. Only low amounts of products were generated with ApG/TpT, GpG/TpC and TpG/TpA substrates.

MED1 Thymine Glycosylase Activity in the Context of Methylated or Unmethylated CpG Sites For its G:T mismatch-specific glycosylase activity, MED1 is similar to the above mentioned Mig.Mth and the human mismatch-specific thymine glycosylase TDG, in that all 3 enzymes would counteract mutagenesis by spontaneous deamination of 5-methyl-cytosine to thymine, which would give rise to a G:T mismatch. A model of the antimutagenic activity of MED1 is shown in FIG. 24. Because cytosine methylation in mammalian cells occurs exclusively at CpG sites, we investigated whether a cytosine or 5-methylcytosine preceding the mismatched guanine is a prerequisite for MED1 thymine glycosylase activity. MED1 was incubated with oligonucleotide substrates in which the mismatched G followed A, C, G, T or 5-methylcytosine (M). As shown in FIG. 25, thymine glycosylase activity was high with CpG/TpG and MpG/TpG substrates and low with ApG/TpT, GpG/TpC and TpG/TpA substrates. Interestingly, no significant difference in activity was observed if cytosine or 5-methylcytosine preceded the mismatched guanine (FIG. 25). Thus, the fact that CpG/TpG and MpG/TpG are the optimal substrates for MED1 thymine glycosylase activity confirms that MED1 may counteract mutagenic consequences of deamination of 5-methylcytosine to thymine at CpG sites (FIG. 24).

The Catalytic Domain of MED1 is Sufficient for Glycosylase Activity

Figure 26:
FIG. 26 is a gel showing that the MED1 catalytic domain is sufficient for glycosylase activity. Increasing amounts of recombinant MED1 catalytic domain (marked "cat. dom.") and of recombinant wild type MED1 protein (marked "entire") were incubated with the $^{32}P$-labelled, G:T-containing double-strand oligonucleotide substrate and the resulting thymine glycosylase activity was evaluated. Arrows mark the expected migration of the substrate and product bands. The isolated catalytic domain and wild type MED1 proteins generated comparable amounts of product. This result indicates that the catalytic domain of MED1 is sufficient for glycosylase activity, whereas the MBD is dispensable.

The preferential activity of MED1 on substrates presenting a G:T mismatch within the context of a CpG site raises the possibility that recognition of methylated DNA by the MBD domain is important for MED1 glycosylase activity. To test this possibility, we compared the thymine glycosylase activities of wildtype MED1 and a recombinant deletion mutant lacking the MBD and encompassing only the catalytic domain (amino acids 455-580). Both CpG/TpG and MpG/TpG substrates were processed with similar efficiency (FIG. 26 and data not shown). Thus, the catalytic domain of MED1 is sufficient for glycosylase activity, whereas the MBD is dispensable.

Figure 27:
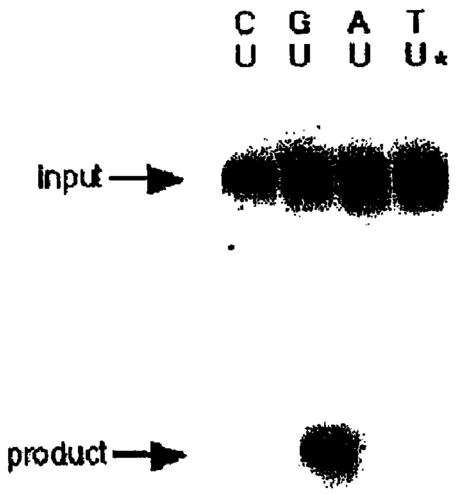
FIG. 27 is an autoradiogram showing that MED1 has a G:U mismatch-specific uracil glycosylase activity. The indicated double-stranded oligonucleotides containing uracil (U) paired with A, C, G, and T, were $^{32}P$-labeled on the bottom strand (marked by the asterisk) and treated with purified recombinant MED1 protein at 37° C. for 60 min. The reactions were then treated with 100 mM NaOH at 90° C. for 30 min, in order to cleave the sugar-phosphate backbone at the AP site. A cleavage product was detected for the G:U-containing oligonucleotide substrate labeled on the uracil-containing strand. This result indicates that MED1 has uracil glycosylase activity specific for G:U mismatches. Arrows mark the expected migration of the substrate and product bands.
Figure 28:
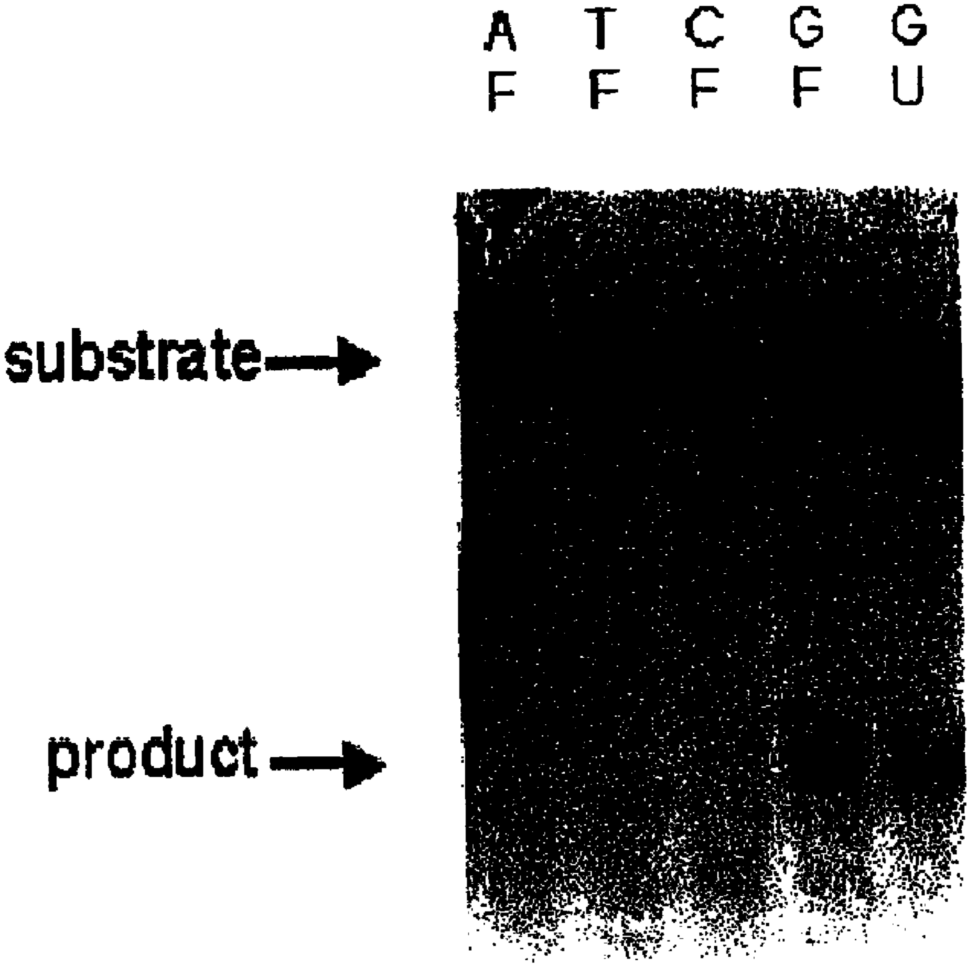
FIG. 28 is an autoradiogram which shows that MED1 has a 5-fluoruracil glycosylase activity. Recombinant MED1 protein was incubated with the indicated oligonucleotide substrates $^{32}P$-labeled on the bottom strand and containing 5-fluorouracil (F) paired with A, C, G and T, and the resulting glycosylase activity was evaluated. MED1 displayed 5-fluorouracil glycosylase activity specific for G:F mismatches. The G:U oligonucleotide substrate constitutes a positive control. Arrows mark the expected migration of the substrate and product bands.

MED1 is a G:U Mismatch-Specific Uracil Glycosylase Active also on 5-Fluorouracil Both Mig.Mth and TDG possess mismatch-specific uracil glycosylase activity. Based on the similarities with these enzymes, we tested the uracil glycosylase activity of MED1 on oligonucleotide substrates in which uracil was paired with A, C, G and T. As expected, MED1 uracil glycosylase activity is specific for G:U mismatches (FIG. 27). MED1 did not exhibit uracil glycosylase activity on single-stranded DNA (data not shown). MED1 efficiently removed the uracil analog 5-fluorouracil (F) in the context of a G:F mismatch (FIG. 28). This finding suggests that MED1 may be involved in the resistance/tolerance to 5-fluorouracil, an agent commonly used in the treatment of colorectal cancer.

MED1 acts as a 3, $N^4$-ethenocytosine glycosylase

It has been reported that human TDG and its *E. coli* homologue mismatch uracil glycosylase, Mug, recognize and efficiently remove 3, $N^4$-ethenocytosine (E). E is an exocyclic adduct formed by the reaction with DNA of metabolites of carcinogenic compounds, such as vinyl chloride and ethyl carbamate. Incubation of MED1 with oligonucleotide substrates, containing E paired with G unveiled a weak E glycosylase activity (FIG. 29).

EXAMPLE VI

Detection of Transition Single-Nucleotide Polymorphisms at CpG Sites (CpG Transition SNPs or CT-SNPs) with MED1

The most efficient mechanism for repairing a damaged or mismatched base is via a glycosylase reaction which removes the base, leaving an apurinic/apyrimidinic (AP) site. The AP site may then be further processed by AP lyase (or AP endonuclease) activity in order to create a 3' OH end suitable for incorporation of an undamaged or matched nucleotide by a DNA polymerase.

The catalytic domain of MED1 bears distant homology to several bacterial DNA repair glycosylases/lyases. By using recombinant MED1 protein and double-strand oligonucleotide substrates, we have shown that MED1 has a thymine and uracil glycosylase activity that specifically removes thymine and uracil from G:T and G:U mismatches, respectively (see previous example). This is a function similar to that of the human thymine glycosylase TDG and its bacterial homologue Mug.

By using kinetic analyses, we have shown that MED1 has high glycosylase activity on G:T and G:U mismatches and weak activity on 3, $N^4$-ethenocytosine, a cyclic adduct of cytosine formed by vinyl chloride and other industrial carcinogens (see previous example). Thus, MED1 displays the following substrate preference: G:U>G:T>>G:E (where E is 3, $N^4$-ethenocytosine). This substrate profile is comparable to those of TDG and Mug, which are G:U>G:E >>G:T and G:E>G:U>>G:T, respectively (Saparbaev and Laval, 1998). Thus, MED1 appears to have a marked preference for G:T substrates (Petronzelli et al. submitted)

Based on its G:T mismatch-specific glycosylase activity at CpG sites (FIG. 25, previous example), MED1 would counteract mutagenesis by spontaneous deamination of 5-methylcytosine to thymine (FIG. 24), which indeed would give rise to a G:T mismatch. Deamination of 5-methylcytosine to thymine is a process known to occur spontaneously at measurable rates and constitutes a major mutagenic process. Indeed, as mentioned previously, CpG sites constitute mutational hot spots in many genes, including the tumor suppressor gene p53. Deamination of 5-methylcytosine, if not repaired, would lead to C>T and G>A transitions. These transitions at CpG sites are the most frequent mutations in human cancer, including nearly 50% of all germline p53 mutations in Li-Fraumeni syndrome families and nearly 50% of all somatic p53 mutations in colorectal cancer.

It is clear that MED1 is likely to play a fundamental role in maintaining genomic fidelity at CpG sites in mammalian cells, which require cytosine methylation for gene expression regulation, but must avoid mutagenesis by spontaneous deamination of 5-methylcytosine.

Interestingly, these changes at CpG sites are also the most frequent source of human genetic variation, as demonstrated by a recent survey by the group of Dr. Chakravarti on single nucleotide polymorphisms (SNPs) at candidate genes regulating blood pressure (Halushka et al. 1999).

Since this type of SNPs are associated with genome-wide methylation at CpG sites, their origin and evolution is linked not only to the general mechanisms of mutagenesis, but also primarily to deamination of 5-methylcytosine. Thus, this class of SNPs may represent a special category. Based on these considerations, we propose that C>T and G>A transitions at CpG sites should be named CT-SNPs (for CpG sites transition single-nucleotide polymorphisms).

The availability of recombinant MED1 protein affords a general and efficient three-step method to detect CT-SNPs in target DNA molecules. This method is based on: 1) the formation of an heteroduplex containing a G:T mismatch; 2) cleavage of the heteroduplex on the T-containing strand by the combined action of MED1 followed by incubation in hot alkali; and 3) separation of the cleaved molecules from the uncleaved molecules by techniques known to those of ordinary skill in the art, such as electrophoresis.

In the first step, the T-containing strand corresponding to a given CT-SNP is detectably labeled by means which include without limitation, radioactive, fluorescent or chemiluminescent labels (CT-SNP probe). This probe may be obtained from a (possibly asymmetric) PCR reaction or may be a synthetic oligonucleotide. The probe is then annealed to an appropriately denatured DNA fragment containing the CT-SNP (for instance a PCR fragment spanning the CT-SNP).

In the second step, if the annealing of the probe to the DNA fragment generates a heteroduplex with a G:T mismatch, incubation with recombinant MED1 (or its catalytic domain) followed by incubation with NaOH at high temperature will result in the cleavage of the probe at the G:T mismatch.

In the third step, the cleaved probe can be detected by a variety of separation techniques, e.g., electrophoresis on denaturation (sequencing) polyacrylamide gel. This three-step method is schematically represented in FIG. 30.

This system requires a single CT-SNP probe for every CT-SNP to analyze. Multiple CT-SNP probes could be used to analyze a single PCR fragment containing multiple CT-SNPs, as long as the cleaved products generated by incubation with MED1 are of different length or differentially labeled (e.g., with different fluorescent dyes).

A similar method, albeit with perhaps reduced specificity, could be devised with recombinant TDG or Mug.

While certain preferred embodiments of the present invention have been described and specifically exemplified above, it is not intended that the invention be limited to such embodiments. Various modifications may be made to the invention without departing from the scope and spirit thereof as set forth in the following claims.

What is claimed is:

1. An isolated human endonuclease protein, MED1, of SEQ ID NO: 2, said encoded protein comprising an amino-terminal methyl CpG-binding domain, an internal segment rich in positively charged amino acids and a carboxy-terminal catalytic domain, said catalytic domain having deoxyribonuclease activity.

2. A pharmaceutical composition comprising a polypeptide as claimed in claim 1 and a pharmaceutically acceptable carrier.

3. A method of screening for substances which modulate the activity of a MED1 polypeptide as claimed in claim 1, said activity being selected from the group consisting of methyl CPG binding activity, nuclear localization activity, catalytic (endonuclease) activity hMLH1 binding activity, mMSH2 binding activity, glycosylase activity, or a combination thereof, the method comprising contacting at least one test substance with the MED1 polypeptide in a reaction medium, testing the-said activity of the treated MED1 polypeptide and comparing said activity with the activity of native, untreated MED1 polypeptide in a comparable reaction medium.

4. A method as claimed in claim 3, wherein said test substance is a mimetic of the MED1 polypeptide.

* * * * *